(12) United States Patent
Bonnert et al.

(10) Patent No.: US 8,158,820 B2
(45) Date of Patent: *Apr. 17, 2012

(54) COMPOUNDS

(75) Inventors: Roger Bonnert, Loughborough (GB);
Stephen Brough, Loughborough (GB);
Andrew Davies, Loughborough (GB);
Timothy Luker, Loughborough (GB);
Thomas McInally, Loughborough (GB);
Ian Millichip, Loughborough (GB);
Garry Pairaudeau, Loughborough (GB); Anil Patel, Loughborough (GB);
Rukhsana Rasul, Loughborough (GB);
Stephen Thom, Loughborough (GB)

(73) Assignee: AstraZeneca AB, Sodertalje (SE)

( * ) Notice: Subject to any disclaimer, the term of this patent is extended or adjusted under 35 U.S.C. 154(b) by 1134 days.

This patent is subject to a terminal disclaimer.

(21) Appl. No.: 10/551,783

(22) PCT Filed: Apr. 6, 2004

(86) PCT No.: PCT/SE2004/000535
§ 371 (c)(1),
(2), (4) Date: Jul. 7, 2006

(87) PCT Pub. No.: WO2004/089885
PCT Pub. Date: Oct. 21, 2004

(65) Prior Publication Data
US 2006/0264435 A1    Nov. 23, 2006

(30) Foreign Application Priority Data

Apr. 7, 2003 (SE) ........................ 0301010

(51) Int. Cl.
*C07C 63/33* (2006.01)
*A61K 31/19* (2006.01)
(52) U.S. Cl. ........................ 562/492; 514/570
(58) Field of Classification Search ............ 562/492; 514/570
See application file for complete search history.

(56) References Cited

U.S. PATENT DOCUMENTS

| 3,278,524 A | | 10/1966 | Johnson et al. |
| 3,920,846 A | | 11/1975 | Hanauye et al. |
| 3,985,779 A | | 10/1976 | Tanaka et al. |
| 4,234,742 A | | 11/1980 | Cognacq et al. |
| 4,248,618 A | | 2/1981 | Serban et al. |
| 4,670,566 A | | 6/1987 | Walsh et al. |
| 5,006,542 A | | 4/1991 | Hall et al. |
| 5,145,790 A | * | 9/1992 | Mattingly et al. ........ 436/536 |
| 5,411,972 A | | 5/1995 | Komoto et al. |
| 5,413,891 A | * | 5/1995 | Matsuura et al. ........ 430/108.11 |
| 5,532,371 A | | 7/1996 | Komoto et al. |
| 5,703,099 A | | 12/1997 | Hamanaka et al. |
| 6,150,413 A | | 11/2000 | Bernardon et al. |
| 6,376,546 B1 | | 4/2002 | Shoda et al. |
| 7,056,942 B2 | | 6/2006 | Hildesheim et al. |
| 7,067,507 B2 | | 6/2006 | Pullet et al. |
| 7,737,135 B2 | * | 6/2010 | Luker et al. .............. 514/210.17 |
| 8,003,703 B2 | | 8/2011 | Bonnert et al. |
| 8,008,350 B2 | | 8/2011 | Luker et al. |
| 2004/0029933 A1 | | 2/2004 | Zhao et al. |
| 2004/0097555 A1 | | 5/2004 | Ohkawa et al. |
| 2004/0220237 A1 | | 11/2004 | Fu et al. |
| 2005/0239881 A1 | | 10/2005 | Dunn et al. |
| 2006/0211765 A1 | | 9/2006 | Pairaudeau et al. |
| 2006/0264435 A1 | | 11/2006 | Bonnert et al. |
| 2006/0293352 A1 | | 12/2006 | Bonnert et al. |
| 2007/0249686 A1 | | 10/2007 | Bonnert et al. |
| 2008/0114002 A1 | | 5/2008 | Bonnert et al. |
| 2008/0132480 A1 | | 6/2008 | Luker et al. |
| 2008/0255150 A1 | | 10/2008 | Luker |
| 2008/0293775 A1 | | 11/2008 | Bonnert et al. |
| 2009/0012151 A1 | | 1/2009 | Bonnert et al. |
| 2009/0036535 A1 | | 2/2009 | Luker et al. |
| 2009/0149448 A1 | | 6/2009 | Alcaraz et al. |
| 2009/0192163 A1 | | 7/2009 | Luker et al. |
| 2010/0160285 A1 | | 6/2010 | Luker et al. |
| 2011/0152374 A1 | | 6/2011 | Luker et al. |

FOREIGN PATENT DOCUMENTS

| CH | 432119 | | 9/1967 |
| EP | 0006789 | | 1/1980 |
| EP | 0114734 | | 8/1984 |
| EP | 0455058 | | 11/1991 |
| EP | 0540165 | | 5/1993 |
| EP | 0622690 | | 11/1994 |
| EP | 0622816 | | 11/1994 |
| EP | 839808 | * | 5/1998 |

(Continued)

OTHER PUBLICATIONS

Dalal et al. STN Accession No. 1950:35789 Document No. 44:35789, Abstract of Journal of the Indian Chemical Society (1949), 26, 549-52.*

(Continued)

*Primary Examiner* — Nizal Chandrakumar

(57) ABSTRACT

The invention relates to substituted phenoxyacetic acids (I) as useful pharmaceutical compounds for treating respiratory disorders, pharmaceutical compositions containing them, and processes for their preparation.

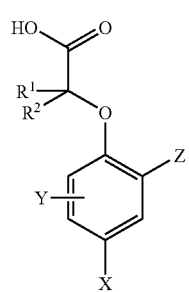

(I)

11 Claims, No Drawings

FOREIGN PATENT DOCUMENTS

| | | |
|---|---|---|
| EP | 1012142 | 6/2000 |
| EP | 1170594 A2 | 1/2002 |
| EP | 1211513 | 6/2002 |
| EP | 1471057 | 10/2004 |
| GB | 690816 | 4/1953 |
| GB | 1356834 | 6/1974 |
| GB | 1 464 977 | 2/1977 |
| GB | 1 469 687 | 4/1977 |
| GB | 2 031 408 | 4/1980 |
| GB | 2 041 363 | 9/1980 |
| GB | 1 585 963 | 3/1981 |
| JP | 07140725 * | 6/1995 |
| JP | 2003-508389 | 3/2003 |
| JP | 2006-521382 | 9/2006 |
| JP | 2006-522117 | 9/2006 |
| WO | WO 93/12086 | 6/1993 |
| WO | WO 97/08126 | 3/1997 |
| WO | WO 98/03164 | 1/1998 |
| WO | WO 99/11605 | 3/1999 |
| WO | WO 99/11627 | 3/1999 |
| WO | WO 01/16120 | 3/2001 |
| WO | WO 01/60807 | 8/2001 |
| WO | WO 01/81312 | 11/2001 |
| WO | WO 01/92224 | 12/2001 |
| WO | WO 03/064387 | 8/2003 |
| WO | WO 03/066047 | 8/2003 |
| WO | WO 03/068744 | 8/2003 |
| WO | WO 03/097042 | 11/2003 |
| WO | WO 03/097598 | 11/2003 |
| WO | WO 03/101961 | 12/2003 |
| WO | WO 2004/007451 | 1/2004 |
| WO | WO 2004/048314 | 6/2004 |
| WO | WO 2004/058164 | 7/2004 |
| WO | WO 2004/089884 | 10/2004 |
| WO | WO 2004/089885 | 10/2004 |
| WO | WO 2004/094386 | 11/2004 |
| WO | WO 2004/096777 | 11/2004 |
| WO | WO 2005/018529 | 3/2005 |
| WO | WO 2005/044260 | 5/2005 |
| WO | WO 2005/105727 | 11/2005 |
| WO | WO 2005/115382 | 12/2005 |
| WO | WO 2006/005909 | 1/2006 |
| WO | WO 2006/021759 | 3/2006 |
| WO | WO 2006/037982 | 4/2006 |
| WO | WO 2006/056752 | 6/2006 |
| WO | WO 2006/125596 | 11/2006 |
| WO | WO 2007/039736 | 4/2007 |
| WO | WO 2007/039741 | 4/2007 |
| WO | WO 2007/052023 | 5/2007 |
| WO | WO 2007/068894 | 6/2007 |

OTHER PUBLICATIONS

Hazlet et al. STN Accession No. 1941:37645 Document No. 35:37645, Abstract of Journal of the American Chemical Society (1941), 63, 1890-2.*
Ulven et al. Current Topics in Medicinal Chemistry, 2006, 6, 1427-1444.*
Ly et al. Expert Opinion Investigational Drugs 1005 14(7), 769-773.*
Ly et al. Expert Opinion Investigational Drugs 2005 14(7), 769-773.*
Amin et al., "The Fries Reaction: Part VI—the rearrangement of aryl p-toluene-sulphonates & a convenient method for synthesis of hydroxy-diarylsulphones", *Journal of Scientific Industrial Research*, vol. 13B, 1954, pp. 181-183.
Atkinson et al., "Substituted (2-Phenoxyphenyl)acetic Acids with Antiinflammatory Activity", *J. Med. Chem.*, vol. 26, 1983, pp. 1353-1360.
Baliah et al., "Fries rearrangement of the benzenesulphonates of xylenols", *Recueil des Travaux Chimiques des Pays-Bas*, vol. 80, 1961, pp. 139-148.
Bartl et al., "Thioxanthene Derivatives of Pharmacological Interest: 1,2,4-Trichloro and 2,4,5,6-Tetrachloro Derivatives of 9-(3-Dimethylaminopropylidene)Thioxanthene", *Collection Czechoslov. Chem. Commun.*, vol. 49, 1984, pp. 2295-2308.
Brown et al., "Some Chlorinated Hydroxyphenoxyacetic Acids", *Journal of the Chemical Society*, 1955, pp. 3681-3687.
Budavari, S., "The merck Index, 13$^{th}$ edition", p. 3106, monograph 3108, XP-002347170, 2001.
Cavill et al., "The chemistry of plant-growth regulators. Part I. 2:4-dichloro-6-hydroxyphenoxyacetic acid and related compounds", *Journal of the Chemical Society*, 1954, pp. 565-569.
Cecil Textbook of Medicine, 20$^{th}$ ed. (1996), vol. 2, pp. 1992-1996.
Cecil Textbook of Medicine, 20$^{th}$ ed. (1996), vol. 2, pp. 2050-2057.
Clemo et al., "Strychnine and brucine. Part II", *Journal of the Chemical Society*, vol. 125, 1924, pp. 1751-1804, XP008053173.
Cocco et al., "Annulation of functionalized hexadienones as an efficient regioselective approach to N-Aryl-2-(trifluoromethyl)-4-pyridinamines", *Tetrahedron Letters*, vol. 40, No. 23, 1999, pp. 4407-4410.
FDA mulls drug to slow late-stage Alzheimer's [online], [retrieved Sep. 24, 2003]. Retrieved from the Internet, URL; http://www.cnn.com/2003/HEALTH/conditions/09/24/alzheimers.drug.ap/index.html>.
Gallo et al., "Spirodioxolanonarenones. II. Synthesis of a halogenated 1,4-dioxaspiro[4,5]deca-7,9-diene-2,6-dione", *Journal of Chemistry*, vol. 30, No. 5, 1965, pp. 1657-1658.
Gaunt et al., "Metabolism of 4-chloro-2-methylphenoxyacetate by a soil pseudomonad", *Biochem. J.*, vol. 122, 1971, pp. 519-526.
Hazeldine et al., "Design, Synthesis and Biological Evaluation of Analogues of the Antitumor Agent, 2- {4-[(7-Chloro-2-quinoxalinyl)oxy]phenoxy}propionic Acid (XK469)", *J. Med. Chem.*, vol. 44, 2001, pp. 1758-1776.
Huston et al., "Chloro derivatives of o- and 92 -benzyl phenols. II. Some monochloro, dichloro and trichloro derivatives of ortho and para benzyl phenols", *Journal of the American Chemical Society*, vol. 55, No. 11, 1933, pp. 4639-4643.
Inukai et al., "*ortho*-Disubstituted F-benzenes. III. Preparation of (F-benzo)heterocyclic compounds from F-benzoic acid and F-phenol, and the reactions of some intermediary F-benzoyl- and F-phenoxy compounds", *Bull. Chem. Soc. Jpn.*, vol. 54, No. 11, 1981, pp. 3447-3452.
Janczewski et al., "Effect of Molecular Structure on Optical Properties of Sulfoxide Systems. o-Phenoxyphenylsulfinylacetic Acid and some of Their Derivatives. Part II", *Polish Journal of Chemistry*, vol. 62, No. 1-3, 1964, pp. 91-105, XP008053171.
Kmonicek et al., "(Tert-Amino)-11-(4-Methylpiperazino)Dibenzo[b,f]Thiepins and their 10,11-Dihydro Derivatives; Synthesis and Neuroleptic Activity", *Collection Czechoslov. Chem. Commun.*, vol. 52, 1987, pp. 792-803, XP-002347166.
Lehmler et al., "Synthesis of hydroxylated PCB metabolites with the Suzuki-coupling", *Chemosphere*, vol. 45, 2001, pp. 1119-1127.
Litvak et al., "Synthesis and $S_NAr$ reactions of new dioxins and predioxins", *Chemosphere*, vol. 43, No. 4-7, 2001, pp. 493-495.
Lupus erythematosus [online], [retrieved Dec. 28, 2006]. Retrieved from the Internet, URL; http://en.wikipedia.org/wiki/Lupus_erythematosus>.
Maeda et al., "Studies on the Synthesis and Analgesic and Anti-inflammatory Activities of 2-Thiazolyllamino- and 2-Thiazolyloxy-arylacetic Acid Derivatives", *Chem. Pharm. Bul.*, vol. 31, No. 10, 1983, pp. 3424-3445, XP-002347167.
Manoury et al., "Synthesis and Analgesic Activities of Some (4-Substituted phenyl-1-piperazinyl)alkyl 2-Aminobenzoates and 2-Aminonicotinates", Journal of Medicinal Chemistry, vol. 22(5), pp. 554-559 (1979).
Meunier et al., "Photochemical behaviour of dichlorprop [(±)-2-(2,4-dichlorophenoxy)propanoic acid] in aqueous solution", *Pest Management Science*, vol. 58, No. 8, 2002, pp. 845-852.
Moser et al., "Synthesis and Quantitative Structure-Activity Relationships of Diclofenac Analogues", *J. Med. Chem.*, vol. 33, 1990, pp. 2358-2368 , XP-001024801.
Moshchitskii et al., "Smiles rearrangement of tetrachloropyridyl methyl-hydroxyphenyl sulfone", *Chemistry of Heterocyclic Compounds*, vol. 15, No. 7, 1979, pp. 1085-1088.
Ong et al., "Synthesis and Analgesic Activity of Some Spiro[dibenz[b,f]oxepin-10,4'-piperidine] Derivatives", *J. Med. Chem.*, vol. 22, No. 7,1979, pp. 834-839, XP-002347163.
Rajsner et al., "Fluorinated tricyclic Neuroleptics: Synthesis and Pharmacology of 8-Fluoro-4-(4-Methylpiperazino)-4,5-

Dihydrothieno[2,3-*b*]-1-Benzothiepin", *Collection Czechoslov. Chem. Commun.*, vol. 44, 1979, pp. 2997-3007, XP-002347164.

Selvi et al., "Vilsmeier cyclization of 2-amino phenoxyacetic acid", *Synthetic Communications*, vol. 31, No. 14, 2001, pp. 2199-2202.

Sindelar et al., "Synthesis of 3-Chloro-5-(4-Methylpiperazino)-6,7-Dihydro-5*H*-Dibenzo[*b,g*]Thiocin, An Eight-Membered Ring Homologue of the Neuroleptic Agent Octoclothepin", *Collection Czechoslov. Chem. Commun.*, vol. 45, 1980, pp. 491-503, XP-002347160.

Sindelar et al., "Fluorinated Tricyclic Neuroleptics with Prolonged Action: 3-Fluoro-8-Trifluoromethyl Derivatives of 10-(4-Methylpiperazino)- and 10-[4-(2-Hydroxyethyl)Piperazino]-10,11-Dihydrodibenzo-[*b,f*]Thiepin", *Collection Czechoslov. Chem. Commun.*, vol. 46, 1981, pp. 118-140, XP-002347168.

Sindler-Kulyk et al., "Synthesis of New 3-(Phenoxyphenyl)sydnones", *J. Hetercyclic Chem.*, vol. 29, No. 2, 1992, pp. 1013-1015, XP-002347161.

Stokker et al., "3-Hydroxy-3-methylglutaryl-coenzyme A Reductase Inhibitors. 5. 6-(Fluoren-9-yl)-and 6-(Fluoren-9-ylidenyl)-3,5-dihydroxyhexanoic Acids and Their Lactone Derivatives", *J. Med. Chem.*, vol. 29, 1986, pp. 852-855.

Thuillier, G., "Derives des acides 24 aryloxyacetiques a activite neurotrope", *Chimique Therapeutique*, vol. 1, No. 2, 1966, pp. 82-86.

Walsh et al., "Antiinflammatory Activity of *N*-(2-Benzoylphenyl)alanine Derivatives", *J. Med. Chem.*, vol. 27, 1984, pp. 1317-1321, XP-002347162.

Wheatley et al., "2-Benzylphenol Derivatives. III. Basic Ethers", *Journal of American Chemical Society*, vol. 71, No. 11, 1949, pp. 3795-3797.

Database CA [Online] Chemical Abstracts Service, Columbus, Ohio, US; XP002372494 retrieved from STN Database accession No. 1956:16264 abstract & Ott, Donald G. et al: "A carbon-14 tracer study of the alkaline rearrangement of chlorophenanthraquinones" *Journal of the American Chemical Society*, vol. 77, 2325-2329 CODEN:JACSAT; ISSN:0002-7863, 1955.

Database CAPLUS [Online] Chemical Abstracts Service, Columbus, Ohio, US; 1992, XP002372495 retrieved from STN Database accession No. 1992:255529 abstract & Ram, Bhagat et al: "Potential hypolipidemic agents part VI: synthesis and biological activity of some new 4-chloro/methyl-2-pyrazolylphenoxy alkanoates", *Indian Drugs*, vol. 29, No. 6, 1992, pp. 258-262.

Database WPI 1-3, 5, Section Ch, Week 200365 19, 20, Derwent Publications Ltd., London, GB, AN 2003-689635 XP-002301315, WO03068744A1, Ishihara Sangyo Kaisha, Ltd., Aug. 21, 2003.

STN International, File CAPLUS, CAPLUS accession 1-10, No. 1987:597776, document No. 107:197776, Otsuka Pharmaceutical Factory, "Preparation of aminophenol derivatives as anticoagulants, analgesics, hypotensives, and diuretics", JP, A2, 62108859, 19870520.

STN International, File CAPLUS, CAPLUS accession 1-5, 10, No. 1979:186607, document No. 90:186607, Ciba-Geigy, "Phenoxyphenoxyalkanecardoxylic acid derivatives", DE, A1, 2832435, 19790208.

STN International, File CAPLUS, CAPLUS accession 1-5, 10, No. 1971:53748, document No. 74:53748, Walker et al., "Synthesis of 5-phenyl-2,3,4,5-tetrahydro-1,4-benzoxazepines and corresponding 3-ones", & *Journal of Organic Chemistry* (1970), 36(2), 305-308.

STN International, File CAPLUS, CAPLUS accession 1-3, 5, 10, No. 1992:407796, document No. 117:7796, Tokuyama Soda Co., Ltd., "Preparation of thienyloxphenoxy group-containing carboxylic acids as microbicides", JP, A2, 04021677, 19920124.

STN International, File CAPLUS, CAPLUS accession 1-3, 5, 10, No. 1975:402045, document No. 83:2045, Shiley et al., "Fungicidal activity of some fluoroaromatic compounds", *Journal of Fluorine Chemistry* (1975), 5(4), 371-376.

STN International, File CAPLUS, CAPLUS accession 1, 3, 5, 10, No. 1972:405106, document No. 77:5106, Oniscu et al., "Monoethanolaminosulfonyl-,diethanolaminosulfonyl- and morpholinosulfonyl-phenoxyacetic derivatives", Buletinul Institutului Politehnic din Iasi, (1971), 14(3-4), 101-114.

STN International, File CAPLUS, CAPLUS accession 1, 3, 5, 10, No. 1961:22702, document No. 55:22702, Takano, K., "Condensation products of furfuryl alcohol. IV. Condensation products of furfuryl alcohol with cresols", Nippon Kagaku Zasshi (1959), 80, 678-681.

STN International, File CAPLUS, CAPLUS accession 1, 3-5, 10, No. 1958:25331, document No. 52:25331, Landa et al., "Properties of sulfide catalysts. V. Preparation of alkylphenols", Chemicke Listy pro Vedu a Prumysl (1957), 51, 1851-1857.

STN Intenational, File CAPLUS, CAPLUS accession 1, 3, 5, 10, No. 1971:498288, document No. 75:98288, Botez et al., "Phenoxybutyric acid sulfamides. I. Sulfamide derivatives of the α-phenoxy-, α-cresoxy-, and α-xylenoxybutyric acids", Buletinul Institutului Politehnic din Iasi (1970), 16(1-2), 161-172.

STN International, File CAPLUS, CAPLUS accession 1-7, 10, No. 1986:109631, document No. 104:109631, Yoshitomi Pharmaceutical Industries, Ltd., "Imidazole derivatives", JP, A2, 60142965, 19850729.

Vippagunta et al., "Crystalline solids", *Advanced Drug Delivery Reviews* 48:3-26 (2001).

Inflammatory Bowel Disease [online] {retrieved on Apr. 7, 2008 from the internet} {URL:http://www.emedicinehealth.com/script/main/art.asp?articlekey=59121&pf=3&page=8}.

Rheumatoid arthritis [online] {retrieved on Apr. 7, 2008 from the internet} {URL:http://www.nlm. nih.gov/medlineplus/ency/article/000431.htm}.

Asthma [online] [retrieved on May 30, 2008] retrieved from the Internet URL:http://www.nlm.nih.gov/medlineplus/ency/article/000141.htm.

Chiu et al., "Derivation and Properties of Recombinant Fab Antibodies to Coplanar Polychlorinated Biphenyls", *J. Agric. Food Chem.* 48:2614-2624 (2000).

Golub et al., "Molecular Classification of Cancer: Class Discovery and Class Prediction by Gene Expression Monitoring", *Science* 286:531-537 (1999).

Morissette et al., "High-throughput crystallization: polymorphs, salts, co-crystals and solvates of pharmaceutical solids", *Advanced Drug Delivery Reviews* 56:275-300 (2004).

Rhinitis [online] retrieved on Nov. 12, 2008. Retrieved from URL; http://www.healthline.com/galecontent/rhinitis?print=true.

RN 110624-55-0, retrieved from CAPLUS; retrieved on Apr. 7, 2008.

USPTO Office Action in U.S. Appl. No. 10/552,082, mailed Oct. 29, 2007, 6 pages.

Fish & Richardson P.C., Amendment in Reply to Action of Oct. 29, 2007 in U.S. Appl. No. 10/552,082, filed Feb. 29, 2008, 18 pages.

USPTO Final Office Action in U.S. Appl. No. 10/552,082, mailed Jun. 9, 2008, 18 pages.

Fish & Richardson P.C., Amendment in Reply to Action of Jun. 9, 2008 in U.S. Appl. No. 10/552,082, filed Sep. 9, 2008, 11 pages.

USPTO Office Action in U.S. Appl. No. 10/552,082, mailed Dec. 4, 2008, 23 pages.

Fish & Richardson P.C., Amendment in Reply to Action of Dec. 4, 2008 in U.S. Appl. No. 10/552,082, filed Apr. 6, 2009, 8 pages.

USPTO Notice of Allowance in U.S. Appl. No. 10/552,082, mailed Jul. 1, 2009, 9 pages.

USPTO Office Action in U.S. Appl. No. 10/569,065, mailed May 4, 2007, 12 pages.

Fish & Richardson P.C., Amendment in Reply to Action of May 4, 2007 in U.S. Appl. No. 10/569,065, filed Aug. 3, 2007, 14 pages.

USPTO Final Office Action in U.S. Appl. No. 10/569,065, mailed Oct. 17, 2007, 4 pages.

Fish & Richardson P.C., Amendment in Reply to Action of Oct. 17, 2007 in U.S. Appl. No. 10/569,065, filed Jan. 17, 2008, 9 pages.

USPTO Office Action in U.S. Appl. No. 10/569,065, mailed Apr. 16, 2008, 14 pages.

Fish & Richardson P.C., Amendment in Reply to Action of Apr. 16, 2008 in U.S. Appl. No. 10/569,065, filed Jul. 16, 2008, 38 pages.

USPTO Office Action in U.S. Appl. No. 10/569,065, mailed Oct. 28, 2008, 15 pages.

Fish & Richardson P.C., Amendment in Reply to Action of Oct. 28, 2008 in U.S. Appl. No. 10/569,065, filed Jan. 27, 2009, 7 pages.

USPTO Office Action in U.S. Appl. No. 10/569,065, mailed May 13, 2009, 10 pages.

Fish & Richardson P.C., Amendment in Reply to Action of May 13, 2009 in U.S. Appl. No. 10/569,065, filed Jul. 14, 2009, 9 pages.

USPTO Office Action in U.S. Appl. No. 11/574,076, mailed Oct. 27, 2008, 23 pages.
Fish & Richardson P.C., Amendment in Reply to Action of Oct. 27, 2008 in U.S. Appl. No. 11/574,076, filed Apr. 27, 2009, 21 pages.
USPTO Office Action in U.S. Appl. No. 11/574,076, mailed Aug. 18, 2009, 7 pages.
USPTO Office Action in U.S. Appl. No. 11/576,372, mailed Jul. 22, 2009, 19 pages.
USPTO Office Action in U.S. Appl. No. 12/089,276, mailed Jun. 17, 2009, 28 pages.
Fish & Richardson P.C., Amendment in Reply to Action of Jun. 17, 2009 in U.S. Appl. No. 12/089,276, filed Sep. 22, 2009, 10 pages.
USPTO Office Action in U.S. Appl. No. 12/092,431, mailed Aug. 4, 2009, 8 pages.
Gavezzotti, "Are Crystal Structures Predictable?", *Acc. Chem. Res.* 27:309-314 (1994).
Fish & Richardson P.C., RCE and Interview Summary in response to Notice of Allowance of Jul. 1, 2009 in U.S. Appl. No. 10/552,082, filed Sep. 30, 2009, 2 pages.
USPTO Office Action in U.S. Appl. No. 10/552,082, mailed Jan. 7, 2010, 12 pages.
USPTO Notice of Allowance in U.S. Appl. No. 10/569,065, mailed Oct. 23, 2009, 10 pages.
Fish & Richardson P.C., RCE and IDS in Reply to Notice of Allowance of Oct. 23, 2009 in U.S. Appl. No. 10/569,065, filed Nov. 5, 2009, 3 pages.
Fish & Richardson P.C., RCE and Amendment in Reply to Action of Aug. 18, 2009 in U.S. Appl. No. 11/574,076, filed Dec. 18, 2009, 13 pages.
Fish & Richardson P.C., Amendment in Reply to Action of Jul. 22, 2009 in U.S. Appl. No. 11/576,372, filed Jan. 22, 2010, 18 pages.
USPTO Notice of Allowance in U.S. Appl. No. 12/089,276, mailed Jan. 4, 2010, 6 pages.
Fish & Richardson P.C., Amendment in Reply to Action of Aug. 4, 2009 in U.S. Appl. No. 12/092,431, filed Feb. 3, 2010, 15 pages.
USPTO Office Action in U.S. Appl. No. 12/167,513, mailed Nov. 2, 2009, 19 pages.
Fish & Richardson P.C., Amendment in Reply to Action of Nov. 2, 2009 in U.S. Appl. No. 12/167,513, filed Feb. 2, 2010, 19 pages.
Fromageot et al., "Photodecarboxylation of 2-(2'-carboxymethoxy-5'-methylphenyl)-benzotriazole", *Journal of Photochemistry and Photobiology, A: Chemistry* 44(1):93-98 (1988).
Ram et al., "Potential Hypolipidemic Agents Part VI: Synthesis and Biological Activity of Some New 4-Chloro/Methyl-2-pyrazolylphenoxy Alkanoates", *Indian Drugs* 29(6), 258-262 (1992).
Fish & Richardson P.C., Amendment in Reply to Action of Jan. 7, 2010 in U.S. Appl. No. 10/552,082, filed Jul. 2, 2010, 8 pages.
U.S. Examiner Shawquia Young, USPTO Notice of Allowance in U.S. Appl. No. 10/552,082, mailed Sep. 15, 2010, 12 pages.
AstraZeneca AB: WO03066046 & WO03066047, "The use of indole-3-acetic acids as CRTH2 receptor antagonists", *Expert Opin. Ther. Patents* 14(1):125-128 (2004).
Berhenke et al., "Some Aryloxyaliphatic Acids", *Journal of the American Chemical Society* 73:4458 (1951).
Burger, "Isosterism and bioisosterism in drug design", in Progress in Drug Research 287-328 (Ernst Jucker, ed., Birkhauser Verlag, 1991).
Chemical abstract 123:213132 in CAS (or JP07140725), 1995.
Chemical abstract 123:22081 in CAS (or EP622690), 1995.
Chemical abstract 116:123167 in CAS (or EP455058), 1992.
Chemical abstract 85:56485 in CAS or Parli et al., "The relation between the metabolism of 2,4-dichloro-6-phenylphenoxyethylamine (DPEA) and related compounds and their activities as microsomal mono-oxygenase inhibitors", Drug Metabolism and Disposition 1(4):628-33 (1973).
Chemical abstract 69:93942 in CAS or Cheng et al., "Phenylphenol derivatives with biological activity. III. Fungistatic activity of phenylphenol derivatives", Agricultural and Biological Chemistry 32(9):1162-74 (1968).
Chemical abstract 49:86470 in CAS or Mel'nikov et al., "Structure and physiological activity of alkyl- and aryl-phenoxyacetic acids and their derivatives", Fiziologiya Rastenii 2:267-70 (1955).

Chemical abstract 35:37645 in CAS or Hazlet et al., "The Bromination of 2-Phenylphenyl Acetate", Journal of the American Chemical Society 63:1890-2 (1941).
Coxworth, "Synthesis of Chlorinated 2-(3-Benzofuranyl)Phenols", *Canadian Journal of Chemistry* 44:1092-1096 (1966).
"DialogWeb Records", http://www.dialogweb.com/cgi/document?req=1284661379410, accessed Sep. 16, 2010.
Ebenezar et al., "Prostaglandins in the patent literature", *Expert Opin. Ther. Patents* 17(9):1131-1145 (2007).
Manske et al., "Synthesis and Reactions of Some Dibenzoxepins", *Journal of American Chemical Society* 72:4797-4799 (1950).
Ono Pharm. Co. Ltd: WO03022813 & WO03022814, "The use of prostaglandin $D_2$ receptor antagonists to treat allergic rhinitis", *Expert Opin. Ther. Patents* 13(10):1657-1661 (2003).
Patani et al., "Bioisosterism: A Rational Approach in Drug Design", *Chem. Rev.* 96:3147-3176 (1996).
Petrillo et al., "$S_{RN}1$ C-Arylation of Potassium Aryloxides by Arylazo Phenyl or Tert-Butyl Sulfides in DMSO", Tetrahedron 46(23):7977-7990 (1990).
Ueda et al., "The Synthesis of 10-(4-Methylpiperazino)dibenzo[b,f] thiepin and Related Compounds. Neurotropic and Psychotropic Agents", *Chem. Pharm. Bull.* 23(10):2223-2231 (1975).
Wermuth, "Molecular Variations Based on Isosteric Replacements", The Practice of Medicinal Chemistry, 1996, chapter 13, pp. 203-237.
Preventing Asthma Symptoms [online] [retrieved on Apr. 23, 2010 from the internet] URL:http://www.webmd.com/asthma/guide/asthma-prevention.
Allergic Rhinitis—Prevention [online] [retrieved on Apr. 23, 2010 from the internet] URL:http://www.webmd.com/allergies/tc/allergic-rhinitis-prevention.
COPD Treatments: Improving Your Quality of Life [online] [retrieved on Apr. 23, 2010 from the internet] URL:http://www.webmd.com/lung/copd/copd-treatments-improving-your-quality-of-life.
Database Beilstein chemical extract accession No. 6722243, Jan. 2010.
Database Beilstein chemical extract accession No. 6722682, Jan. 2010.
Database Beilstein chemical extract accession No. 3532059, Jan. 2010.
Database Beilstein chemical extract accession No. 2533336, Jan. 2010.
Database Beilstein chemical extract accession No. 2537173, Jan. 2010.
Database Beilstein chemical extract accession No. 3385275, Jan. 2010.
Database Beilstein chemical extract accession No. 3386554, Jan. 2010.
USPTO Notice of Allowance in U.S. Appl. No. 10/569,065, mailed Jan. 28, 2010, 9 pages.
Fish & Richardson P.C., RCE and IDS in Reply to Notice of Allowance of Jan. 28, 2010 in U.S. Appl. No. 10/569,065, filed Mar. 31, 2010, 5 pages.
USPTO Notice of Allowance in U.S. Appl. No. 10/569,065, mailed May 13, 2010, 10 pages.
Fish & Richardson P.C., RCE and IDS in Reply to Notice of Allowance of May 13, 2010 in U.S. Appl. No. 10/569,065, filed Aug. 2, 2010, 4 pages.
USPTO Notice of Allowance in U.S. Appl. No. 10/569,065, mailed Sep. 1, 2010, 9 pages.
Fish & Richardson P.C., RCE and IDS in Reply to Notice of Allowance of Sep. 1, 2010 in U.S. Appl. No. 10/569,065, filed Nov. 8, 2010, 5 pages.
USPTO Notice of Allowance in U.S. Appl. No. 10/569,065, mailed Dec. 2, 2010, 10 pages.
Fish & Richardson P.C., RCE and IDS in Reply to Notice of Allowance of Dec. 2, 2010 in U.S. Appl. No. 10/569,065, filed Feb. 15, 2011, 5 pages.
USPTO Notice of Allowance in U.S. Appl. No. 10/569,065, mailed Apr. 8, 2011, 10 pages.
Fish & Richardson P.C., Response to Notice of Allowance of Apr. 8, 2011 in U.S. Appl. No. 10/569,065, filed Jul. 7, 2011, 2 pages.

USPTO Office Action in U.S. Appl. No. 11/571,707, mailed Mar. 12, 2010, 16 pages.
Fish & Richardson P.C., Amendment in Reply to Action of Mar. 12, 2010 in U.S. Appl. No. 11/571,707, filed Sep. 3, 2010, 14 pages.
USPTO Notice of Allowance in U.S. Appl. No. 11/571,707, mailed Nov. 22, 2010, 12 pages.
Fish & Richardson P.C., Response to Notice of Allowance of Nov. 22, 2010 in U.S. Appl. No. 11/571,707, filed Feb. 18, 2011, 12 pages.
Fish & Richardson P.C., RCE, Petition to Withdraw from Issue, and IDS in U.S. Appl. No. 11/571,707, filed Apr. 13, 2011, 7 pages.
USPTO Decision Granting Petition under 37 CFR 1.313(c)(2) in U.S. Appl. No. 11/571,707, mailed Apr. 14, 2011, 1 page.
USPTO Notice of Allowance in U.S. Appl. No. 11/571,707, mailed May 6, 2011, 11 pages.
Fish & Richardson P.C., Response to Notice of Allowance of May 6, 2011 in U.S. Appl. No. 11/571,707, filed Aug. 3, 2011, 3 pages.
USPTO Notice of Allowance in U.S. Appl. No. 11/574,076, mailed Feb. 3, 2010, 12 pages.
Fish & Richardson P.C., Response to Notice of Allowance of Feb. 3, 2010 in U.S. Appl. No. 11/574,076, filed Apr. 30, 2010, 2 pages.
USPTO Notice of Allowance in U.S. Appl. No. 12/642,244, mailed Sep. 6, 2011, 30 pages.
USPTO Final Office Action in U.S. Appl. No. 11/576,372, mailed May 7, 2010, 7 pages.
Fish & Richardson P.C., Reply to Action of May 7, 2010 in U.S. Appl. No. 11/576,372, filed Aug. 9, 2010, 10 pages.
USPTO Office Action in U.S. Appl. No. 11/576,372, mailed Sep. 2, 2010, 7 pages.
Fish & Richardson P.C., RCE, IDS and Amendment in Reply to Action of Sep. 2, 2010 in U.S. Appl. No. 11/576,372, filed Dec. 2, 2010, 16 pages.
USPTO Office Action in U.S. Appl. No. 11/719,832, mailed Apr. 30, 2010, 20 pages.
Fish & Richardson P.C., Amendment in Reply to Action of Apr. 30, 2010 in U.S. Appl. No. 11/719,832, filed Aug. 30, 2010, 18 pages.
USPTO Office Action in U.S. Appl. No. 11/719,832, mailed Oct. 6, 2010, 12 pages.
Fish & Richardson P.C., RCE, IDS and Amendment in Reply to Action of Oct. 6, 2010 in U.S. Appl. No. 11/719,832, filed Apr. 6, 2011, 27 pages.
USPTO Office Action in U.S. Appl. No. 12/089,275, mailed Jan. 26, 2011, 25 pages.
Fish & Richardson P.C., Amendment in Reply to Action of Jan. 26, 2011 in U.S. Appl. No. 12/089,275, filed Jul. 26, 2011, 19 pages.
Fish & Richardson P.C., RCE and IDS in Reply to Notice of Allowance of Jan. 4, 2010 in U.S. Appl. No. 12/089,276, filed Mar. 31, 2010, 7 pages.
USPTO Notice of Allowance in U.S. Appl. No. 12/089,276, mailed Apr. 21, 2010, 11 pages.
Fish & Richardson P.C., RCE and IDS in Reply to Notice of Allowance of Apr. 21, 2010 in U.S. Appl. No. 12/089,276, filed Jul. 21, 2010, 5 pages.
USPTO Notice of Allowance in U.S. Appl. No. 12/089,276, mailed Sep. 21, 2010, 9 pages.
Fish & Richardson P.C., RCE and IDS in Reply to Notice of Allowance of Sep. 21, 2010 in U.S. Appl. No. 12/089,276, filed Dec. 20, 2010, 6 pages.
USPTO Notice of Allowance in U.S. Appl. No. 12/089,276, mailed Jan. 4, 2011, 11 pages.
Fish & Richardson P.C., RCE and IDS in Reply to Notice of Allowance of Jan. 4, 2011 in U.S. Appl. No. 12/089,276, filed Apr. 4, 2011, 4 pages.
USPTO Notice of Allowance in U.S. Appl. No. 12/089,276, mailed Apr. 12, 2011, 9 pages.
Fish & Richardson P.C., Response to Notice of Allowance of Apr. 12, 2011 in U.S. Appl. No. 12/089,276, filed Jul. 11, 2011, 2 pages.
USPTO Final Office Action in U.S. Appl. No. 12/092,431, mailed May 4, 2010, 13 pages.
Fish & Richardson P.C., RCE, IDS and Amendment in Reply to Action of May 4, 2010 in U.S. Appl. No. 12/092,431, filed Sep. 7, 2010, 16 pages.
USPTO Non-Final Office Action in U.S. Appl. No. 12/092,431, mailed Aug. 17, 2011, 13 pages.
USPTO Final Office Action in U.S. Appl. No. 12/167,513, mailed Apr. 22, 2010, 22 pages.
Fish & Richardson P.C., Amendment in Reply to Action of Apr. 22, 2010 in U.S. Appl. No. 12/167,513, filed Oct. 22, 2010, 22 pages.

* cited by examiner

COMPOUNDS

CROSS-REFERENCE TO RELATED APPLICATIONS

This application is a national phase application under 35 U.S.C. 371 of PCT International Application No. PCT/SE2004/000535, filed Apr. 6, 2004, which claims priority to Swedish Application Serial No. 0301010-5, filed Apr. 7, 2003.

The present invention relates to substituted phenoxyacetic acids as useful pharmaceutical compounds for treating respiratory disorders, pharmaceutical compositions containing them, and processes for their preparation.

EPA 1 170 594 discloses methods for the identification of compounds useful for the treatment of disease states mediated by prostaglandin D2, a ligand for orphan receptor CRTH2. GB 1356834 discloses a series of compounds said to possess anti-inflammatory, analgesic and antipyretic activity. It has been found that certain phenoxyacetic acids are active at the CRTH2 receptor, and as a consequence are expected to be potentially useful for the treatment of various respiratory diseases, including asthma and COPD.

In a first aspect the invention therefore provides a compound of formula (I) or a pharmaceutically acceptable salt or solvate thereof:

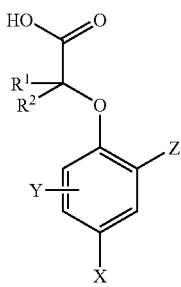

in which:

X is halogen, cyano, nitro, $S(O)_nR^6$ or $C_{1-4}$alkyl which is substituted by one or more halogen atoms;

Y is selected from hydrogen, halogen, CN, nitro, $SO_2R^3$, $OR^4$, $SR^4$, $SOR^3$, $SO_2NR^4R^5$, $CONR^4R^5$, $NR^4R^5$, $NR^6SO_2R^3$, $NR^6CO_2R^6$, $NR^6COR^3$, $C_2$-$C_6$ alkenyl, $C_2$-$C_6$ alkynyl, $C_3$-$C_7$ cycloalkyl or $C_{1-6}$alkyl, the latter four groups being optionally substituted by one or more substituents independently selected from halogen, $OR^6$ and $NR^6R^7$, $S(O)_nR^6$ where n is 0, 1 or 2;

Z is aryl or a ring A, where A is a six membered heterocyclic aromatic ring containing one or more nitrogen atoms or may be a 6,6 or 6,5 fused bicycle containing one or more O, N, S atoms, the aryl or A rings all being optionally substituted by one or more substituents independently selected from from hydrogen, halogen, CN, OH, SH, nitro, $COR^9$, $CO_2R^6$, $SO_2R^9$, $OR^9$, $SR^9$, $SOR^9$, $SO_2NR^{10}R^{11}$, $CONR^{10}R^{11}$, $NR^{10}R^{11}$, $NHSO_2R^9$, $NR^9SO_2R^9$, $NR^6CO_2^6$, $NHCOR^9$, $NR^9COR^9$, $NR^6CONR^4R^5$, $NR^6SO_2NR^4R^5$, aryl, heteroaryl, $C_2$-$C_6$ alkenyl, $C_2$-$C_6$ alkynyl, $C_3$-$C_7$ cycloalkyl or $C_{1-6}$alkyl, the latter four groups being optionally substituted by one or more substituents independently selected from halogen, $C_3$-$C_7$ cycloalkyl, $OR^6$, $NR^6R^7$, $S(O)_nR^6$ (where n is 0, 1 or 2), $CONR^6R^7$, $NR^6COR^7$, $SO_2NR^6R^7$ and $NR^6SO_2R^7$.

$R^1$ and $R^2$ independently represent a hydrogen atom, halogen, $C_2$-$C_6$ alkenyl, $C_2$-$C_6$ alkynyl, $C_3$-$C_7$ cycloalkyl or a $C_{1-6}$alkyl group, the latter four groups being optionally substituted by one or more substituents independently selected from halogen, $C_3$-$C_7$ cycloalkyl, $NR^6R^7$, $OR^6$, $S(O)_nR^6$ (where n is 0, 1 or 2);

or $R^1$ and $R^2$ together can form a 3-8 membered ring optionally containing one or more atoms selected from O, S, $NR^6$ and itself optionally substituted by one or more $C_1$-$C_3$ alkyl or halogen;

$R^3$ represents $C_3$-$C_7$ cycloalkyl or $C_{1-6}$alkyl which may be optionally substituted by one or more substituents independently selected from halogen, $C_3$-$C_7$ cycloalkyl, $OR^6$ and $NR^6R^7$, $S(O)_nR^6$ (where n=0, 1 or 2), $CONR^6R^7$, $NR^6COR^7$, $SO_2NR^6R^7$ and $NR^6SO_2R^7$;

$R^4$ and $R^5$ independently represent hydrogen, $C_3$-$C_7$ cycloalkyl or $C_{1-6}$alkyl, the latter two groups being optionally substituted by one or more substituents independently selected from halogen, $C_3$-$C_7$ cycloalkyl, $OR^6$ and $NR^6R^7$, $S(O)_nR^6$ (where n=0, 1 or 2), $CONR^6R^7$, $NR^6COR^7$, $SO_2NR^6R^7$ and $NR^6SO_2R^7$;

or $R^4$ and $R^5$ together with the nitrogen atom to which they are attached can form a 3-8 membered saturated heterocylic ring optionally containing one or more atoms selected from O, $S(O)_n$ (where n=0, 1 or 2), $NR^8$, and itself optionally substituted by halogen or $C_{1-3}$alkyl;

$R^6$ and $R^7$ independently represents a hydrogen atom or $C_1$-$C_6$ alkyl;

$R^8$ is hydrogen, $C_{1-4}$ alkyl, $-COC_1$-$C_4$ alkyl, $CO_2C_1$-$C_4$alkyl or $CONR^6C_1$-$C_4$alkyl;

$R^9$ represents aryl, heteroaryl, $C_3$-$C_7$ cycloalkyl or $C_{1-6}$alkyl, the latter two groups may be optionally substituted by one or more substituents independently selected from halogen, $C_3$-$C_7$ cycloalkyl, aryl, heteroaryl $OR^6$ and $NR^6R^7$, $S(O)_nR^6$ (where n=0, 1 or 2), $CONR^6R^7$, $NR^6COR^7$, $SO_2NR^6R^7$ and $NR^6SO_2^7$;

$R^{10}$ and $R^{11}$ independently represent aryl or heteroaryl, hydrogen, $C_3$-$C_7$ cycloalkyl or $C_{1-6}$alkyl, the latter two groups being optionally substituted by one or more substituents independently selected from halogen, $C_3$-$C_7$ cycloalkyl, aryl, heteroaryl, $OR^6$ and $NR^6R^7$, $S(O)_nR^6$ (where n=0, 1 or 2), $CONR^6R^7$, $NR^6COR^7$, $SO_2NR^6R^7$ and $NR^6SO_2R^7$;

or $R^{10}$ and $R^{11}$ together with the nitrogen atom to which they are attached can form a 3-8 membered saturated heterocyclic ring optionally containing one or more atoms selected from O, $S(O)_n$ (where n=0, 1 or 2), $NR^8$, and itself optionally substituted by halogen or $C_1$-$C_3$ alkyl.

Examples of aryl include phenyl and naphthyl.

Heteroaryl is defined as a 5-7 member aromatic ring or can be 6,6- or 6,5-fused bicyclic ring optionally containing one or more heteroatoms selected from N, S and O. The bicyclic ring may be linked through carbon or nitrogen and may be attached through the 5 or 6 membered ring and can be fully or partially saturated.

Examples include pyridine, pyrimidine, thiazole, oxazole, pyrazole, imidazole, furan, isoxazole, pyrrole, isothiazole and azulene, naphthyl, indene, quinoline, isoquinoline, indole, indolizine, benzo[b]furan, benzo[b]thiophene, 1H-indazole, benzimidazole, benzthiazole, benzoxazole, purine, 4H-quinolizine, cinnoline, phthalazine, quinazoline, quinoxaline, 1,8-naphthyridine, pteridine, quinolone and 1,2-methylenedioxy benzene.

Aryl or heteroaryl groups can be optionally substituted by one or more substituents independently selected from hydrogen, halogen, CN, OH, SH, nitro, $CO_2R^6$, $SO_2R^9$, $OR^9$, $SR^9$, $SOR^9$, $SO_2NR^{10}R^{11}$, $CONR^{10}R^{11}$, $NR^{10}R^{11}$, $NHSO_2R^9$, $NR^9SO_2R^9$, $NR^6CO_2R^6$, $NHCOR^9$, $NR^9COR^9$, aryl, heteroaryl, $C_2$-$C_6$ alkenyl, $C_2$-$C_6$ alkyl, $C_3$-$C_7$ cycloalkyl or $C_{1-6}$alkyl, the latter four groups being optionally substituted by one or more substituents independently selected from halogen, $C_3$-$C_7$ cycloalkyl, $OR^6$, $NR^6R^7$, $S(O)_nR^6$ (where n is 0, 1 or 2), $CONR^6R^7$, $NR^6COR^7$, $SO_2NR^6R^7$ and $NR^6SO_2R^7$. Substituents can be present at any suitable position, including appropriate substituents on nitrogen atoms.

The group A is a six membered heterocyclic ring containing one or more nitrogen atoms or may be a 6,6 or 6,5 fused bicycle containing one or more O, N, S atoms. Examples of suitable rings include pyridine, pyrimidine, pyrazine, pyridazine, indole, quinoline, isoquinoline, benzimidazole, benzthiazole, benzofuran, benzoxazole, benzthiophene, phthalazine and quinazoline.

In the context of the present specification, unless otherwise indicated, an alkyl or alkenyl group or an alkyl or alkenyl moiety in a substituent group may be linear or branched.

Heterocyclic rings as defined for $R^4$, $R^5$ and $R^{10}$ and $R^{11}$ means saturated heterocycles, examples include morpholine, azetidine, pyrrolidine, piperidine and piperazine. Substituents can be present on carbon and appropriate nitrogen atoms of said rings.

Preferably X is trifluoromethyl, nitro, cyano or halogen. More preferably X is trifluoromethyl, nitro, cyano, chloro or fluoro, even more preferably X is trifluoromethyl, chloro or fluoro. Most preferably X is trifluoromethyl or chloro.

Preferably Y is hydrogen, halogen or $C_{1-3}$alkyl. More preferably Y is hydrogen, fluoro or methyl. Most preferably Y is hydrogen.

Preferably Z is phenyl, pyridinyl, pyrimidyl, naphthyl, quinolyl, benzo[b]thienyl or benzofuranyl each optionally substituted as defined above, more preferably phenyl optionally substituted as defined above. Preferred substituents for all Z groups include those substituents exemplified herein, in particular halogen, $C_{1-3}$alkyl, cyano, $SO_2R^9$, $OR^9$, $SR^9$, $CO_2R^6$, $NHSO_2R^9$, $NR^9SO_2R^9$ and $SO_2NR^{10}R^{11}$.

More preferably when Z is phenyl it is optionally substituted by one to three, preferably one or two, substituents selected from SEt, $SO_2Me$, $SO_2Et$, chloro, fluoro, cyano, methoxy, propoxy, $CO_2H$, methyl, ethyl, propyl, butyl, amino, hydroxyl, NHCONHEt, NHCONHMe, NHCONHPr, NHCONH-cyclopropyl, $CONH_2$, $SO_2NH_2$, $OCF_3$, COMe, $CO_2Me$, nitro, phenyl, $SCF_3$, 1-pyrrolidinylsulphonyl, dimethylaminosulphonyl, ((phenylmethy)lamino)sulphonyl, [(2,2,2-trifluoroethyl)]amino]sulphonyl, [(5-methyl-2-thiazolyl)amino]sulphonyl, (phenylamino)sulphonyl, (diethylamino)sulphonyl, (cyclopropylamino)sulphonyl, aminosulphonyl, (methylamino)sulphonyl, (4-methyl-1-piperazinyl)sulphonyl, $NHCO_2Me$, (dimethylamino)sulphonyl, 4-morpholinylsulphonyl, 1-azetidinylsulphonyl, and 1-pyrrolidinylcarbonyl.

More preferably when Z is pyridyl it is optionally substituted by one or two groups selected from $SO_2NH_2$, methyl, amino, chloro and $NMeSO_2Me$.

More preferably when Z is pyrimidine it is optionally substituted by one or two groups selected from amino, methyl, morpholinyl, dimethylamino, methylamino, benzylamino, piperidine, $NMeSO_2Me$, (methylsulphonul)(benzyl)amino, (ethylsulphonul)(benzyl)amino, acetyl(phenylmethyl)amino, 5-methyl-1,1-dioxido-1,2,5-thiadiazolidin-2-yl, 1,1-dioxido-2-isothiazolidinyl, 3-hydroxy-1-azetidinyl, 4-methyl-1-piperazinyl, 1-pyrrolidinyl and $NHSO_2NMe_2$.

When Z is naphthyl it is preferably substituted with methoxy.

When Z is quinolyl, benzo[b]thienyl or benzofuranyl these groups are preferably unsubstituted.

Preferably $R^1$ and $R^2$ are independently hydrogen or $C_{1-3}$ alkyl. More preferably both $R^1$ and $R^2$ are hydrogen or one is hydrogen and the other is methyl or ethyl or both are methyl. Most preferably both $R^1$ and $R^2$ are hydrogen.

Preferred compounds of the invention include those exemplified herein both in free base form as well as pharmaceutically acceptable salts and solvates thereof.

Certain compounds of formula (I) are capable of existing in stereoisomeric forms. It will be understood that the invention encompasses all geometric and optical isomers of the compounds of formula (I) and mixtures thereof including racemates. Tautomers and mixtures thereof also form an aspect of the present invention.

The compound of formula (I) above may be converted to a pharmaceutically acceptable salt or solvate thereof, preferably a basic addition salt such as sodium, potassium, calcium, aluminium, lithium, magnesium, zinc, benzathine, chloroprocaine, choline, diethanolamine, ethanolamine, ethyldiamine, meglumine, tromethamine or procaine, or an acid addition salt such as a hydrochloride, hydrobromide, phosphate, acetate, fumarate, maleate, tartrate, citrate, oxalate, methanesulphonate or p-toluenesulphonate.

It will be appreciated by those skilled in the art that in the processes of the present invention certain functional groups in the starting reagents or intermediate compound may need to be protected by protecting groups. Thus, the preparation of the compound of formula (I) may involve, at an appropriate stage, the removal of one or more protecting groups. The protection and deprotection of functional groups is fully described in 'Protective Groups in Organic Chemistry', edited by J. W. F. McOmie, Plenum Press (1973), and 'Protective Groups in Organic Synthesis', 3rd edition, T. W. Greene & P. G. M. Wuts, Wiley-Interscience (1999).

Compounds of formula (I) can be prepared by reaction of a compound of formula (II):

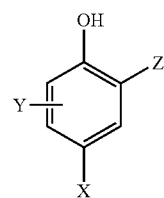

(II)

in which X, Y and Z are as defined in formula (I) or are protected derivatives thereof, with a compound of formula (III):

$$L-CR^1R^2CO_2R^{12} \qquad (III)$$

Where $R^1$ and $R^2$ are as defined in formula (I) or are protected derivatives thereof, $R^{12}$ is H is or $C_1$-$C_{10}$ alkyl group and L is a leaving group, and optionally thereafter in any order:

removing any protecting group
    hydrolysing the ester group $R^{12}$ to the corresponding acid
    oxidation of sulfides to sulphoxides or sulphones
    forming a pharmaceutically acceptable salt.

The reaction can be carried out in a suitable solvent such as DMF using a base such as potassium carbonate or the like. Suitable groups $R^{12}$ include $C_{1-6}$ alkyl groups such as methyl, ethyl or tert-butyl. Suitable L is a leaving group such as halo, in particular chlorine or bromine. L may also be hydroxy so that a Mitsunobu reaction may be performed with compound (II) using for example triphenylphosphine and diethyl azodicarboxylate.

Hydrolysis of the ester group $R^{12}$ can be carried out using routine procedures, for example treatment of methyl and ethyl esters with aqueous sodium hydroxide, and treatment of tert-butyl esters with acids such as trifluoroacetic acid.

Compounds of formula (II) can be prepared by reaction of a compound of formula (IV) with a compound of formula (V) via a Suzuki coupling reaction followed by deprotection of group $R^{13}$ when $R^{13}$ is not equal to H:

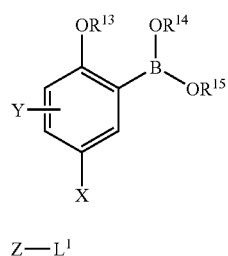
(IV)

Z—L¹ (V)

in which X, Y and Z are as defined in formula (I) or are protected derivatives thereof, $R^{13}$ is H or a suitable protecting group, for example benzyl, $L^1$ is iodide, bromide, chloride or triflate and $R^{14}$ and $R^{15}$ are H or $C_1$-$C_6$ alkyl groups or $R^{14}$ and $R^{15}$ together can form a 5 or 6 membered ring optionally substituted by one or more $C_1$-$C_3$ alkyl.

The reaction can be carried out in a suitable solvent such as dioxane using a palladium catalyst such as [1,1-bis(diphenylphosphino)ferrocene]dichloropalladium and a base such as cesium fluoride, preferably at elevated temperatures.

Compounds of formula (IV) can be prepared from a compound of formula (VI) by formation of an organometallic (VII) followed by reaction with a borate ester, as outlined in Scheme I.

Scheme I

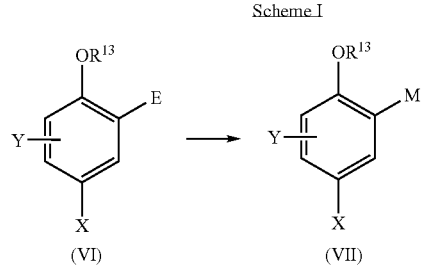

in which X, Y are as defined in formula (I) or are protected derivatives thereof, $R^{13}$ is as defined in formula (IV), E is hydrogen or halogen and M is a metal such as Na or Li. For example when $R^{13}$ is benzyl and E is bromine, butyl lithium can be used to form the intermediate (VII) where M=Li. The reaction is performed at −78° C. in diethylether, then quenched with a borate ester such as trimethylborate.

Compound of formula (IV) may also be prepared by a palladium catalysed coupling of compounds of formula (VIII) with a suitable boronic ester, for example (IX) or (X).

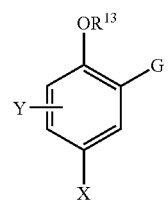
(VIII)

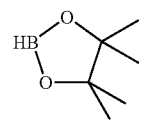
(IX)

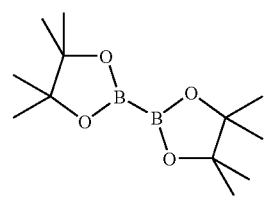
(X)

in which X, Y and $R^{13}$ are as defined above and G is halogen or triflate

Compounds of formula (II) may also be prepared by reaction of a compound of formula (XI) with a compound of formula (XII) using Suzuki coupling methodology.

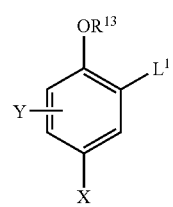
(XI)

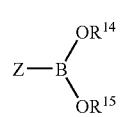
(XII)

in which X, Y, Z, $R^{13}$, $L^1$, $R^{14}$ and $R^{15}$ are as defined above and compounds of formula (XI) and (XII) can be made using the same methodology as above.

Compounds of formula (II), where Z=heteroaryl may also be prepared by ring synthesis, for example a compound of formula (XIII) may be formed by reaction of a compound of formula (XIV) with a compound of formula (XV).

X, Y and $R^{13}$ are as defined above and $R^{16}$ is as defined as a substituent on Z as defined in formula (I) or are protected derivatives thereof. The reaction can be carried out in a solvent such as ethanol under reflux, and a base such as sodium ethoxide can be used if compound of formula (XV) is a salt

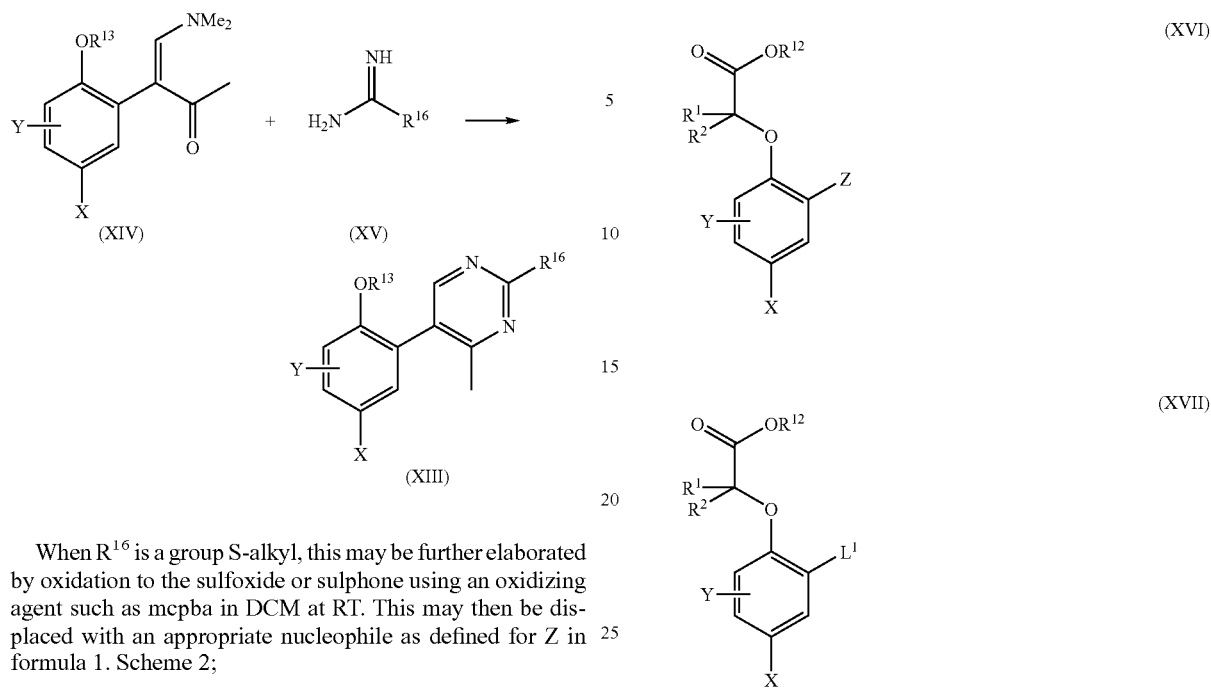

When R$^{16}$ is a group S-alkyl, this may be further elaborated by oxidation to the sulfoxide or sulphone using an oxidizing agent such as mcpba in DCM at RT. This may then be displaced with an appropriate nucleophile as defined for Z in formula 1. Scheme 2;

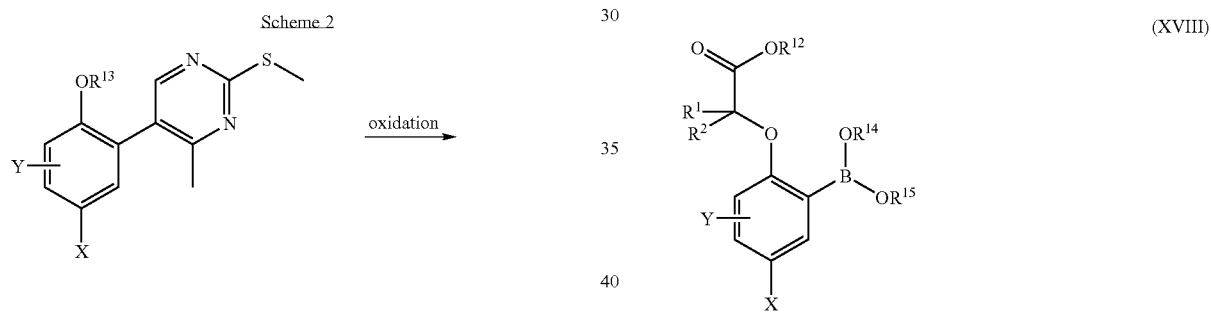

Compounds of formula (I) may also be prepared by reaction of a compound of formula (XVIII) in which in which X, Y, R$^1$, R$^2$, R$^{12}$, R$^{14}$ and R$^{15}$ are as defined above with a compound of formula (V) using Suzuki coupling method as defined above.

A compound of formula (XVIII) may be prepared by method A or B

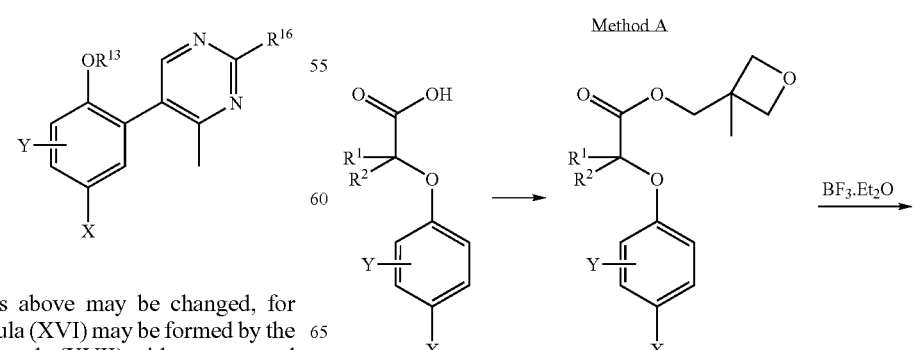

The sequence of the steps above may be changed, for example a compound of formula (XVI) may be formed by the reaction of a compound of formula (XVII) with a compound of formula (XII) using a Suzuki coupling.

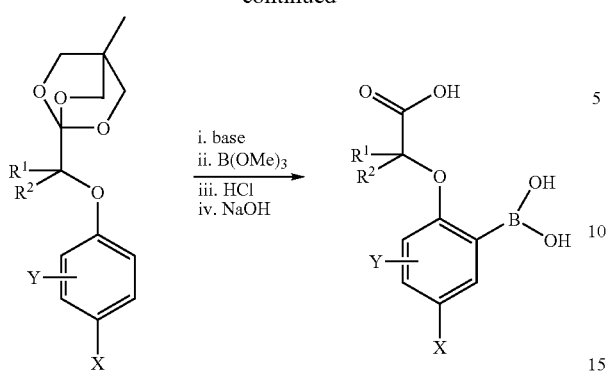
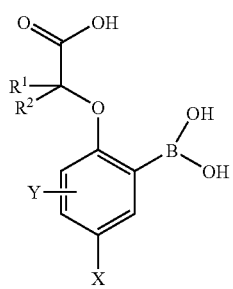

The acid was first converted to the acid chloride, using for example oxalylchloride in DCM at RT, then reacted with 3-methyl-3-oxetanemethanol in the presence of a base such as triethylamine to give the ester. The oxetane ester is the rearranged to the OBO ester using boron trifluoride diethyletherate in DCM at −78° C. to RT. Deprotonation with a base such as sec-butyl lithium at low temperature followed by quenching with trimethylborate gave the protected diacid which was then deprotected using HCl then sodium hydroxide

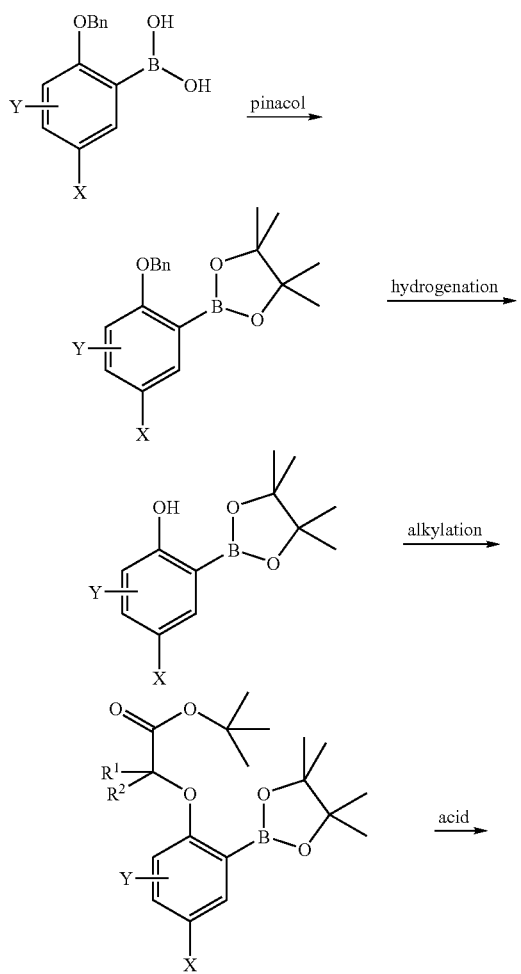

A compound of formula (IV) where $R^{13}$=Bn and $R^{14}$ and $R^{15}$=H and pinacol can bestirred at RT in a suitable solvent such as diethylether to give the boronate ester. The benzyl group may be removed by hydrogenation at RT using palladium on carbon as catalyst then alkylated with a compound of formula (III) using a base or mitsunobu conditions. Treatment with acid such as HCl or trifluoroacetic acid then removes the protecting groups.

In a further aspect, the present invention provides the use of a compound of formula (I), a prodrug, pharmaceutically acceptable salt or solvate thereof for use in therapy.

The compounds of formula (I) have activity as pharmaceuticals, in particular as modulators of CRTh2 receptor activity, and may be used in the treatment (therapeutic or prophylactic) of conditions/diseases in human and non-human animals which are exacerbated or caused by excessive or unregulated production of $PGD_2$ and its metabolites. Examples of such conditions/diseases include:

(1) (the respiratory tract) obstructive airways diseases including: asthma (such as bronchial, allergic, intrinsic, extrinsic and dust asthma particularly chronic or inveterate asthma (e.g. late asthma airways hyper-responsiveness)); chronic obstructive pulmonary disease (COPD) (such as irreversible COPD); bronchitis (including eosinophilic bronchitis); acute, allergic, atrophic rhinitis or chronic rhinitis (such as rhinitis caseosa, hypertrophic rhinitis, rhinitis purulenta, rhinitis sicca), rhinitis medicamentosa, membranous rhinitis (including croupous, fibrinous and pseudomembranous rhinitis), scrofoulous rhinitis, perennial allergic rhinitis, easonal rhinitis (including rhinitis nervosa (hay fever) and vasomotor rhinitis); nasal polyposis; sarcoidosis; farmer's lung and related diseases; fibroid lung; idiopathic interstitial pneumonia; cystic fibrosis; antitussive activity; treatment of chronic cough associated with inflammation or iatrogenic induced;

(2) (bone and joints) arthrides including rheumatic, infectious, autoimmune, seronegative, spondyloarthropathies (such as ankylosing spondylitis, psoriatic arthritis and Reiter's disease), Behcet's disease, Sjogren's syndrome and systemic sclerosis;

(3) (skin and eyes) psoriasis, atopical dermatitis, contact dermatitis, other eczmatous dermitides, seborrhoetic dermatitis, Lichen planus, Pemphigus, bullous Pemphigus, Epidermolysis bullosa, urticaria, angiodermas, vasculitides, erythemas, cutaneous eosinophilias, chronic skin ulcers, uveitis, Alopecia areatacorneal ulcer and vernal conjunctivitis;

(4) (gastrointestinal tract) Coeliac disease, proctitis, eosinopilic gastro-enteritis, mastocytosis, Crohn's disease, ulcerative colitis, irritable bowel disease; food-related allergies which have effects remote from the gut, (such as migraine, rhinitis and eczema);

(5) (central and peripheral nervous system) Neurodegenerative diseases and dementia disorders (such as Alzheimer's disease, amyotrophic lateral sclerosis and other motor neuron diseases, Creutzfeldt-Jacob's disease and other prion diseases, HIV encephalopathy (AIDS dementia complex), Huntington's disease, frontotemporal dementia, Lewy body dementia and vascular dementia), polyneuropathies (such as Guillain-Barré syndrome, chronic inflammatory demyelinating polyradiculoneuropathy, multifocal motor neuropathy), plexopathies, CNS demyelination (such as multiple sclerosis, acute disseminated/haemorrhagic encephalomyelitis, and subacute sclerosing panencephalitis), neuromuscular disorders (such as myasthenia gravis and Lambert-Eaton syndrome), spinal diorders (such as tropical spastic paraparesis, and stiff-man syndrome), paraneoplastic syndromes (such as cerebellar degeneration and encephalomyelitis), CNS trauma, migraine and stroke.

(6) (other tissues and systemic disease) atherosclerosis, acquired Immunodeficiency Syndrome (AIDS), lupus erythematosus; systemic lupus, erythematosus; Hashimoto's thyroiditis, type I diabetes, nephrotic syndrome, eosinophilia fascitis, hyper IgE syndrome, lepromatous leprosy, idiopathic thrombocytopenia pupura; post-operative adhesions, sepsis and ischemic/reperfusion injury in the heart, brain, peripheral limbs hepatitis (alcoholic, steatohepatitis and chronic viral), glomerulonephritis, renal impairment, chronic renal failure and other organs (7) (allograft rejection) acute and chronic following, for example, transplantation of kidney, heart, liver, lung, bone marrow, skin and cornea; and chronic graft versus host disease;

(8) Diseases associated with raised levels of $PGD_2$ or its metabolites.

(1) (respiratory tract)—obstructive diseases of the airways including: asthma, including bronchial, allergic, intrinsic, extrinsic, exercise-induced, drug-induced (including aspirin and NSAID-induced) and dust-induced asthma, both intermittent and persistent and of all severities, and other causes of airway hyper-responsiveness; chronic obstructive pulmonary disease (COPD); bronchitis, including infectious and eosinophilic bronchitis; emphysema; bronchiectasis; cystic fibrosis; sarcoidosis; farmer's lung and related diseases; hypersensitivity pneumonitis; lung fibrosis, including cryptogenic fibrosing alveolitis, idiopathic interstitial pneumonias, fibrosis complicating anti-neoplastic therapy and chronic infection, including tuberculosis and aspergillosis and other fungal infections; complications of lung transplantation; vasculitic and thrombotic disorders of the lung vasculature, and pulmonary hypertension; antitussive activity including treatment of chronic cough associated with inflammatory and secretory conditions of the airways, and iatrogenic cough; acute and chronic rhinitis including rhinitis medicamentosa, and vasomotor rhinitis; perennial and seasonal allergic rhinitis including rhinitis nervosa (hay fever); nasal polyposis; acute viral infection including the common cold, and infection due to respiratory syncytial virus, influenza, coronavirus (including SARS) and adenovirus.

(2) (bone and joints) arthritis associated with or including osteoarthritis/osteoarthrosis, both primary and secondary to e.g. congenital hip dysplasia; cervical and lumbar spondylitis, and low back and neck pain; rheumatoid arthritis and Still's disease; seronegative spondyloarthropathies including ankylosing spondylitis, psoriatic arthritis, reactive arthritis and undifferentiated spondarthropathy; septic arthritis and other infection-related arthopathies and bone disorders such as tuberculosis, including-Potts' disease and Poncet's syndrome; acute and chronic crystal-induced synovitis including urate gout, calcium pyrophosphate deposition disease, and calcium apatite related tendon, bursal and synovial inflammation; Behcet's disease; primary and secondary Sjogren's syndrome; systemic sclerosis and limited scleroderma; systemic lupus erythematosus, mixed connective tissue disease, and undifferentiated connective tissue disease; inflammatory myopathies including dermatomyositits and polymyositis; polymalgia rheumatica; juvenile arthritis including idiopathic inflammatory arthritides of whatever joint distribution and associated syndromes, and rheumatic fever and its systemic complications; vasculitides including giant cell arteritis, Takayasu's arteritis, Churg-Strauss syndrome, polyarteritis nodosa, microscopic polyarteritis, and vasculitides associated with viral infection, hypersensitivity reactions, cryoglobulins, and paraproteins; low back pain; Familial Mediterranean fever, Muckle-Wells syndrome, and Familial Hibernian Fever, Kikuchi disease; drug-induced arthalgias, tendonititides, and myopathies.

(3) (skin) psoriasis, atopic dermatitis, contact dermatitis or other eczematous dermatoses, and delayed-type hypersensitivity reactions; phyto- and photodermatitis; seborrhoeic dermatitis, dermatitis herpetiformis, lichen planus, lichen sclerosus et atrophica, pyoderma gangrenosum, skin sarcoid, discoid lupus erythematosus, pemphigus, pemphigoid, epidermolysis bullosa, urticaria, angioedema, vasculitides, toxic erythemas, cutaneous eosinophilias, alopecia areata, male-pattern baldness, Sweet's syndrome, Weber-Christian syndrome, erythema multiforme; cellulitis, both infective and non-infective; panniculitis; cutaneous lymphomas, non-melanoma skin cancer and other dysplastic lesions; drug-induced disorders including fixed drug eruptions.

(4) (eyes) blepharitis; conjunctivitis, including perennial and vernal allergic conjunctivitis; iritis; anterior and posterior uveitis; choroiditis; autoimmune; degenerative or inflammatory disorders affecting the retina; ophthalmitis including sympathetic ophthalmitis; sarcoidosis; infections including viral, fungal, and bacterial.

(5) (gastrointestinal tract) glossitis, gingivitis, periodontitis; oesophagitis, including reflux; eosinophilic gastroenteritis, mastocytosis, Crohn's disease, colitis including ulcerative colitis, proctitis, pruritis ani; coeliac disease, irritable bowel syndrome, and food-related allergies which may have effects remote from the gut (for example migraine, rhinitis or eczema).

(6) (abdominal) hepatitis, including autoimmune, alcoholic and viral; fibrosis and cirrhosis of the liver; cholecystitis; pancreatitis, both acute and chronic.

(7) (genitourinary) nephritis including interstitial and glomerulonephritis; nephrotic syndrome; cystitis including acute and chronic (interstitial) cystitis and Hunner's ulcer, acute and chronic urethritis, prostatitis, epididymitis, oophoritis and salpingitis; vulvo-vaginitis; Peyronie's disease; erectile dysfunction (both male and female).

(8) (Allograft rejection) acute and chronic following, for example, transplantation of kidney, heart, liver, lung, bone marrow, skin or cornea or following blood transfusion; or chronic graft versus host disease;

(9) (CNS) Alzheimer's disease and other dementing disorders including CJD and nvCJD; amyloidosis; multiple sclerosis and other demyelinating syndromes; cerebral atherosclerosis and vasculitis; temporal arteritis; myasthenia gravis; acute and chronic pain (acute, intermittent or persistent, whether of central or peripheral origin) including visceral pain, headache, migraine, trigeminal neuralgia, a typical facial pain, joint and bone pain, pain arising from cancer and tumor invasion, neuropathic pain syndromes including diabetic, post-herpetic, and HIV-associated neuropathies; neurosarcoidosis; central and peripheral nervous system complications of malignant, infectious or autoimmune processes.

(10) Other auto-immune and allergic disorders including Hashimoto's thyroiditis, Graves' disease, Addison's disease, diabetes mellitus, idiopathic thrombocytopaenic purpura, eosinophilic fasciitis, hyper-IgE syndrome, antiphospholipid syndrome.

(11) Other disorders with an inflammatory or immunological component; including acquired immune deficiency syndrome (AIDS), leprosy, Sezary syndrome, and paraneoplastic syndromes.

(12) (Cardiovascular); atherosclerosis, affecting the coronary and peripheral circulation; pericarditis; myocarditis, inflammatory and auto-immune cardiomyopathies including myocardial sarcoid; ischaemic reperfusion injuries; endocarditis, valvulitis, and aortitis including infective (e.g. syphilitic); vasculitides; disorders of the proximal and peripheral veins including phlebitis and thrombosis, including deep vein thrombosis and complications of varicose veins.

(13) (Oncology) treatment of common cancers including prostate, breast, lung, ovarian, pancreatic, bowel and colon, stomach, skin and brain tumors and malignancies affecting the bone marrow (including the leukaemias) and lymphoproliferative systems, such as Hodgkin's and non-Hodgkin's lymphoma; including the prevention and treatment of metastatic disease and tumour recurrences, and paraneoplastic syndromes.

(14) Diseases associated with raised levels of $PGD_2$ or its metabolites.

Thus, the present invention provides a compound of formula (I), or a pharmaceutically-acceptable salt or solvate thereof, as hereinbefore defined for use in therapy.

Preferably the compounds of the invention are used to treat diseases in which the chemokine receptor belongs to the CRTh2 receptor subfamily.

Particular conditions which can be treated with the compounds of the invention are asthma, rhinitis and other diseases in which raised levels of $PGD_2$ or its metabolites. It is preferred that the compounds of the invention are used to treat asthma.

In a further aspect, the present invention provides the use of a compound of formula (I), or a pharmaceutically acceptable salt or solvate thereof, as hereinbefore defined in the manufacture of a medicament for use in therapy.

In a further aspect, the present invention provides the use of a compound or formula (I), or a pharmaceutically acceptable salt or solvate thereof, as hereinbefore defined in the manufacture of a medicament for use in therapy in combination with drugs used to treat is asthma and rhinitis (such as inhaled and oral steroids, inhaled β2-receptor agonists and oral leukotriene receptor antagonists).

The invention further relates to combination therapies wherein a compound of formula (1) or a pharmaceutically acceptable salt, solvate or in vivo hydrolysable ester thereof, or a pharmaceutical composition or formulation comprising a compound of formula (1) is administered concurrently or sequentially or as a combined preparation with another therapeutic agent or agents, for the treatment of one or more of the conditions listed.

In particular, for the treatment of the inflammatory diseases rheumatoid arthritis, psoriasis, inflammatory bowel disease, COPD, asthma and allergic rhinitis the compounds of the invention may be combined with agents such as tumour necrosis factor alpha (TNF-α) inhibitors such as anti-TNF monoclonal antibodies (for example Remicade, CDP-870 and adalimumab) and TNF receptor immunoglobulin molecules (such as Enbrel); non-selective cyclo-oxygenase (COX)-1/COX-2 inhibitors whether applied topically or systemically (such as piroxicam, diclofenac, propionic acids such as naproxen, flubiprofen, fenoprofen, ketoprofen and ibuprofen, fenamates such as mefenamic acid, indomethacin, sulindac, azapropazone, pyrazolones such as phenylbutazone, salicylates such as aspirin), COX-2 inhibitors (such as meloxicam, celecoxib, rofecoxib, valdecoxib, lumarocoxib, parecoxib and etoricoxib); glucocorticosteroids (whether administered by topical, oral, intramuscular, intravenous, or intra-articular routes); methotrexate, lefunomide; hydroxychloroquine, d-penicillamine, auranofin or other parenteral or oral gold preparations.

The present invention still further relates to the combination of a compound of the invention together with a leukotriene biosynthesis inhibitor, 5-lipoxygenase (5-LO) inhibitor or 5-lipoxygenase activating protein (FLAP) antagonist such as; zileuton; ABT-761; fenleuton; tepoxalin; Abbott-79175; Abbott-85761; N-(5-substituted)-thiophene-2-alkylsulfonamides; 2,6-di-tert-butylphenol hydrazones; methoxytetrahydropyrans such as Zeneca ZD-2138; the compound SB-210661; pyridinyl-substituted 2-cyanonaphthalene compounds such as L-739,010; 2-cyanoquinoline compounds such as L-746,530; indole and quinoline compounds such as MK-591, MK-886, and BAY×1005.

The present invention still further relates to the combination of a compound of the invention together with a receptor antagonist for leukotrienes(LT)B4, LTC4, LTD4, and LTE4. selected from the group consisting of the phenothiazin-3-1s such as L-651,392; amidino compounds such as CGS-25019c; benzoxalamines such as ontazolast; benzenecarboximidamides such as BIIL 284/260; and compounds such as zafirlukast, ablukast, montelukast, pranlukast, verlukast (MK-679), RG-12525, Ro-245913, iralukast (CGP 45715A), and BAY×7195.

The present invention still further relates to the combination of a compound of the invention together with a phosphodiesterase (PDE) inhibitor such as the methylxanthanines including theophylline and aminophylline; and selective PDE isoenzyme inhibitors including PDE4 inhibitors and inhibitors of the isoform PDE4D, and inhibitors of PDE5.

The present invention still further relates to the combination of a compound of the invention together with histamine type 1 receptor antagonists such as cetirizine, loratadine, desloratadine, fexofenadine, acrivastine, terfenadine, astemizole, azelastine, levocabastine, chlorpheniramine, promethazine, cyclizine, and mizolastine applied orally, topically or parenterally.

The present invention still further relates to the combination of a compound of the invention together with a gastroprotective histamine type 2 receptor antagonist.

The present invention still further relates to the combination of a compound of the invention with antagonists of the histamine type 4 receptor.

The present invention still further relates to the combination of a compound of the invention together with an alpha- 1/alpha-2 adrenoceptor agonist vasoconstrictor sympathomimetic agent, such as propylhexedrine, phenylephrine, phenylpropanolamine, ephedrine, pseudoephedrine, naphazoline hydrochloride, oxymetazoline hydrochloride, tetrahydrozoline hydrochloride, xylometazoline hydrochloride, tramazoline hydrochloride, and ethylnorepinephrine hydrochloride.

The present invention still further relates to the combination of a compound of the invention together with anticholinergic agents including muscarinic receptor (M1, M2, and M3) antagonists such as atropine, hyoscine, glycpyrrrolate, ipratropium bromide; tiotropium bromide; oxitropium bromide; pirenzepine; and telenzepine.

The present invention still further relates to the combination of a compound of the invention together with a beta-adrenoceptor agonist (including beta receptor subtypes 1-4) such as isoprenaline, salbutamol, formoterol, salmeterol, terbutaline, orciprenaline, bitolterol mesylate, and pirbuterol.

The present invention still further relates to the combination of a compound of the invention together with a chromone, including sodium cromoglycate and nedocromil sodium.

The present invention still further relates to the combination of a compound of the invention together with an insulin-like growth factor type I (IGF-1) mimetic.

The present invention still further relates to the combination of a compound of the invention together with an inhaled glucocorticoid, such as flunisolide, triamcinolone acetonide, beclomethasone dipropionate, budesonide, fluticasone propionate, ciclesonide, and mometasone furoate.

The present invention still further relates to the combination of a compound of the invention together with an inhibitor of matrix metalloproteases (MMPs), i.e., the stromelysins, the collagenases, and the gelatinases, as well as aggrecanase; especially collagenase-1 (MMP-1), collagenase-2 (MMP-8), collagenase-3 (−13), stromelysin-1 (MMP-3), stromelysin-2 (MMP-10), and stromelysin-3 (MMP-11) and MM-9 and MMP-12.

The present invention still further relates to the combination of a compound of the invention together with modulators of chemokine receptor function such as antagonists of CCR1, CCR2, CCR2A, CCR2B, CCR3, CCR4, CCR5, CCR6, CCR7, CCR8, CCR9, CCR10 and CCR11 (for the C—C family); CXCR1, CXCR2, CXCR3, CXCR4 and CXCR5 (for the C—X—C family) and $CX_3CR1$ for the $C-X_3-C$ family.

The present invention still further relates to the combination of a compound of the invention together with a cytokine or modulator of cytokine function, including alpha-, beta-, and gamma-interferon; interleukins (IL) including IL1 to 15, and interleukin antagonists or inhibitors, including agents which act on cytokine signalling pathways.

The present invention still further relates to the combination of a compound of the invention together with an immunoglobulin (Ig) or Ig preparation or an antagonist or antibody modulating Ig function such as anti-IgE (omalizumab).

The present invention still further relates to the combination of a compound of the invention together with other systemic or topically-applied anti-inflammatory agents including thalidomide and derivatives, retinoids, dithranol, and calcipotriol.

The present invention still further relates to the combination of a compound of the invention together with an antibacterial agent including penicillin derivatives, tetracyclines, macrolides, beta-lactams, flouroquinolones, and inhaled aminoglycosides; and antiviral agents including acyclovir, famciclovir, valaciclovir, ganciclovir, cidofovir; amantadine, rimantadine; ribavirin; zanamavir and oseltamavir; protease inhibitors such as indinavir, nelfinavir, ritonavir, and saquinavir; nucleoside reverse transcriptase inhibitors such as didanosine, lamivudine, stavudine, zalcitabine, zidovudine; non-nucleoside reverse transcriptase inhibitors such as nevirapine, efavirenz.

The present invention still further relates to the combination of a compound of the invention together with cardiovascular agents such as calcium channel blockers, beta-adrenoceptor blockers, angiotensin-converting enzyme (ACE) inhibitors, angiotensin-2 receptor antagonists; lipid lowering agents such as statins, and fibrates; modulators of blood cell morphology such as pentoxyfylline; thrombolytics, and anticoagulants including platelet aggregation inhibitors.

The present invention still further relates to the combination of a compound of the invention together with CNS agents such as antidepressants (such as sertraline), anti-Parkinsonian drugs (such as deprenyl, L-dopa, Requip, Mirapex, MAOB inhibitors such as selegine and rasagiline, comP inhibitors such as Tasmar, A-2 inhibitors, dopamine reuptake inhibitors, NMDA antagonists, nicotine agonists, dopamine agonists and inhibitors of neuronal nitric oxide synthase), and anti-Alzheimer's drugs such as donepezil, tacrine, COX-2 inhibitors, propentofylline or metrifonate.

The present invention still further relates to the combination of a compound of the invention together with agents for the treatment of acute and chronic pain, including centrally and peripherally-acting analgesics such as opioid analogues and derivatives, carbamazepine, phenytoin, sodium valproate, amitryptiline and other antidepressant agents, and non-steroidal anti-inflammatory agents.

The present invention still further relates to the combination of a compound of the invention together with parenterally or topically-applied local anaesthetic agents such as lignocaine.

The present invention still further relates to the combination of a compound of the invention together with (i) tryptase inhibitors; (ii) platelet activating factor (PAF) antagonists; (iii) interleukin converting enzyme (ICE) inhibitors; (iv) IMPDH inhibitors; (v) adhesion molecule inhibitors including VLA-4 antagonists; (vi) cathepsins; (vii) MAP kinase inhibitors; (viii) glucose-6 phosphate dehydrogenase inhibitors; (ix) kinin-B.sub1.- and B.sub2.-receptor antagonists; (x) anti-gout agents, e.g., colchicine; (xi) xanthine oxidase inhibitors, e.g., allopurinol; (xii) uricosuric agents, e.g., probenecid, sulfinpyrazone, and benzbromarone; (xiii) growth hormone secretagogues; (xiv) transforming growth factor (TGFβ); (xv) platelet-derived growth factor (PDGF); (xvi) fibroblast growth factor, e.g., basic fibroblast growth factor (bFGF); (xvii) granulocyte macrophage colony stimulating factor (GM-CSF); (xviii) capsaicin cream; (xix) Tachykinin NK.sub1. and NK.sub3. receptor antagonists selected from the group consisting of NKP-608C; SB-233412 (talnetant); and D-4418; (xx) elastase inhibitors selected from the group consisting of UT-77 and ZD-0892; (xxi) TNF☐ converting enzyme inhibitors (TACE); (xxii) induced nitric oxide synthase inhibitors (iNOS) or (xxiii) chemoattractant receptor-homologous molecule expressed on TH2 cells, (CRTH2 antagonists) (xxiv) inhibitors of P38

The compounds of the present invention may also be used in combination with anti-osteoporosis agents including hormonal agents such as raloxifene, and biphosphonates such as alendronate.

The compounds of the invention may also be used in combination with existing therapeutic agents for the treatment of osteoarthritis. Suitable agents to be used in combination include standard non-steroidal anti-inflammatory agents (hereinafter NSAIDs) such as piroxicam, diclofenac, propionic acids such as naproxen, flubiprofen, fenoprofen, ketoprofen and ibuprofen, fenamates such as mefenamic acid, indomethacin, sulindac, apazone, pyrazolones such as phenylbutazone, salicylates such as aspirin, COX-2 inhibitors such as celecoxib, valdecoxib, rofecoxib and etoricoxib, analgesics, and intra-articular therapies such as corticosteroids and hyaluronic acid derivatives, and nutritional supplements such as glucosamine.

The compounds of the invention can also be used in combination with existing therapeutic agents for the treatment of cancer. Suitable agents to be used in combination include:

(i) antiproliferative/antineoplastic drugs and combinations thereof, as used in medical oncology, such as alkylating agents (for example cis-platin, carboplatin, cyclophosphamide, nitrogen mustard, melphalan, chlorambucil, busulphan and nitrosoureas); antimetabolites (for example antifolates such as fluoropyrimidines like 5-fluorouracil and tegafur, raltitrexed, methotrexate, cytosine arabinoside, hydroxyurea, gemcitabine and paclitaxel; antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere); and topoisomerase inhibitors (for example epipodophyllotoxins like etoposide and teniposide, amsacrine, topotecan and camptothecins);

(ii) cytostatic agents such as antioestrogens (for example tamoxifen, toremifene, raloxifene, droloxifene and iodoxyfene), oestrogen receptor down regulators (for example fulvestrant), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;

(iii) Agents which inhibit cancer cell invasion (for example metalloproteinase inhibitors like marimastat and inhibitors of urokinase plasminogen activator receptor function);

(iv) inhibitors of growth factor function, for example such inhibitors include growth factor antibodies, growth factor receptor antibodies (for example the anti-erbb2 antibody trastuzumab and the anti-erbb1 antibody cetuximab [C225]), farnesyl transferase inhibitors, tyrosine kinase inhibitors and serine/threonine kinase inhibitors, for example inhibitors of the epidermal growth factor family (for example EGFR family tyrosine kinase inhibitors such as N-(3-chloro-4-fluorophenyl)-7-methoxy-6-(3-morpholinopropoxy)quinazolin-4-amine (gefitinib, AZD1839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy)quinazolin-4-amine (CI 1033)), for example inhibitors of the platelet-derived growth factor family and for example inhibitors of the hepatocyte growth factor family;

(v) antiangiogenic agents such as those which inhibit the effects of vascular endothelial growth factor, (for example the anti-vascular endothelial cell growth factor antibody bevacizumab, compounds such as those disclosed in International Patent Applications WO 97/22596, WO 97/30035, WO 97/32856 and WO 98/13354) and compounds that work by other mechanisms (for example linomide, inhibitors of integrin αvβ3 function and angiostatin);

(vi) vascular damaging agents such as combretastatin A4 and compounds disclosed in International Patent Applications WO 99/02166, WO00/40529, WO 00/41669, WO01/92224, WO02/04434 and WO02/08213;

(vii) antisense therapies, for example those which are directed to the targets listed above, such as ISIS 2503, an anti-ras antisense;

(viii) gene therapy approaches, including for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; and (ix) immunotherapy approaches, including for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies.

In a still further aspect, the present invention provides the use of a compound of formula (I), or a pharmaceutically acceptable salt or solvate thereof, as hereinbefore defined in the manufacture of a medicament for the treatment of human diseases or conditions in which modulation of CRTh2 receptor activity is beneficial.

In the context of the present specification, the term "therapy" also includes "prophylaxis" unless there are specific indications to the contrary. The terms "therapeutic" and "therapeutically" should be construed accordingly.

The invention still further provides a method of treating diseases mediated by PGD2 or its metabolites wherein the prostanoid binds to its receptor (especially CRTh2) receptor, which comprises administering to a patient a therapeutically effective amount of a compound of formula (I), or a pharmaceutically acceptable salt, solvate or prodrug thereof, as hereinbefore defined.

The invention also provides a method of treating an inflammatory disease, especially psoriasis, in a patient suffering from, or at risk of, said disease, which comprises administering to the patient a therapeutically effective amount of a compound of formula (I), or a pharmaceutically acceptable salt or solvate thereof, as hereinbefore defined.

For the above-mentioned therapeutic uses the dosage administered will, of course, vary with the compound employed, the mode of administration, the treatment desired and the disorder indicated.

For the above-mentioned therapeutic uses the dosage administered will, of course, vary with the compound employed, the mode of administration, the treatment desired and the disorder indicated.

The compound of formula (I), prodrugs and pharmaceutically acceptable salts and solvates thereof may be used on their own but will generally be administered in the form of a pharmaceutical composition in which the formula (I) compound/salt/solvate (active ingredient) is in association with a pharmaceutically acceptable adjuvant, diluent or carrier. Depending on the mode of administration, the pharmaceutical composition will preferably comprise from 0.05 to 99% w (percent by weight), more preferably from 0.05 to 80% w, still more preferably from 0.10 to 70% w, and even more preferably from 0.10 to 50% w, of active ingredient, all percentages by weight being based on total composition.

The present invention also provides a pharmaceutical composition comprising a compound of formula (I), or a pharmaceutically acceptable salt or solvate thereof, as herein before defined, in association with a pharmaceutically acceptable adjuvant, diluent or carrier.

The pharmaceutical compositions may be administered topically (e.g. to the lung and/or airways or to the skin) in the form of solutions, suspensions, heptafluoroalkane aerosols and dry powder formulations; or systemically, e.g. by oral administration in the form of tablets, capsules, syrups, powders or granules, or by parenteral administration in the form of solutions- or suspensions, or by subcutaneous administration or by rectal administration in the form of suppositories or transdermally. Preferably the compound of the invention is administered orally.

The invention will now be illustrated by the following non-limiting examples in which, unless stated otherwise:
(i) when given, $^1$H NMR data is quoted in the form of delta values for major diagnostic protons, given in parts per million (ppm) relative to tetramethylsilane (TMS) as an internal standard;
(ii) mass spectra (MS): generally only ions which indicate the parent mass are reported, and unless otherwise stated the mass ion quoted is the positive mass ion—(M+H)$^+$;
(iii) the title compounds of the examples and methods were named using the ACD/name and ACD/name batch (version 6.0) from Advanced Chemical Development Inc, Canada;
(iv) unless stated otherwise, reverse phase HPLC was conducted using a Symmetry, NovaPak or Ex-Terra reverse phase silica column;
(v) solvents were dried with MgSO$_4$ or Na$_2$SO$_4$
(vi) the following abbreviations are used:
EtOAc Ethylacetate
DCM Dichloromethane
NMP N-methylpyrrolidine
DMF N,N-dimethylformamide
THF tetrahydrofuran
mcpba 3-chloroperoxybenzoic acid (Aldrich 77% max)
Pd(dppf)Cl$_2$ [1,1'-Bis(diphenylphosphino)ferrocene] dichloropalladium(II), complex with dichloromethane
RT room temperature

EXAMPLE 1

{[5-Chloro-4'-(ethylthio)biphenyl-2-yl]oxy}acetic acid

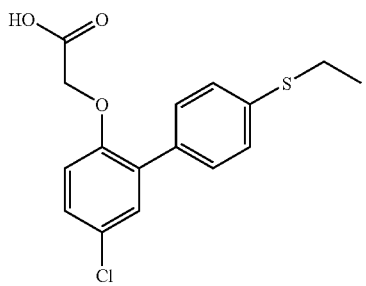

(i) tert-Butyl(2-bromo-4-chlorophenoxy)acetate tert-Butyl bromoacetate (2.6 ml) was added to a stirred mixture of 4-bromo-2-chlorophenol (3 g) and potassium carbonate (6.2 g) in DMF (40 ml) at RT. After 16 h the reaction was partitioned between diethylether and water, the organics separated, dried and evaporated under reduced pressure. The residue was purified by chromatography on silica eluting with 4% EtOAc/iso-hexane. Yield 4.05 g
$^1$H NMR CDCl$_3$: δ 7.55 (1H, d); 7.21 (1H, dd); 6.72 (1H, d); 4.57 (2H, s); 1.48 (9H, s)

(ii) tert-Butyl {[5-chloro-4'-(ethylthio)biphenyl-2-yl]oxy}acetate

A mixture of the product from step (i) (2 g), 4-(ethylthio)phenylboronic acid (1.5 g), cesium fluoride (2 g) and Pd(dppf)Cl$_2$ (0.2 g) in dioxane (40 ml) was heated under reflux for 3 h. After cooling the mixture was partitioned between diethylether and water. The organics were separated, dried and evaporated under reduced pressure. The residue was purified by chromatography on silica eluting with 5% EtOAc/iso-hexane. Yield 0.92 g
MS: APCI (+ve): 379/381 (M+1)

(iii) {[5-Chloro-4'-(ethylthio)biphenyl-2-yl]oxy}acetic acid

The title compound was prepared by stirring a mixture of the product from step (ii) (0.3 g) and trifluoroacetic acid (4 ml) in DCM (10 ml) at RT for 5 h. The solvent was evaporated under reduced pressure, the residue triturated with diethylether then purified by reverse phase HPLC. Yield 0.106 g
$^1$H NMR DMSO-d6: δ 13.07 (1H, s); 7.54 (2H, d); 7.35-7.33 (4H, m); 7.02 (1H, d); 4.74 (2H, s); 3.02 (2H, q); 1.27 (3H, t)
MS: APCI (−ve): 321/3 (M−1)

EXAMPLE 2

{[5-Chloro-4'-(ethylsulfonyl)biphenyl-2-yl]oxy}acetic acid

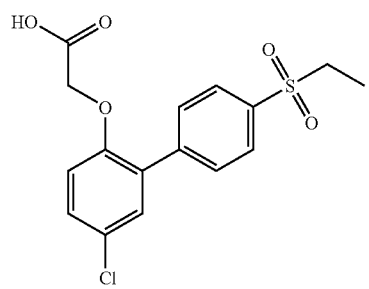

(i) tert-Butyl {[5-chloro-4'-(ethylsulfonyl)biphenyl-2-yl]oxy}acetate

Mcpba (1.2 g) was added to a stirred solution of the product from example 1 step (ii) (0.6 g) in DCM (10 ml) at RT. After 4 h, the mixture was partitioned between DCM and aqueous sodium metabisulphite solution, the organics separated, washed with aqueous sodium hydrogencarbonate solution, water, dried and evaporated under reduced pressure. Yield 0.65 g (ii) {[5-Chloro-4'-(ethylsulfonyl)biphenyl-2-yl]oxy}acetic acid The title compound was prepared by the method of example 1 step (iii) using the product from step (i). Yield 0.226 g ¹H NMR DMSO-d6: δ 13.14 (1H, s); 7.92 (2H, d); 7.87 (2H, d); 7.45-7.42 (2H, m); 7.10 (1H, d); 4.79 (2H, s); 3.35 (2H, q); 1.15 (3H, t)

MS: APCI (−ve): 353/5 (M−1)

EXAMPLE 3

[(4',5-Dichlorobiphenyl-2-yl)oxy]acetic acid

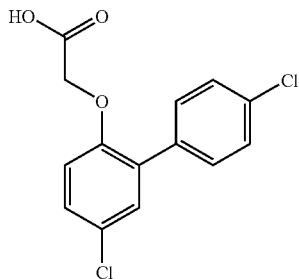

(i) tert-Butyl [(4',5-dichlorobiphenyl-2-yl)oxy]acetate

The subtitle compound was prepared by the method of example 1 step (ii) using the product from example 1 step (i) and 4-chlorophenylboronic acid. Yield 0.63 g ¹H NMR CDCl₃: δ 7.54-7.22 (6H, m); 6.76 (1H, dd); 4.48 (2H, s); 1.47 (9H, s)

(ii) [(4',5-Dichlorobiphenyl-2-yl)oxy]acetic acid

The title compound was prepared by the method of example 1 step (iii) using the product from step (i). Yield 0.224 g ¹H NMR DMSO-d6: δ 13.00 (1H, s); 7.61 (2H, d); 7.48 (2H, d); 7.41-7.36 (2H, m); 7.05 (1H, d); 4.75 (2H, s)

MS: APCI (−ve): 295/7 (M−1)

EXAMPLE 4

[(5-Chloro-4'-cyanobiphenyl-2-yl)oxy]acetic acid

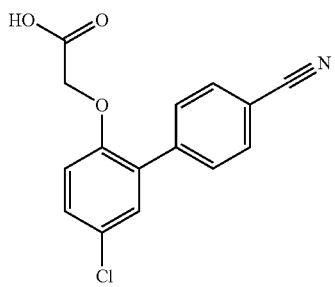

(i) tert-Butyl [(5-chloro-4'-cyanobiphenyl-2-yl)oxy]acetate

The subtitle compound was prepared by the method of example 1 step (ii) using the product from example 1 step (i) and 4-cyanophenylboronic acid. Yield 0.524 g ¹H NMR CDCl₃: δ 7.70 (4H, s); 7.32-7.26 (2H, m); 6.79 (1H, d); 4.51 (2H, s); 1.48 (9H, s)

(ii) [(5-Chloro-4'-cyanobiphenyl-2-yl)oxy]acetic acid

The title compound was prepared by the method of example 1 step (iii) using the product from step (i). Yield 0.109 g ¹H NMR DMSO-d6: δ 13.14 (1H, s); 7.90 (2H, d); 7.80 (2H, d); 7.45-7.41 (2H, m); 7.10 (1H, d); 4.78 (2H, s)

MS: APCI (−ve): 286/8 (M−1)

EXAMPLE 5

[(5-Chloro-4'-methoxybiphenyl-2-yl)oxy]acetic acid

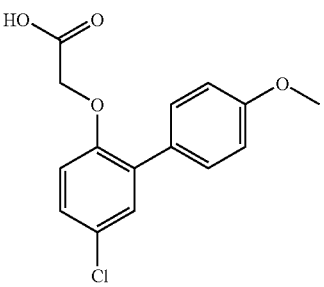

(i) tert-Butyl [(5-chloro-4'-methoxybiphenyl-2-yl)oxy]acetate

The subtitle compound was prepared by the method of example 1 step (ii) using the product from example 1 step (i) and 4-methoxyphenylboronic acid. Yield 0.610 g ¹H NMR CDCl₃: δ 7.54 (2H, d); 7.31-7.18 (2H, m); 6.96 (2H, d); 6.76 (1H, d); 4.46 (2H, s); 3.84 (3H, s); 1.46 (9H, s)

(ii) [(5-Chloro-4'-methoxybiphenyl-2-yl)oxy]acetic acid

The title compound was prepared by the method of example 1 step (iii) using the product from step (i). Yield 0.119 g ¹H NMR DMSO-d6: δ 13.08 (1H, s); 7.53 (2H, d); 7.32-7.29 (2H, m); 7.01-6.96 (3H, m); 4.72 (2H, s); 3.79 (3H, s)

MS: APCI (−ve): 291/3 (M−1)

EXAMPLE 6

(4-Chloro-2-quinolin-8-ylphenoxy)acetic acid, trifluoroacetic acid salt

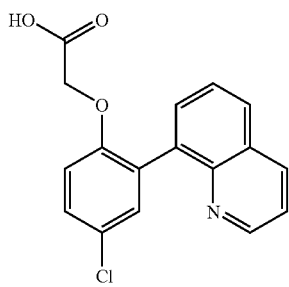

(i) tert-Butyl(4-chloro-2-quinolin-8-ylphenoxy)acetate

The subtitle compound was prepared by the method of example 1 step (ii) using the product from example 1 step (i) and 8-quinoline boronic acid. Yield 0.356 g $^1$H NMR CDCl$_3$: δ 8.90-8.88 (1H, m); 8.18 (1H, d); 7.85 (1H, d); 7.76 (1H, d); 7.60 (1H, t); 7.40-7.30 (3H, m); 6.87 (1H, d); 4.37 (2H, s); 1.37 (9H, s)

(ii) (4-Chloro-2-quinolin-8-ylphenoxy)acetic acid, trifluoroacetic acid salt

The title compound was prepared by the method of example 1 step (iii) using the product from step (i). Yield 0.25 g $^1$H NMR DMSO-d6: δ 8.91-8.89 (1H, m); 8.62 (1H, d); 8.12 (1H, d); 7.85-7.67 (3H, m); 7.46 (1H, dd); 7.38 (1H, d); 7.09 (1H, d); 4.61 (2H, s)

MS: APCI (−ve): 312/4 (M−1)

EXAMPLE 7

[(5-Chloro-3',4'-dimethoxybiphenyl-2-yl)oxy]acetic acid

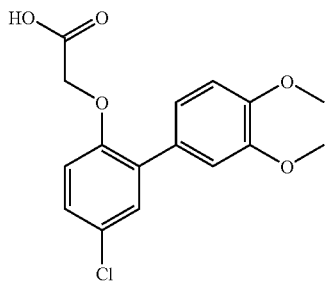

(i) tert-Butyl [(5-chloro-3',4'-dimethoxybiphenyl-2-yl)oxy]acetate

The subtitle compound was prepared by the method of example 1 step (ii) using the product from example 1 step (i) and 3,4-dimethoxyphenylboronic acid. Yield 0.86 g $^1$H NMR CDCl$_3$: δ 7.33-7.12 (4H, m); 6.93 (1H, d); 6.79 (1H, d); 4.46 (2H, s); 3.93 (3H, s); 3.92 (3H, s); 1.46 (9H, s)

(ii) [(5-Chloro-3',4'-dimethoxybiphenyl-2-yl)oxy]acetic acid

The title compound was prepared by the method of example 1 step (iii) using the product from step (i). Yield 0.32 g $^1$H NMR DMSO-d6: δ 13.08 (1H, s); 7.36-7.27 (3H, m); 7.12-6.98 (3H, m); 4.74 (2H, s); 3.78 (6H, 2×s)

MS: APCI (−ve): 321/3 (M−1)

EXAMPLE 8

2'-(Carboxymethoxy)-5'-chlorobiphenyl-4-carboxylic acid

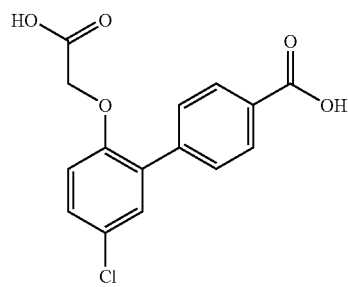

The title compound was prepared by the method of example 1 step (ii) and step (iii) using the product from example 1 step (i) and 4-carboxyphenylboronic acid. Yield 0.035 g $^1$H NMR DMSO-d6: δ 7.98-7.38 (6H, m); 7.08-7.05 (1H, m); 4.75 (2H, s)

MS: APCI (−ve): 305 (M−1)

EXAMPLE 9

{[5-Chloro-4'-(methylsulfonyl)biphenyl-2-yl]oxy}acetic acid

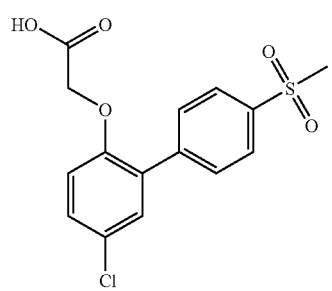

The title compound was prepared by the method of example 1 step (ii) and example 2 using the product from example 1 step (i) and 4-(methylthio)benzeneboronic acid. Yield 0.1 g $^1$H NMR DMSO-d6: δ 7.97-7.08 (7H, m); 4.78 (2H, s); 3.31 (3H, bs)

MS: APCI (−ve): 339 (M−1)

EXAMPLE 10

{[5-Chloro-4'-(ethylsulfonyl)-2'-methylbiphenyl-2-yl]oxy}acetic acid

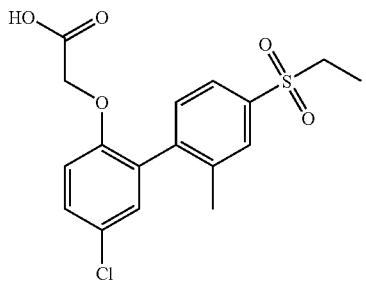

(i) 4-Bromo-3-methylphenyl ethyl sulfide

Bromine (2.2 ml) was added to a solution of 1-(ethylthio)-3-methylbenzene (6.6 g) in acetic acid (20 ml) at 0° C. The mixture was stirred at RT for 2 h then the solvent removed under reduced pressure. The residue was purified by chromatography on silica eluting with DCM. Yield 6.6 g MS: APCI (+ve): 247/9 (M+1)

(ii) 2-[4-(Ethylthio)-2-methylphenyl]-4,4,5,5-tetramethyl-1,3,2-dioxaborolane A mixture of the product from step (i) (6.6 g), 4,4,5,5-tetramethyl-[1,3,2]-dioxaborolane (1.94 ml), triethylamine (2.4 ml), palladium acetate (0.06 g) and 2-(dicyclohexylphosphino) biphenyl (0.3 g) in dioxane (20 ml) was heated at 85° C. for 2 h. The mixture was quenched with aqueous ammonium chloride solution, extracted with diethylether, the organics dried and evaporated under reduced pressure. The residue was purified by chromatography on silica eluting with 50% isohexane/DCM. Yield 0.7 g $^1$H NMR CDCl$_3$: δ 7.66 (1H, d); 7.08-7.05 (2H, m); 2.94-2.92 (2H, q); 2.5 (3H, s); 1.43-1.27 (15H, m)

(iii) {[5-Chloro-4'-(ethylsulfonyl)-2'-methylbiphenyl-2-yl]oxy}acetic acid

The title compound was prepared by the method of example 1 step (ii) and example 2 using the product from step (ii) and the product from example 1 step (i). Yield 0.035 g $^1$H NMR DMSO-d6: δ 7.79-6.99 (6H, m); 4.67 (2H, s); 3.35 (2H, q); 2.23 (3H, s); 1.15 (3H, t)

MS: APCI (-ve): 367 (M-1)

EXAMPLE 11

[(5-Cyanobiphenyl-2-yl)oxy]acetic acid

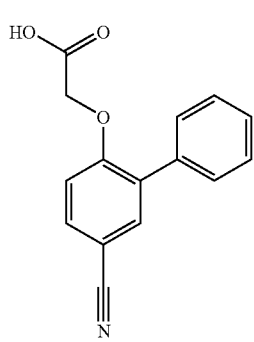

The title compound was prepared by the method of example 1 using 3-bromo-4-hydroxybenzonitrile and phenylboronic acid. Yield 0.175 g $^1$H NMR DMSO-d6: δ 13.18 (1H, s); 7.81-7.17 (8H, m); 4.87 (2H, s)

MS: APCI (-ve): 252 (M-1)

EXAMPLE 12

[(5-Nitrobiphenyl-2-yl)oxy]acetic acid

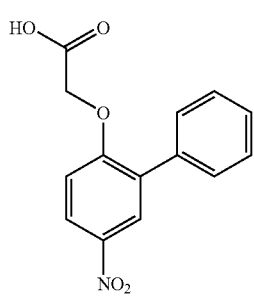

The title compound was prepared by the method of example 1 using 2-bromo-4-nitrophenol and phenylboronic acid. Yield 0.065 g $^1$H NMR DMSO-d6: δ 13.26 (1H, s); 8.23 (1H, dd); 8.12 (1H, d); 7.63 (2H, d); 7.50-7.38 (3H, m); 7.25 (1H, d); 4.94 (2H, s)

MS: APCI (-ve): 272 (M-1)

EXAMPLE 13

{[4'-(Methylthio)-5-(trifluoromethyl)biphenyl-2-yl]oxy}acetic acid

(i) 2-Iodo-4-(trifluoromethyl)phenol

Sodium iodide (3.32 g) then chloramine-T (5.91 g) were added to a stirred solution of 4-trifluoromethylphenol (3.0 g) in DMF (30 ml) at 0° C. The mixture was warmed to RT, stirred for 1 h, diluted with dilute hydrochloric acid then extracted with diethylether. The organic layer was washed with aqueous sodium thiosulphate solution, dried and the solvent removed under reduced pressure. Yield 5.25 g MS: APCI (−ve): 287 (M−1)

(ii) {[4'-(Methylthio)-5-(trifluoromethyl)biphenyl-2-yl]oxy}acetic acid

The title compound was prepared by the method of example 1 using the product from step (i) and 4-(methylthio)benzeneboronic acid. Yield 0.13 g $^1$H NMR DMSO-d6: δ 13.16 (1H, s); 7.68-7.18 (7H, m); 4.85 (2H, s); 2.51 (3H, s)

MS: APCI (−ve): 341 (M−1)

EXAMPLE 14

{[4'-(Methylsulfonyl)-5-(trifluoromethyl)biphenyl-2-yl]oxy}acetic acid, ammonium salt The title compound was prepared by the methods of example 1 and 2 using the product from example 13 step (i) and 4-(methylthio)benzeneboronic acid. Yield 0.14 g $^1$H NMR DMSO-d6: δ 13.21 (1H, s); 8.00-7.69 (6H, m); 7.27 (1H, d); 4.89 (2H, s); 3.27 (3H, s)

MS: APCI (−ve): 373 (M−1)

EXAMPLE 15

{[4'-(Ethylsulfonyl)-2'-methyl-5-(trifluoromethyl)biphenyl-2-yl]oxy}acetic acid

The title compound was prepared by the methods of example 1 and 2 using the product from example 13 step (i) and the product from example 10 step (ii). Yield 0.055 g $^1$H NMR DMSO-d6: δ 7.80-7.12 (6H, m); 4.63 (2H, s); 3.39-3.29 (2H, q); 2.23 (3H, s); 1.18-1.11 (3H, t)

MS: APCI (−ve): 401 (M−1)

EXAMPLE 16

(4-Chloro-2-pyrimidin-5-ylphenoxy)acetic acid, ammonium salt

(i) Benzyl 2-bromo-4-chlorophenyl ether

Benzyl bromide (13.1 ml) was added to a stirred mixture of 2-bromo-4-chlorophenol (20.7 g) and potassium carbonate (27.6 g) in DMF (200 ml). After 72 h, the mixture was partitioned between diethylether and water, the organic layer washed with water, dried and the solvent evaporated under reduced pressure. The residue was purified by chromatography on silica eluting with 2% EtOAc/isohexane. Yield 18.1 g $^1$H NMR CDCl$_3$: δ 7.55 (1H, s); 7.46-7.18 (6H, m); 6.84 (1H, d); 5.14 (2H, s)

(ii) [2-(Benzyloxy)-5-chlorophenyl]boronic acid

A solution of butyl lithium (1.6M in hexane) (50 ml) was added dropwise to a stirred solution of the product from step (i) (23 g) in diethylether (300 ml) at −70° C. After 1 h a further 18 ml of butyl lithium was added, left for 0.75 h, then trimethylborate (10 ml) added and the mixture warmed to RT and left for 16 h. 2M Hydrochloric acid (100 ml) was added, stirred for 1 h then the organic layer separated and extracted with aqueous sodium hydroxide solution. The basic layer was acidified with 2M hydrochloric acid solution, extracted with diethylether which was dried and evaporated under reduced pressure. The residue was triturated with iso-hexane and filtered. Yield 10.8 g
$^1$H NMR CDCl$_3$: δ 7.82 (1H, d); 7.44-7.34 (6H, m); 6.90 (1H, d); 5.99 (2H, s); 5.12 (2H, s)

(iii) 5-[2-(Benzyloxy)-5-chlorophenyl]pyrimidine

A mixture of the product from step (ii) (0.2 g), 5-bromopyrimidine (0.16 g), sodium carbonate (0.21 g) and tetrakistriphenylphosphine palladium (0) (0.05 g) in dioxane (6 ml) was heated under reflux for 48 h. The mixture was partitioned between EtOAc and water, the organics separated, dried, and evaporated under reduced pressure. The residue was purified by chromatography on silica eluting with 20% EtOAc/iso-hexane. Yield 0.283 g.
MS: APCI (+ve): 297/9 (M+1)

(iv) 4-Chloro-2-pyrimidin-5-ylphenol

A mixture of the product from step (iii) (0.28 g), 10% palladium on carbon (0.04 g) in ethanol (20 ml) was hydrogenated at 2 Bar for 24 h. After filtration the solvent was evaporated under reduced pressure. Yield 0.19 g
MS: APCI (+ve): 207/9 (M+1)

(v) tert-Butyl(4-chloro-2-pyrimidin-5-ylphenoxy)acetate

The subtitle compound was prepared by the method of example 1 step (i). Yield 0.216 g
MS: APCI (+ve): 321/3 (M+1)

(vi) (4-Chloro-2-pyrimidin-5-ylphenoxy)acetic acid, ammonium salt

The title compound was prepared by the method of example 1 step (iii). Yield 0.033 g
$^1$H NMR DMSO-d6: δ 9.15 (1H, s); 9.08 (2H, s); 7.57 (1H, d); 7.44 (1H, dd); 7.10 (1H, d); 4.67 (2H, s)
MS: APCI (+ve): 265/7 (m+1)

EXAMPLE 17

{2-[5-(Aminosulfonyl)pyridin-2-yl]-4-chlorophenoxy}acetic acid

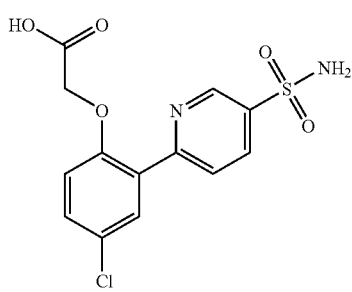

The title compound was prepared by the method of example 16. Yield 0.022 g
$^1$H NMR DMSO-d6: δ 13.19 (1H, s); 9.05 (1H, s); 8.29 (1H, d); 8.21 (1H, d); 7.84 (1H, d); 7.65 (2H, s); 7.49 (1H, dd); 7.16 (1H, d); 4.86 (2H, s)
MS: APCI (+ve): 343/5 (M+1)

EXAMPLE 18

[2-(2-Aminopyrimidin-5-yl)-4-chlorophenoxy]acetic acid, trifluoroacetate salt

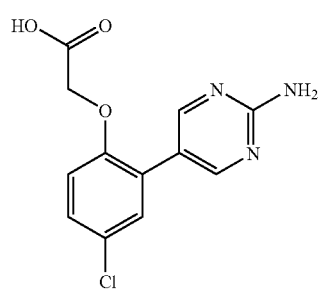

The title compound was prepared by the method of example 16. Yield 0.036 g
$^1$H NMR DMSO-d6: δ 8.56 (2H, s); 7.45 (1H, d); 7.33 (1H, dd); 7.05 (1H, d); 4.76 (2H, s)
MS: APCI (+ve): 280/2 (M+1)

EXAMPLE 19

[4-Chloro-2-(4-methyl-2-morpholin-4-ylpyrimidin-5-yl)phenoxy]acetic acid

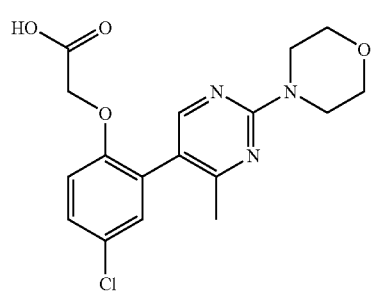

(i) 2-[2-(Benzyloxy)-5-chlorophenyl]-N-methoxy-N-methylacetamide 1-(3-Dimethylaminopropyl)$_3$-ethylcarbodiimide hydrochloride (8.6 g) was added to a solution of (2-benzyloxy-5-chlorophenyl)-acetic acid (10.6 g), N,O-dimethylhydroxylamine hydrochloride (4.4 g), 1-hydroxybenzotriazole (6.9 g) and N,N-diisopropylethylamine (20 ml) in DMF (150 ml) and the mixture stirred at RT for 16 h, then partitioned between ethylacetate and water. The organics were washed with 2M hydrochloric acid, water, dried, and evaporated under reduced pressure. Yield 12.2 g
MS: APCI (+ve): 320/2 (M+1)

(ii) 1-[2-(Benzyloxy)-5-chlorophenyl]acetone

A solution of methylmagnesium chloride (3M in THF) (6 ml) was added dropwise to a stirred solution of the product, from step (i) (5.2 g) in THF (150 ml) at −70° C. After 1 h the mixture was warmed to RT, stirred for 1 h then quenched with aqueous ammonium chloride solution. The mixture was partitioned between diethylether and water, the organics separated, dried, and evaporated under reduced pressure. The residue was purified by chromatography on silica eluting with 10% EtOAc/isohexane. Yield 2.22 g $^1$H NMR CDCl$_3$: δ 7.40-7.30 (5H, m); 7.26-7.12 (2H, m); 6.85 (1H, d); 5.03 (2H, s); 3.67 (2H, s); 2.12 (3H, s)

(iii) (3Z)-3-[2-(Benzyloxy)-5-chlorophenyl]-4-(dimethylamino)but-3-en-2-one

A mixture of the product from step (ii) (5.72 g) and dimethylformamide dimethyl acetal (3.5 ml) in toluene (50 ml) were heated at 100° C. for 12 h. The solvent was evaporated under reduced pressure to give an oil, 6.37 g.
MS: APCI (+ve): 330/2 (M+1)

(iv) 5-[2-(Benzyloxy)-5-chlorophenyl]-4-methyl-2-(methylthio)pyrimidine

A solution of the product from step (iii) (4.3 g) in ethanol (20 ml) was added to a stirred mixture of sodium ethoxide (0.98 g) and S-methylisothiouronium sulphate (2 g) in ethanol (30 ml), and the mixture heated under reflux for 8 h. A further 2 g of S-methylisothiouronium sulphate and 1.18 g of sodium ethoxide were added and heating continued for 16 h. The mixture was cooled, partitioned between diethylether and water, the organics washed with water, dried, and evaporated under reduced pressure. The residue was purified by chromatography on silica eluting with 3-5% EtOAc/isohexane. Yield 1.84 g
MS: APCI (+ve): 357/9 (M+1)

(v) 5-[2-(Benzyloxy)-5-chlorophenyl]-4-methyl-2-(methylsulfonyl)pyrimidine

The subtitle compound was prepared by the method of example 2 step (i). Yield 0.85 g
MS: APCI (+ve): 389/91 (M+1)

(vi) 4-Chloro-2-[4-methyl-2-(methylsulfonyl)pyrimidin-5-yl]phenol

The subtitle compound was prepared by the method of example 16 step (iv). Yield 0.5 g
MS: APCI (+ve): 299/301 (M+1)

(vii) tert-Butyl {4-chloro-2-[4-methyl-2-(methylsulfonyl)pyrimidin-5-yl]phenoxy}acetate The subtitle compound was prepared by the method of example 1 step (i). Yield 0.65 g
MS: APCI (+ve): 413 (M+1)

(viii) tert-Butyl[4-chloro-2-(4-methyl-2-morpholin-4-ylpyrimidin-5-yl)phenoxy]acetate A solution of the product from step (vii) (0.15 g) and morpholine (0.15 ml) in dioxane (3 ml) was heated at 90° C. for 24 h, cooled and the solvent evaporated under reduced pressure.
Product used crude.
MS: APCI (+ve): 420/422 (M+1)

(ix) [4-Chloro-2-(4-methyl-2-morpholin-4-ylpyrimidin-5-yl)phenoxy]acetic acid The title compound was prepared by the method of example 1 step (iii). Yield 0.046 g
$^1$H NMR DMSO-d6: δ 8.12 (1H, s); 7.39 (1H, dd); 7.25 (1H, d); 7.00 (1H, d); 4.71 (2H, s); 3.73-3.67 (8H, m); 2.18 (3H, s)
MS: APCI (+ve): 364/6 (M+1)

EXAMPLE 20

{4-Chloro-2-[2-(dimethylamino)pyrimidin-5-yl]phenoxy}acetic acid

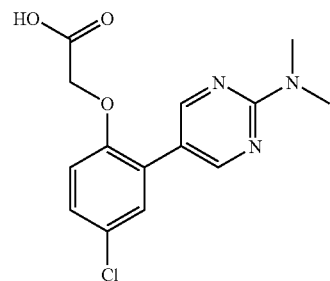

(i) 5-[2-(Benzyloxy)-5-chlorophenyl]-2-chloropyrimidine

The subtitle compound was prepared by the method of example 1 step (ii) using the product from example 16 step (ii) (3.2 g) and 2-chloro-5-bromopyrimidine (2.59 g). Yield 2.43 g
MS: APCI (+ve): 331/3 (M+1)

(ii) 5-[2-(Benzyloxy)-5-chlorophenyl]-2-(propylthio)pyrimidine

Propanethiol (3.1 ml) was added to a stirred suspension of sodium hydride (1.4 g, 60% in oil) in DMF (30 ml). After 1 hour a solution of the product from step (i) (2.4 g) in DMF (10 ml) was added. The reaction mixture was stirred at RT for 1 hour then partitioned between EtOAc and water. The organics were washed with water, brine, dried and evaporated under reduced pressure. The residue was purified by chromatography on silica eluting with 5% EtOAc/isohexane. Yield 1.87 g
MS: APCI(+ve) 371 (M+1)

(iii) 5-[2-(Benzyloxy)-5-chlorophenyl]-2-(propylsulfonyl)pyrimidine

The subtitle compound was prepared by the method of example 2 step (i) using the product from step (ii).
MS: APCI(+ve) 403 (M+1)

(iv) tert-Butyl {4-chloro-2-[2-(propylsulfonyl)pyrimidin-5-yl]phenoxy}acetate The subtitle compound was prepared by the method of example 16 step (iv) and example 1 step (i) using the product from step (iii). Yield 1.04 g
MS: APCI(+ve) 427 (M+1)

(v) {4-Chloro-2-[2-(dimethylamino)pyrimidin-5-yl]phenoxy}acetic acid

Dimethylamine hydrochloride (0.82 g) was added to a stirred solution of the product from step (iv) (0.2 g) and N,N-diisopropylethylamine (0.9 ml) in No (5 ml). The reaction mixture was heated at 90° C. for 6 h then diluted with EtOAc, washed with water, brine, dried and evaporated under reduced pressure. The residue was dissolved in DCM (10 ml) then trifluoroacetic acid (10 ml) added and stirred for 18 h at RT. The reaction mixture was evaporated to dryness and the residue purified by reverse phase HPLC followed by trituration with methanol to give a white solid. Yield 0.035 g 1H NMR DMSO-d6: δ8.60 (2H, s); 7.42 (1H, d); 7.32 (1H, dd); 7.05 (1H, d); 4.77 (2H, s); 3.16 (6H, s).

MS: APCI(−ve) 306 (M−1)

EXAMPLE 21

[4-Chloro-2-(2-morpholin-4-ylpyrimidin-5-yl)phenoxy]acetic acid

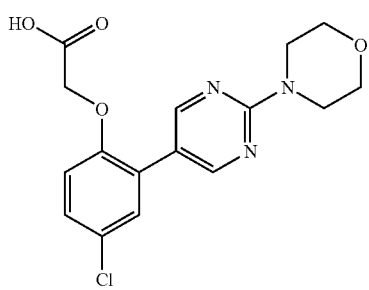

The title compound was prepared from the product of example 20 step (iv) and morpholine by the method of example 20 step (v).

$^1$H NMR DMSO-d6: δ13.10 (1H, brs); 8.65 (2H, s); 7.45 (1H, d); 7.34 (1H, dd); 7.06 (1H, d); 4.77 (2H, s); 3.75 (4H, m); 3.67 (4H, m)

MS: APCI(−ve) 348 (M−1)

EXAMPLE 22

{4-Chloro-2-[2-(methylamino)pyrimidin-5-yl]phenoxy}acetic acid

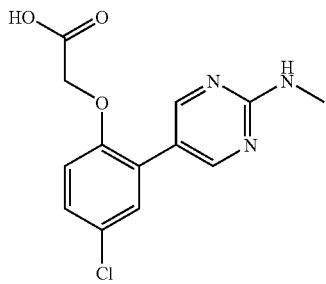

The title compound was prepared from the product of example 20 step (iv) and methylamine hydrochloride by the method of example 20 step (v).

1H NMR DMSO-d6: δ8.54 (2H,s); 7.42 (1H, d); 7.32 (1H, dd); 7.25 (1H, brs); 7.04 (1H, d); 4.76 (2H, s); 2.84 (3H, s)

MS: APCI(−ve) 292 (M−1)

EXAMPLE 23

{2-[2-(Benzylamino)pyrimidin-5-yl]-4-chlorophenoxy}acetic acid

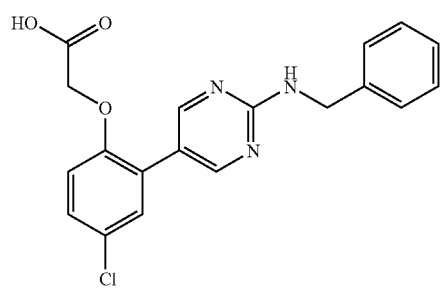

The title compound was prepared from the product of example 20 step (iv) and benzylamine by the method of example 20 step (v).

1H NMR DMSO-d6: δ13.09 (1H, brs); 8.54 (2H, s); 7.90 (1H, t); 7.42 (1H, d); 7.35-7.29 (5H, m); 7.22 (1H, m); 7.03 (1H, d); 4.76 (2H, s); 4.55 (2H, d)

MS: APCI(−ve) 368 (M−1)

EXAMPLE 24

[4-Chloro-2-(2-piperidin-1-ylpyrimidin-5-yl)phenoxy]acetic acid

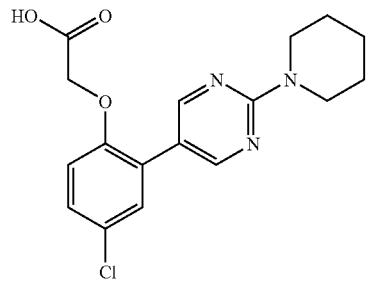

The title compound was prepared from the product of example 20 step (iv) and piperidine by the method of example 20 step (v).

1H NMR DMSO-d6: δ13.10 (1H, brs); 8.59 (1H, d); 7.32 (1H, dd); 7.04 (1H, d); 4.77 (2H, s); 3.79 (4H, t); 1.65 (2H, m); 1.53 (4H, m)

MS: APCI(−ve) 346 (M−1)

EXAMPLE 25

(4-Chloro-2-{2-[methyl(methylsulfonyl)amino]pyrimidin-5-yl}phenoxy)acetic acid

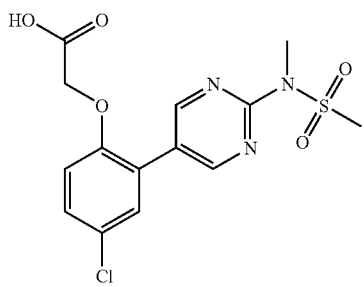

(i) N-(5-Bromopyrimidin-2-yl)-N-methylmethanesulfonamide

Sodium hydride (0.22 g, 60% in oil) was added to a solution of (5-bromopyrimidin-2-yl)methylamine (0.85 g) in DMF (10 ml) at 0° C. and stirred for 30 min. Methanesulphonyl chloride (0.62 g) was added dropwise, the mixture warmed to RT and stirred for a further 2 h. The reaction was quenched with water and then extracted with EtOAc. The organics were washed with water, dried, and evaporated under reduced pressure. The residue was purified by chromatography on silica eluting with 1% methanol/DCM. Yield 0.42 g MS: APCI (+ve): 266 (M+1)

(ii) N-[5-(5-Chloro-2-hydroxyphenyl)pyrimidin-2-yl]-N-methylmethanesulfonamide The subtitle compound was prepared by the method of example 1 step (ii) using the product from step (i) and 2-hydroxy-5-chloroboronic acid (0.27 g). Yield 0.2 g MS: APCI (+ve): 314 (M+1)

(iii) (4-Chloro-2-{2-[methyl(methylsulfonyl)amino]pyrimidin-5-yl}phenoxy)acetic acid The title compound was prepared by the method of example 1 step (i) and (iii) using the product from step (ii). Yield 0.017 g $^1$H NMR DMSO-d6: δ 13.16 (1H, s); 8.94 (2H, s); 7.57 (1H, d); 7.45-7.42 (1H, m); 7.14 (1H, d); 4.82 (2H, s); 3.55 (3H, s); 3.47 (3H, s)

MS: APCI (−ve): 370 (M−1)

EXAMPLE 26

[[2',5-Dichloro-4'-(ethylsulfonyl)[1,1'-biphenyl]-2-yl]oxy]-acetic acid

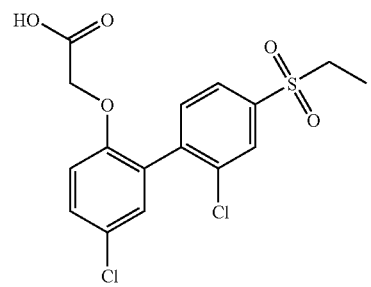

(i) 2-Chloro-4-(ethylthio)-1-iodo-benzene

A solution of 3-chloro-4-iodo-aniline (5.6 g), isoamylnitrite (8.8 ml) and ethyldisulphide (13.4 ml) in acetonitrile (100 ml) was heated at 60° C. for 24 h. The solvent was removed under reduced pressure and the residue purified by chromatography on silica eluting with 1% ethylacetate/isohexane. Yield 4.02 g $^1$H NMR CDCl$_3$: δ 7.70 (1H, d); 7.36 (1H, d); 6.87 (1H, dd); 2.94 (2H, q); 1.32 (3H, t)

(ii) [[[2',5-Dichloro-4'-(ethylthio)[1,1'-biphenyl]-2-yl]oxy]methyl]-benzene The subtitle compound was prepared by the method of example 1 step (ii) using the product from step (i) and the product from example 16 step (ii). Yield 3.64 g $^1$H NMR CDCl$_3$: δ 7.4 (1H, s); 7.32-7.18 (9H, m); 6.92 (1H, d); 5.03 (2H, s); 2.99 (2H, q); 1.36 (3H, t)

(iii) [[[2',5-Dichloro-4'-(ethylsulfonyl)[1,1'-biphenyl]-2-yl]oxy]methyl]-benzene The subtitle compound was prepared by the method of example 2 step (i) using the product from step (ii). Yield 3.8 g $^1$H NMR CDCl$_3$: δ 8.00 (1H, s); 7.81 (1H, d); 7.48 (1H, d); 7.36-7.20 (7H, m); 6.95 (1H, d); 5.04 (2H, s); 3.16 (2H, q); 1.32 (3H, t)

(iv) 2',5-Dichloro-4'-(ethylsulfonyl)-[1,1'-biphenyl]-2-ol

The subtitle compound was prepared by the method of example 16 step (iv) using the product from step (iii). Yield 2.44 g $^1$H NMR CDCl$_3$: δ 8.03 (1H, s); 7.85 (1H, d); 7.55 (1H, d); 7.30 (1H, d); 7.16 (1H, s); 6.92 (1H, d); 5.20 (2H, s); 3.17 (2H, q); 1.36 (3H, t)

(v) [[2',5-Dichloro-4'-(ethylsulfonyl)[1,1'-biphenyl]-2-yl]oxy]-acetic acid, ethyl ester The subtitle compound was prepared by the method of example 1 step (i) using the product from step (iv) and ethylbromoacetate. Yield 2.23 g (vi) [[2',5-Dichloro-4'-(ethylsulfonyl)[1,1'-biphenyl]-2-yl]oxy]-acetic acid A mixture of the product from step (v) (2.23 g), 1M aqueous sodium hydroxide (10 ml) and THF (20 ml) was stirred at RT for 3 h. The mixture was acidified with 2M hydrochloric acid, extracted with diethylether and the organics washed with water, dried, and evaporated under reduced pressure. The residue was recrystallised from ethylacetate/isohexane, yield 0.45 g.

$^1$H NMR CDCl$_3$: δ 13.02 (1H, s); 8.02 (1H, s); 7.89 (1H, d); 7.69 (1H, d); 7.48 (1H, dd); 7.34 (1H, d); 7.08 (1H, d); 4.70 (2H, s); 3.44 (2H, q); 1.16 (3H, t)

MS: APCI (−ve): 387/9 (M−1)

Mpt. 163-4° C.

EXAMPLE 27

[[2'-Chloro-4'-(ethylsulfonyl)-5-(trifluoromethyl)[1,1'-biphenyl]-2-yl]oxy]-acetic acid

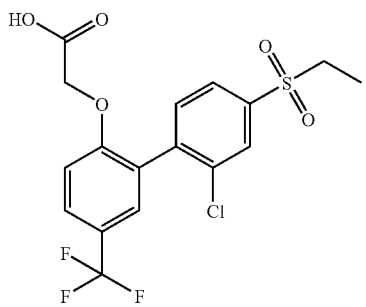

(i) 2-Bromo-1-(phenylmethoxy)-4-(trifluoromethyl)-benzene

The subtitle compound was prepared by the method of example 16 step (i) using 2-bromo-4-trifluoromethylphenol. Yield 58.7 g $^1$H NMR CDCl$_3$: δ 7.83 (1H, s); 7.51-7.32 (6H, m); 6.98 (1H, d); 5.21 (2H, s)

(ii) [2-(Phenylmethoxy)-5-(trifluoromethyl)phenyl]-boronic acid

The subtitle compound was prepared by the method of example 16 step (ii) using the product from step (i). Yield 30.7 g $^1$H NMR CDCl$_3$: δ 8.14 (1H, d); 7.68 (1H, dd); 7.44-7.39 (5H, m); 7.05 (1H, d); 5.79 (2H, s); 5.20 (2H, s)

(iii) [2-Hydroxy-5-(trifluoromethyl)phenyl]-boronic acid

The subtitle compound was prepared by the method of example 16 step (iv) using the product from step (ii). Yield 3.54 g (iv) 2'-Chloro-4'-(ethylthio)-5-(trifluoromethyl)-[1,1'-biphenyl]-2-ol A mixture of palladium acetate (0.045 g) and tri-p-tolylphosphine (0.213 g) in methanol (10 ml) was stirred at RT for 30 min. The product from step (iii) (1 g), sodium carbonate (1.27 g), the product from example (26) step (i) (1.19 g) and methanol (20 ml) were added and the mixture heated under reflux for 6 h. The solvent was removed under reduced pressure and the residue partitioned between diethylether and 2M hydrochloric acid. The organics were separated, dried and evaporated under reduced pressure. The residue was purified by chromatography on silica eluting with 10% ethylacetate/isohexane. Yield 0.503 g MS: ESI (−ve): 331/3 (M−1)

(v) 2'-Chloro-4'-(ethylsulfonyl)-5-(trifluoromethyl)-[1,1'-biphenyl]-2-ol

The subtitle compound was prepared by the method of example 2 step (i) using the product from step (iv). Yield 0.277 g MS: ESI (−ve): 363/5 (M−1)

(vi) [[2'-chloro-4'-(ethylsulfonyl)-5-(trifluoromethyl)[1,1'-biphenyl]-2-yl]oxy]-acetic acid, 1,1-dimethylethyl ester The subtitle compound was prepared by the method of example 1 step (i) using the product from step (v). Yield 0.253 g (vii) [[2'-Chloro-4'-(ethylsulfonyl)-5-(trifluoromethyl)[1,1'-biphenyl]-2-yl]oxy]-acetic acid The title compound was prepared by the method of example 1 step (iii) using the product from step (vi). Yield 0.154 g $^1$H NMR CDCl$_3$: δ 13.12 (1H, s); 8.04 (1H, s); 7.91 (1H, d); 7.81 (1H, d); 7.72 (1H, d); 7.63 (1H, s); 7.25 (1H, d); 4.82 (2H, s); 3.45 (2H, q); 1.17 (3H, t)

MS: APCI (−ve): 421/3 (M−1)

Mpt. 167° C.

EXAMPLE 28

[[5-Chloro-4'-(ethylsulfonyl)-2'-fluoro[1,1'-biphenyl]-2-yl]oxy]-acetic acid

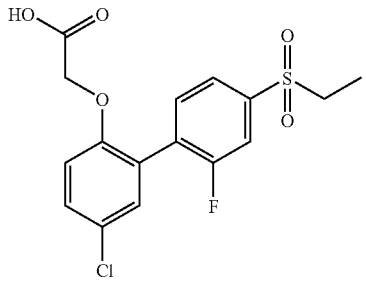

(i) 1-Bromo-4-(ethylthio)-2-fluoro-benzene

Bromine (0.3 ml) was added to a solution of 1-ethylsulfanyl-3-fluoro-benzene (1 g) in chloroform (20 ml) at 0° C. then warmed to RT. After 2 h the mixture was diluted with DCM, washed with aq. sodium thiosulphate solution, dried, and evaporated under reduced pressure. The residue was purified by chromatography on silica eluting with 10% diethylether/iso-hexane. Yield 1.2 g ¹H NMR CDCl₃: δ 7.44-6.93 (3H, m); 2.99-2.90 (2H, q); 1.42-1.30 (3H, t).

(ii) 1-Bromo-4-(ethylsulfonyl)-2-fluoro-benzene

The subtitle compound was prepared by the method of example 2 step (i) using the product from step (i). Yield 0.94 g ¹H NMR CDCl₃: δ7.81-7.07 (3H, m); 3.17-3.10 (2H, q); 1.32-1.19 (3H, t).

(iii) [[[5-Chloro-4'-(ethylsulfonyl)-2'-fluoro[1,1'-biphenyl]-2-yl]oxy]methyl]-benzene The subtitle compound was prepared by the method of example 1 step (ii) using the product from step (ii) and the product from example 16 step (ii). Yield 0.55 g ¹H NM CDCl₃: δ7.73-6.96 (11H, m); 5.09 (2H, s); 3.19-3.13 (2H, q); 1.33-1.27 (3H, t).

(iv) 5-Chloro-4'-(ethylsulfonyl)-2'-fluoro-[1,1'-biphenyl]-2-ol

The subtitle compound was prepared by the method of example 16 step (iv) using the product from step (ii), yield 0.35 g MS: ESI (−ve) 313 (M−1)

(v) [[5-Chloro-4'-(ethylsulfonyl)-2'-fluoro[1,1'-biphenyl]-2-yl]oxy]-acetic acid The title compound was prepared by the method of example 1 step (i) and step (iii) using the product from step (iv), yield 0.205 g ¹H NMR DMSO-d6: δ 7.81-7.08 (6H, m); 4.73 (2H, s); 3.44-3.39 (2H, q); 1.17-1.14 (3H, t).

MS: ESI (−ve) 371 (M−1)

EXAMPLE 29

[[4'-(Ethylsulfonyl)-2'-fluoro-5-(trifluoromethyl)[1,1'-biphenyl]-2-yl]oxy]-acetic acid, sodium salt

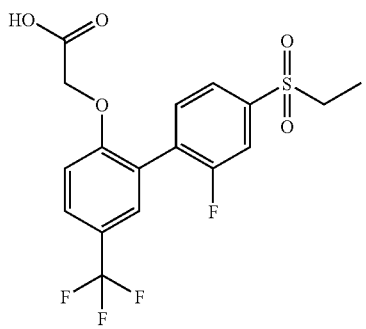

The title compound was prepared by the method of example 28, yield 0.26 g.

¹H NMR DMSO-d6: δ 7.96-7.57 (5H, m); 7.09-7.07 (1H, d); 4.31 (2H, s); 3.44-3.35 (2H, q); 1.18-1.14 (3H, t).

MS: ESI (−ve) 405 (M−1)

EXAMPLE 30

[[5-Chloro-4'-(ethylsulfonyl)-2'-(trifluoromethyl)[1,1'-biphenyl]-2-yl]oxy]acetic acid

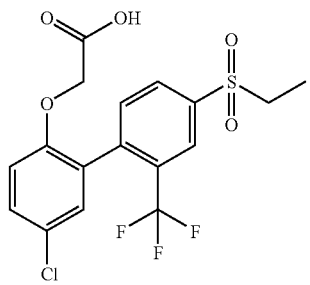

(i) 1-Bromo-4-(ethylthio)-2-(trifluoromethyl)-benzene

Iodoethane (0.84 ml) was added to a stirred solution of 3-trifluoromethyl-thiophenol (2 g) and potassium carbonate (1.42 g) in DMF (20 ml). After 72 h the mixture was partitioned between diethylether and water, the organics separated, dried and evaporated under reduced pressure. The residue was dissolved in acetic acid (20 ml), cooled to 0° C., then bromine (0.51 ml) added. The mixture was stirred at RT for 16 h, the solvent removed under reduced pressure and the residue purified by chromatography on silica eluting with 25% DCM/iso-hexane. Yield 2.05 g (ii) 5-Chloro-4'-(ethylthio)-2'-(trifluoromethyl)-[1,1'-biphenyl]-2-ol The subtitle compound was prepared by the method of example 1 step (ii) using the product from step (i) and 5-chloro-2-hydroxyphenyl-boronic acid, yield 0.26 g MS: ESI (−ve) 347 (M−1)

(iii) [[5-Chloro-4'-(ethylthio)-2'-(trifluoromethyl)[1,1'-biphenyl]-2-yl]oxy]-acetic acid, 1,1-dimethylethyl ester The subtitle compound was prepared by the method of example 1 step (i) using the product from step (ii), yield 0.26 g MS: APCI (−ve) 389/391 (M−1)-t-butyl (iv) [[5-Chloro-4'-(ethylsulfonyl)-2'-(trifluoromethyl)[1,1'-biphenyl]-2-yl]oxy]-acetic acid The title compound was prepared by the method of example 2 step (i) and example 1 step (iii) using the product from step (iii), yield 0.045 g ¹H NMR DMSO-d6: δ 7.62-7.01 (6H, m); 4.69-4.66 (2H, s); 4.20-4.10 (2H, q), 1.40-1.35 (3H, t).

MS: ESI (−ve) 421 (M−1)

EXAMPLE 31

2-[[5-Chloro-4'-(ethylsulfonyl)[1,1'-biphenyl]-2-yl]oxy]-propanoic acid

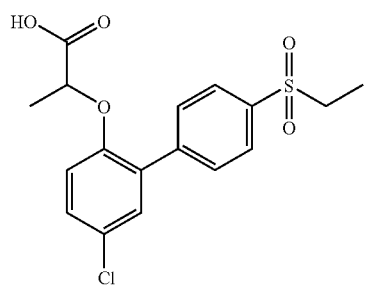

(i) 2-(2-Bromo-4-chlorophenoxy)-propanoic acid, 1,1-dimethylethyl ester

The subtitle compound was prepared by the method of example 1 step (i) using 2-bromo-4-chlorophenol and 2-bromopropionic acid, tert-butyl ester, yield 1.1 g ¹H NMR DMSO-d6: δ 7.54-7.16 (2H, m); 6.74-6.71 (1H, d); 3.70 (3H, s); 1.78-1.76 (1H, d); 1.48 (9H, s).

(ii) 2-[[5-Chloro-4'-(ethylthio)[1,1'-biphenyl]-2-yl]oxy]-propanoic acid, 1,1-dimethylethyl ester The subtitle compound was prepared by the method of example 1 step (ii) using the product from step (i) and 4-(ethylthio)benzeneboronic acid, yield 1.2 g.

MS: APCI (−ve) 336 (M−1)-t-butyl (iii) 2-[[5-Chloro-4'-(ethylsulfonyl)[1,1'-biphenyl]-2-yl]oxy]-propanoic acid The title compound was prepared by the method of example 2 step (i) and example 1 step (iii) using the product from step (ii), yield 0.08 g ¹H NMR DMSO-d6: δ 7.97-6.96 (7H, m); 4.79-4.76 (1H, m); 3.39-3.31 (2H, t); 1.39-1.37 (3H, d); 1.16-1.07 (3H, t).

MS: ESI (−ve) 367 (M−1)

EXAMPLE 32

2-[[4'-(Ethylsulfonyl)-2'-methyl-5-(trifluoromethyl)[1,1'-biphenyl]-2-yl]oxy]-(2S)-propanoic acid

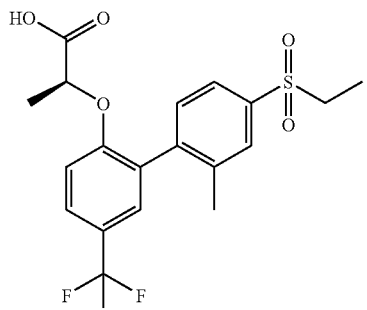

(i) 1-Bromo-4-(ethylsulfonyl)-2-methyl-benzene

The subtitle compound was prepared by the method of example 2 step (i) using the product from example 10 step (i), yield 4.3 g.

MS: ESI (+ve) 264 (M+1)

(ii) [2-(Phenylmethoxy)-5-(trifluoromethyl)phenyl]-boronic acid

The subtitle compound was prepared by the method of example 16 step (ii) using the product from example 27 step (i), yield 5.5 g.

¹H NMR CDCl₃: δ 8.14-7.62 (2H, m); 7.43-7.38 (5H, m); 7.01 (1H, m); 5.67 (2H, s); 5.19-5.16 (2H, s)

(iii) [[[4'-(Ethylsulfonyl)-2'-methyl-5-(trifluoromethyl)[1,1'-biphenyl]-2-yl]oxy]methyl]-benzene The subtitle compound was prepared by the method of example 1 step (ii) using the product from step (i) and (ii), yield 2.72 g.

MS: ESI (+ve) 452 (M+1+NH₃)

(iv) 4'-(Ethylsulfonyl)-2'-methyl-5-(trifluoromethyl)-[1,1'-biphenyl]-2-ol

The subtitle compound was prepared by the method of example 16 step (iv) using the product from step (iii), yield 2.1 g.

MS: ESI (+ve) 362 (M+1+NH₃)

(v) 2-[[4'-(Ethylsulfonyl)-2'-methyl-5-(trifluoromethyl)[1,1'-biphenyl]-2-yl]oxy]-(2S)-propanoic acid, methyl ester Diethyl azodicarboxylate (0.14 ml) was added to a stirred solution of the product from step (iv) (0.3 g), methyl-R-lactate (0.083 ml) and triphenylphosphine (0.228 g) in THF (10 ml) at 0° C. After 4 h, the mixture was diluted with water and extracted with ethylacetate, the organics separated, dried and evaporated under reduced pressure. The residue was purified by chromatography on silica eluting with 50% diethylether/iso-hexane. Yield 0.4 g MS: ESI (+ve) 448 (M+1+NH₃)

(vi) 2-[[4'-(Ethylsulfonyl)-2'-methyl-5-(trifluoromethyl)[1,1'-biphenyl]-2-yl]oxy]-(2S)-propanoic acid A mixture of the product from step (v) (0.4 g) and lithium hydroxide (2 equiv) in THF (10 ml) and water (10 ml) was stirred at RT overnight. The mixture was partitioned between ethylacetate/water, the aqueous layer was acidified with 2M hydrochloric acid and extracted with ethyl acetate. The organic layer was dried, evaporated under reduced pressure and the residue purified by reverse phase HPLC. Yield 0.035 g $^1$H NMR DMSO-d6: δ 7.78-7.44 (5H, m); 7.16-7.14 (1H, d); 4.91-4.86 (1H, q); 3.30-3.25 (2H, q); 2.22 (3H, s); 1.33-1.24 (3H, d); 1.10-1.07 (3H, t).

MS: ESI (+ve) 434 (M+1+NH$_3$)

EXAMPLE 33

2-[[4'-(Ethylsulfonyl)-2'-methyl-5-(trifluoromethyl)[1,1'-biphenyl]-2-yl]oxy]-(2R)-propanoic acid, sodium salt

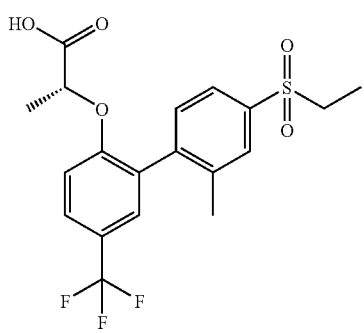

The title compound was prepared by the method of example 32 using methyl-S-lactate, yield 0.2 g.

$^1$H NMR DMSO-d6: δ7.77-7.38 (5H, m); 7.02-7.00 (1H, d); 4.32 (1H, m); 3.39-3.25 (2H, q); 2.32 (3H, s); 1.21-1.07 (6H, d+t).

MS: ESI (+ve) 434 (M+1+NH$_3$)

EXAMPLE 34

2-[[2',5-Dichloro-4'-(ethylsulfonyl)[1,1'-biphenyl]-2-yl]oxy]-(2S)-propanoic acid, sodium salt

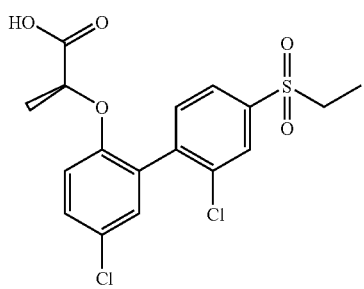

The title compound was prepared by the method of example 32 step (v) and (vi) using the product from example 26 step (iv), yield 0.18 g.

$^1$H NMR DMSO-d6: δ 7.99-7.23 (5H, m); 6.93-6.91 (1H, d); 4.26-4.24 (1H, q); 3.46-3.37 (2H, q); 1.20-1.06 (6H, d+t).

MS: ESI (−ve) 402/403 (M−1)

EXAMPLE 35

2-[[2'-Chloro-4'-(ethylsulfonyl)-S-(trifluoromethyl)[1,1'-biphenyl]-2-yl]oxy]-(2S)-propanoic acid

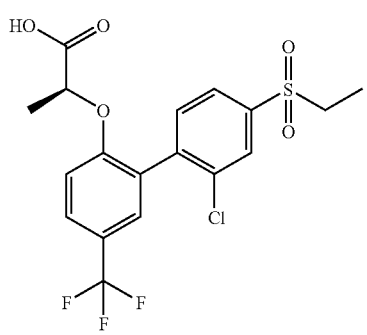

The title compound was prepared by the method of example 32 step (v) and (vi) using the product from example 2 step (v), yield 0.05 g.

$^1$H NMR DMSO-d6: δ 7.98-7.23 (5H, m); 6.93-6.91 (1H, d); 4.68 (1H, m); 3.20-3.15 (2H, q); 1.48-1.39 (3H, m); 1.34-1.30 (3H, t).

MS: ESI (−ve) 436 (M−1)

EXAMPLE 36

2-[[4'-(Ethylsulfonyl)-2'-methyl-5-(trifluoromethyl)[1,1'-biphenyl]-2-yl]oxy]-2-methyl-propanoic acid, sodium salt

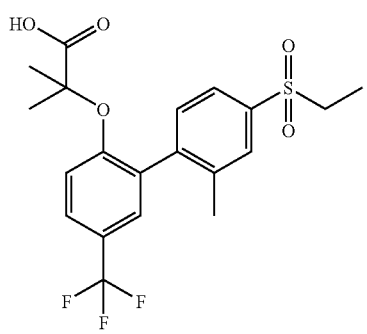

The title compound was prepared by the method of example 1 step (i) and example 26 step (vi) using the product from example 34 step (iv), yield 0.18 g.

$^1$H NMR DMSO-d6: δ 7.72 (1H, s); 7.71 (1H, d); 7.56 (1H, d); 7.44 (1H, d); 7.35 (1H, s); 7.10 (1H, d); 2.29 (3H, s); 1.38 (6H, s); 1.13 (3H, t)

MS: ESI (−ve) 429 (M−1)

EXAMPLE 37

2-[[4'-(Ethylsulfonyl)-2'-methyl-5-(trifluoromethyl)[1,1'-biphenyl]-2-yl]oxy]-butanoic acid, sodium salt

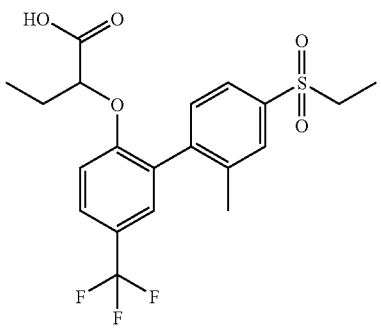

The title compound was prepared by the method of example 1 step (i) and example 26 step (vi) using the product from example 34 step (iv), yield 0.29 g.

$^1$H NMR DMSO-d6: δ 7.78 (1H, s); 7.71 (1H, d); 7.64 (1H, d); 7.41 (1H, s); 7.01 (1H, d); 4.27 (1H, brs); 3.36 (2H, q) 2.33 (3H, brs); 1.64-1.55 (2H, m); 1.11 (3H, t); 0.66 (3H, brs)

MS: ESI (−ve) 429 (M−1)

EXAMPLE 38

[4-Chloro-2-[2-[(methylsulfonyl)(phenylmethyl)amino]-5-pyrimidinyl]phenoxy]-acetic acid

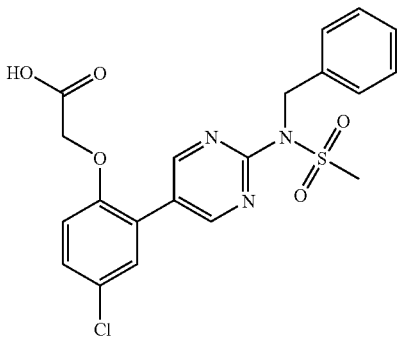

(i) N-(5-Bromo-2-pyrimidinyl)-N-(phenylmethyl)-methanesulfonamide

Sodium hydride (0.1 g, 60% disp. in oil) was added to a stirred solution of benzyl-(5-bromo-pyrimidin-2-yl)-amine (0.55 g) in DMF (8 ml) at 0° C. After 30 min methanesulphonyl chloride (0.286 g) was added and the mixture stirred at RT for 2 h then partitioned between ethyl acetate and water. The organics were separated washed with water, dried and evaporated under reduced pressure. The residue was purified by chromatography on silica eluting with dichloromethane. Yield 0.41 g MS: APCI (+ve) 344 (M+1)

(ii) N-[5-(5-Chloro-2-hydroxyphenyl)-2-pyrimidinyl]-N-(phenylmethyl)-methanesulfonamide The subtitle compound was prepared by the method of example 1 step (ii) using the product from step (i) and 5-chloro-2-hydroxyphenyl-boronic acid, yield 0.25 g.

MS: APCI (+ve) 390 (M+1)

(iii) [4-Chloro-2-[2-[(methylsulfonyl)(phenylmethyl)amino]-5-pyrimidinyl]phenoxy]-acetic acid The title compound was prepared by the method of example 1 step (i) and step (iii) using the product from step (ii), yield 0.07 g.

$^1$H NMR DMSO-d6: δ 13.16 (1H, s); 8.93 (2H, s); 7.56 (1H, d); 7.44-7.41 (1H, m); 7.37-7.31 (4H, m); 7.27-7.23 (1H, m); 7.12 (1H, d); 5.28 (2H, s); 4.81 (2H, s); 3.59 (3H, s).

MS: APCI (−ve): 446 (M−1)

EXAMPLE 39

[4-Chloro-2-[2-[(ethylsulfonyl)(phenylmethyl)amino]-5-pyrimidinyl]phenoxy]-acetic acid

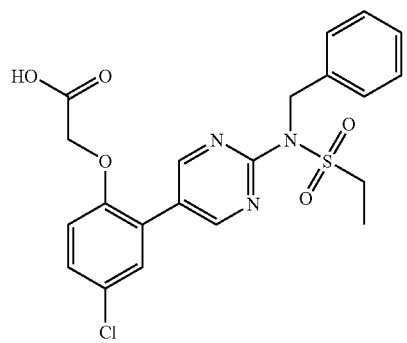

(i) N-(5-Bromo-2-pyrimidinyl)-N-(phenylmethyl)-ethanesulfonamide

The subtitle compound was prepared by the method of example 38 step (i) using benzyl-(5-bromo-pyrimidin-2-yl)-amine and ethanesulphonyl chloride, yield 0.31 g.

MS: APCI (+ve) 358 (M+1)

(ii) N-[5-(5-Chloro-2-hydroxyphenyl)-2-pyrimidinyl]-N-(phenylmethyl)-ethanesulfonamide The subtitle compound was prepared by the method of example 1 step (ii) using the product from step (i) and 5-chloro-2-hydroxyphenyl-boronic acid, yield 0.25 g.

MS: APCI (+ve) 404 (M+1)

(iii) [4-Chloro-2-[2-[(ethylsulfonyl)(phenylmethyl)amino]-5-pyrimidinyl]phenoxy]-acetic acid The title compound was prepared by the method of example 1 step (i) and step (iii) using the product from step (ii), yield 0.13 g.

$^1$H NMR DMSO-d6: δ 13.14 (1H, s); 8.92 (2H, s); 7.56 (1H, d); 7.44-7.31 (5H, m); 7.27-7.23 (1H, m); 7.12 (1H, d); 5.27 (2H, s); 4.81 (2H, s); 3.87 (2H, q); 1.25 (3H, t).

MS: APCI (−ve): 460 (M−1)

EXAMPLE 40

[2-[2-[Acetyl(phenylmethyl)amino]-5-pyrimidinyl]-4-chlorophenoxy]-acetic acid

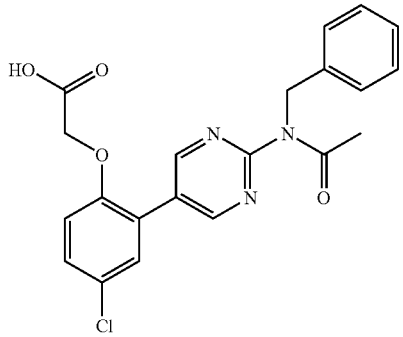

(i) N-(5-Bromo-2-pyrimidinyl)-N-(phenylmethyl)-acetamide

The subtitle compound was prepared by the method of example 38 step (i) using benzyl-(5-bromo-pyrimidin-2-yl)-amine and acetylchloride, yield 0.21 g.
MS: APCI (+ve) 306 (M+1)

(ii) N-[5-(5-Chloro-2-hydroxyphenyl)-2-pyrimidinyl]-N-(phenylmethyl)-acetamide The subtitle compound was prepared by the method of example 1 step (ii) using the product from step (i) and 5-chloro-2-hydroxyphenyl-boronic acid, yield 0.16 g.
MS: APCI (+ve) 354 (M+1)

(iii) [2-[2-[Acetyl(phenylmethyl)amino]-5-pyrimidinyl]-4-chlorophenoxy]-acetic acid The title compound was prepared by the method of example 1 step (i) and step (iii) using the product from step (ii), yield 0.08 g.
$^1$H NMR DMSO-d6: δ 9.01 (2H, s); 7.59 (1H, d); 7.44 (1H, q); 7.30-7.18 (5H, m); 7.13 (1H, d); 5.26 (2H, s); 4.81 (2H, s); 2.45 (3H, s).
MS: APCI (+ve): 412 (M+1)

EXAMPLE 41

[[4'-(Ethylsulfonyl)-5-fluoro-2'-methyl[1,1'-biphenyl]-2-yl]oxy]-acetic acid

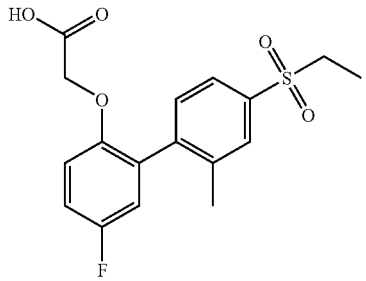

(i) [4-(Ethylthio)-2-methylphenyl]-boronic acid

A 100 ml portion of a solution of the product from example 10 step (i) (120.7 g) in THF (500 ml) was added to a stirred mixture of magnesium turnings (13.4 g) in THF (100 ml). Dibromoethane (0.2 ml) was added, and the mixture gently refluxed on initiation. The remaining bromide solution was added dropwise maintaining the reaction at reflux. After addition the mixture was allowed to cool to RT then transferred via cannula into a stirred solution of trimethylborate (112 ml) in TIE (200 ml) at 0° C. The mixture was warmed to RT, stirred for 2 h then quenched with 2M hydrochloric acid (300 ml). After stirring at RT for 18 h the THF was removed under reduced pressure and the mixture extracted with diethylether. The organics were separated, washed with water, dried and evaporated under reduced pressure. The residue was triturated with diethylether/isohexane and filtered. Yield 53.02 g
$^1$H NMR CDCl$_3$: δ 8.08 (1H, d); 7.18 (1H, d); 7.15 (1H, s); 3.04 (2H, q); 2.76 (3H, s); 1.38 (3H, t)

(ii) (2-Bromo-4-fluorophenoxy)-acetic acid, 1,1-dimethylethyl ester

The subtitle compound was prepared by the method of example 1 step (i).

(iii) [[4'-(Ethylsulfonyl)-5-fluoro-2'-methyl[1,1'-biphenyl]-2-yl]oxy]-acetic acid The title compound was prepared by the method of example 27 step (iv), example 2 step (i) and example 1 step (iii) using the products from step (i) and (ii), yield 0.045 g.
$^1$H NMR DMSO-d6: δ 7.8-7.64 (2H, m); 7.42 (2H, d); 7.8-6.0 (3H, m); 4.10 (2H, s); 3.20 (2H, q); 1.18 (3H, t)
MS: APCI (–ve): 351 (M–1)

EXAMPLE 42

[[4'-(Ethylsulfonyl)-4,5-difluoro-2'-methyl[1,1'-biphenyl]-2-yl]oxy]-acetic acid

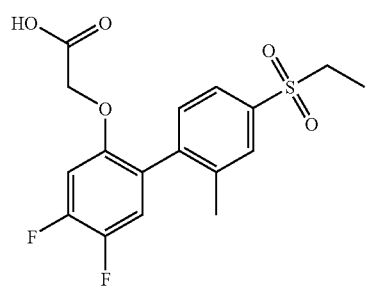

The title compound was prepared by the method of example 41, yield 0.081 g.
$^1$H NMR DMSO-d6: δ 7.76 (1H, s); 7.71 (1H, dd); 7.44 (1H, d); 7.23 (1H, t); 7.01-6.94 (1H, m); 4.32 (2H, s); 3.39 (2H, m); 2.25 (3H, s); 1.18 (3H, t)
MS: APCI (–ve): 369 (M–1)

EXAMPLE 43

[[4'-(Ethylsulfonyl)-3,5-difluoro-2'-methyl[1,1'-biphenyl]-2-yl]oxy]-acetic acid

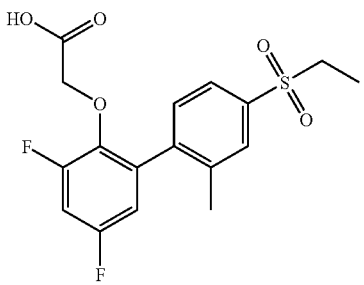

The title compound was prepared by the method of example 41, yield 0.15 g.

$^1$H NMR DMSO-d6: δ 7.82-7.70 (2H, m); 7.49-7.38 (2H, m); 7.02-6.90 (1H, m); 4.40 (2H, d); 3.34 (2H, q); 1.11 (3H, t)

EXAMPLE 44

[2-(2-Amino-5-methyl-3-pyridinyl)-4-(trifluoromethyl)phenoxy]-acetic acid

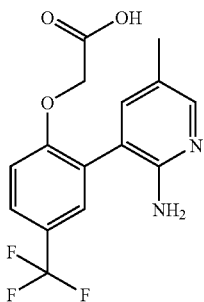

(i) [4-(Trifluoromethyl)phenoxy]-acetic acid

Sodium hydride (2.96 g, 60% disp. in oil) was added to a stirred solution of 4-hydroxybenzo-trifluoride (10 g) in tetrahydrofuran (150 ml) at −78° C. The cooling bath was removed, the mixture stirred for 1 h then methyl bromoacetate (7 ml) added. After 1 h, water was added, the tetrahydrofuran evaporated off under reduced pressure and the residue partitioned between ethyl acetate/2M hydrochloric acid. The organic layer was evaporated under reduced pressure and the residue dissolved in tetrahydrofuran (120 ml). Methanol (30 ml), water (30 ml) and conc. sodium hydroxide solution (6 ml) was added and the mixture stirred at RT overnight. The organics were removed under reduced pressure and the residue partitioned between ethylacetate and 2M hydrochloric acid. The organics were separated, dried and evaporated under reduced pressure, yield 12.42 g $^1$H NMR DMSO-d6: δ 13.13 (1H, s); 7.65 (2H, d); 7.10 (2H, d); 4.80 (2H, s).

MS: APCI (−ve) 219 (M−1)

(ii) [4-(Trifluoromethyl)phenoxy]-acetic acid, (3-methyl-3-oxetanyl)methyl ester Oxalyl chloride (14 ml) was added to a solution of the product from step (i) (12.42 g) and N,N-dimethylformamide (2 drops) in dichloromethane (100 ml), and stirred at RT for 72 h. The mixture was evaporated under reduced pressure, the residue dissolved in dichloromethane (100 ml) then triethylamine (20 ml) and 3-methyl-3-oxetanemethanol (17 ml) added. After 2 h the mixture was washed with water, evaporated under reduced pressure and the residue purified by chromatography on silica eluting with dichloromethane, yield 14.2 g.

$^1$H NMR DMSO-d6: δ 7.66 (2H, d); 7.14 (2H, d); 4.98 (2H, s), 4.34 (2H, d); 4.24 (2H, s); 4.19 (2H, d), 1.21 (3H, s).

(iii) 4-Methyl-1-[[4-(trifluoromethyl)phenoxy]methyl]-2,6,7-trioxabicyclo[2.2.2]octane Boron trifluoride diethyl etherate (1.48 ml) was added to a solution of the product from step (ii) (14.2 g) in dichloromethane at −78° C. The cooling bath was removed, the mixture, stirred for 3 h then triethylamine (6.2 ml) added. The mixture was reduced to half the volume under reduced pressure then filtered. The filtrate was evaporated under reduced pressure then the residue purified by chromatography on silica (pre-eluted with one column volume of neat triethylamine) eluting with dichloromethane, yield 11.1 g.

$^1$H NMR DMSO-d6: δ 7.62 (2H, d); 7.14 (2H, d); 4.04 (2H, s); 3.91 (6H, s); 0.77 (3H, s).

MS: APCI (+ve) 305 (M+1)

(iv) [2-Borono-4-(trifluoromethyl)phenoxy]-acetic acid

A solution of sec-butyllithium (66 ml, 1.4M in cyclohexane) was added dropwise over 10 min to a stirred solution of the product from step (iii) (9.44 g) in THF (100 ml) at −78° C. After 3 h the mixture was warmed to −40° C. for 5 min, then cooled to −78° C. Trimethylborate (14.1 ml) was added, then after 10 min the reaction quenched with 2M hydrochloric acid. The mixture was warmed to RT and the organic phase separated. The aqueous layer was extracted with ethylacetate, the organics combined and evaporated under reduced pressure. The residue was dissolved in methanol (500 ml) then bondelut-NH$_2$ resin(180 g) added and the mixture swirled for 0.5 h then filtered. The resin was washed with 10% acetic acid/methanol, the washings then evaporated under reduced pressure and dried under high vacuum. The residue was dissolved in methanol (50 ml), tetrahydrofuran (50 ml) and saturated aqueous sodium hydroxide solution (2 ml), left for 30 min then 2M hydrochloric acid (50 ml) added and the organics evaporated under reduced pressure. The residual aqueous layer was extracted with ethylacetate, the organics separated, dried and evaporated under reduced pressure, yield 5.05 g.

$^1$H NMR DMSO-d6: δ 8.07 (1H, s); 7.89 (1H, d); 7.75 (1H, dd); 7.14 (1H, d); 4.85 (2H, s).

MS: APCI (−ve) 263 (M−1)

(v) [2-(2-Amino-5-methyl-3-pyridinyl)-4-(trifluoromethyl)phenoxy]-acetic acid A mixture of the product from step (iv) (0.1 g), 2-amino-3-bromo-5-methylpyridine (0.071 g), tetrakis(triphenylphosphine)palladium(0) (0.046 g), sodium carbonate (0.12 g) in methanol (2 ml) was heated in a CEM microwave (variable wattage up to 150 W) at 100° C. for 10 min. The mixture was loaded onto SCX resin (sulphonic acid resin), flushed with methanol then the product eluted with methanol/ammonia. The methanol/ammonia filtrate was evaporated under reduced pressure then loaded onto bondelut-NH$_2$ resin. The resin was flushed with methanol then the product eluted with methanol/acetic acid. The methanol/acetic acid filtrate was evaporated and the residue purified by RPHPLC. Yield 0.089 g $^1$H NMR DMSO-d6: δ 7.87 (1H, s); 7.79 (1H, d); 7.69 (1H, s); 7.63 (1H, s); 7.26 (1H, d); 4.9 (2H, s); 2.2 (3H, s).
MS: APCI (−ve) 325 (M−1)

EXAMPLE 45-123

The following compounds were synthesised in an analogous method to example 44

EXAMPLE 45

[[4'-Amino-2'-methyl-5-(trifluoromethyl)[1,1'-biphenyl]-2-yl]oxy]-acetic acid

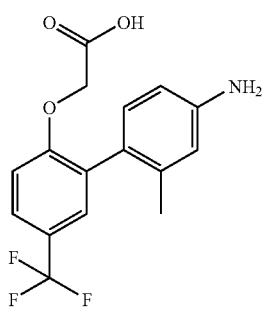

$^1$H NMR DMSO-d6: δ 7.62 (1H, d); 7.32 (1H, s); 7.05 (1H, d); 6.81 (1H, d); 6.47 (1H, s); 6.44 (1H, d); 4.74 (2H, s); 1.98 (3H, s).
MS: APCI (−ve) 324 (M−1)

EXAMPLE 46

[[4'-Amino-2'-chloro-5-(trifluoromethyl)[1,1'-biphenyl]-2-yl]oxy]-acetic acid

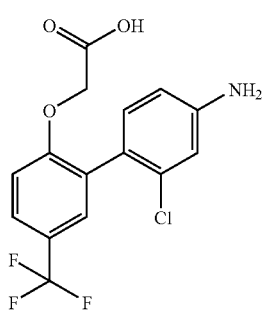

$^1$H NMR DMSO-d6: δ 7.65 (1H, d); 7.4 (1H, s), 7.15 (1H, d); 7.04 (1H, d); 6.7 (1h, s); 6.56 (1H, d); 4.76 (2H, s)
MS: APCI (−ve) 344/6 (M−1).

EXAMPLE 47

[[2'-Chloro-4'-hydroxy-5-(trifluoromethyl)[1,1'-biphenyl]-2-yl]oxy]-acetic acid

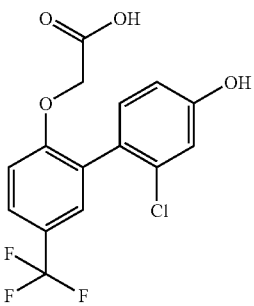

$^1$H NMR DMSO-d6: δ 9.98 (1H, s); 7.69 (1H, d); 7.44 (1H, s); 7.21 (1H, d); 7.14 (1H, d); 6.91 (1h, s); 6.80 (1H, d); 4.76 (2H, s).
MS: APCI (−ve) 345/7 (M−1)

EXAMPLE 48

[2-(2,4-Dimethoxy-5-pyrimidinyl)-4-(trifluoromethyl)phenoxy]-acetic acid

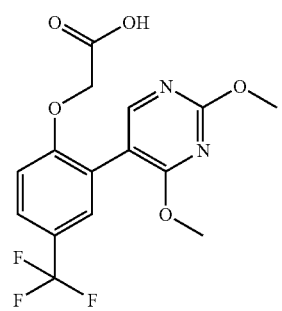

$^1$H NMR DMSO-d6: δ 8.32 (1H, s); 7.71 (1H, d); 7.63 (1H, s); 7.20 (1H, d); 4.8 (2H, s); 3.95 (3H, s); 3.87 (3H, s).
MS: APCI (−ve) 357 (M−1)

EXAMPLE 49

[[2'-Chloro-5-(trifluoromethyl)[1,1'-biphenyl]-2-yl]oxy]-acetic acid

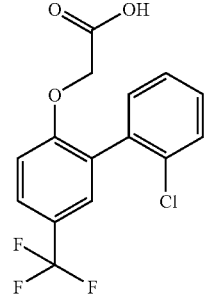

$^1$H NMR DMSO-d6: δ 7.75 (1H, d); 7.55 (1H, m), 7.50 (1H, s); 7.42 (1H, m); 7.41 (1H, d); 7.40 (1H, d); 7.19 (1H, d); 4.78 (2H, s).
MS: APCI (−ve) 219 (M−1)
MS: APCI (−ve) 329/31 (M−1)

EXAMPLE 50

[[2',5-Bis(trifluoromethyl)[1,1'-biphenyl]-2-yl]oxy]-acetic acid

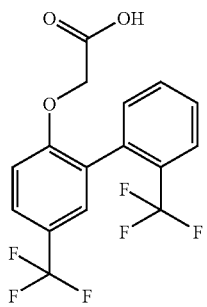

¹H NMR DMSO-d6: δ 7.83 (1H, d); 7.75 (1H, d); 7.71 (1H, d); 7.63 (1H, t); 7.44 (1H, s); 7.43 (1H, d); 4.74 (2H, m).
MS: APCI (−ve) 363 (M−1)

EXAMPLE 51

[[5'-Fluoro-2'-methoxy-5-(trifluoromethyl)[1,1'-biphenyl]-2-yl]oxy]-acetic acid

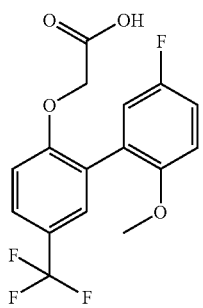

¹H NMR DMSO-d6: δ 7.68 (1H, d); 7.51 (1H, s); 7.20 (1H, d); 7.17 (1H, m); 7.15 (1H, m); 7.10 (1H, d); 4.78 (2H, s); 3.7 (3H, s).
MS: APCI (−ve) 343 (M−1)

EXAMPLE 52

[[5'-Cyano-2'-methoxy-5-(trifluoromethyl)[1,1'-biphenyl]-2-yl]oxy]-acetic acid

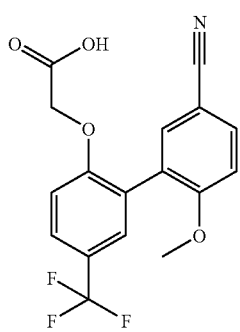

¹H NMR DMSO-d6: δ 7.87 (1H, d); 7.74 (1H, s); 7.71 (1H, d); 7.56 (1H, s); 7.29 (1H, d); 7.19 (1H, d); 4.77 (2H, s); 3.81 (3H, s)
MS: APCI (−ve) 350 (M−1).

EXAMPLE 53

[[4'-Chloro-2'-methyl-5-(trifluoromethyl)[1,1'-biphenyl]-2-yl]oxy]-acetic acid

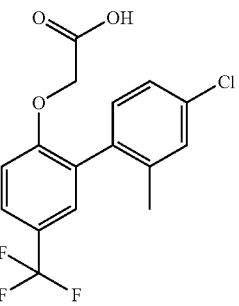

¹H NMR DMSO-d6: δ 7.71 (1H, d), 7.47 (1H, s), 7.34 (1H, d), 7.30 (1H, d), 7.24 (1H, s), 7.13 (1H, d), 4.73 (2H, s), 2.11 (3H, s)
MS: APCI (−ve) 343/345 (M−1)

EXAMPLE 54

[[2',5'-Dimethyl-5-(trifluoromethyl)[1,1'-biphenyl]-2-yl]oxy]-acetic acid

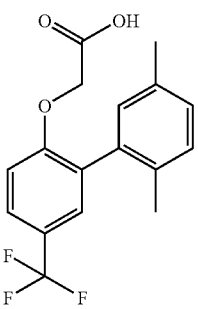

¹H NMR DMSO-d6: δ 7.64 (1H, d), 7.35 (1H, s), 7.13 (1H, d), 7.07 (1H, d), 7.02 (1H, d), 6.94 (1H, s), 4.50 (2H, s), 2.30 (3H, s), 2.08 (3H, s)
MS: APCI (−ve) 323 (M−1)

EXAMPLE 55

[[5'-Chloro-2'-methyl-5-(trifluoromethyl)[1,1'-biphenyl]-2-yl]oxy]-acetic acid

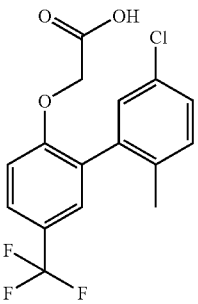

¹H NMR DMSO-d6: δ 7.70 (1H, d), 7.43 (1H, s), 7.38 (1H, s), 7.29 (1H, d), 7.19 (1H, d), 7.14 (1H, s), 4.70 (2H, s), 2.14 (3H, s)
MS: APCI (−ve) 343/345 (M−1)

EXAMPLE 56

[[2'-Fluoro-6'-methyl-5-(trifluoromethyl)[1,1'-biphenyl]-2-yl]oxy]-acetic acid

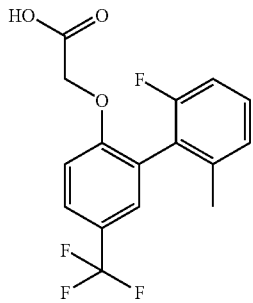

¹H NMR DMSO-d6: δ 7.71 (1H, d), 7.44 (1H, s), 7.27 (1H, q), 7.18 (1H, t), 7.11 (1H, d), 7.04 (1H, d), 4.67 (2H, s), 2.06 (3H, s)
MS: APCI (−ve) 327 (M−1)

EXAMPLE 57

[[4'-Fluoro-2'-methyl-5-(trifluoromethyl)[1,1'-biphenyl]-2-yl]oxy]-acetic acid

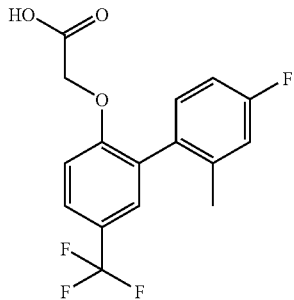

¹H NMR DMSO-d6: δ 7.70 (1H, d), 7.42 (1H, s), 7.30 (1H, t), 7.12 (1H, d), 7.10 (1H, d), 7.04 (1H, d), 4.69 (2H, s), 2.11 (3H, s)
MS: APCI (−ve) 327 (M−1)

EXAMPLE 58

[[4'-[[(Ethylamino)carbonyl]amino]-2'-methyl-5-(trifluoromethyl)[1,1'-biphenyl]-2-yl]oxy]-acetic acid

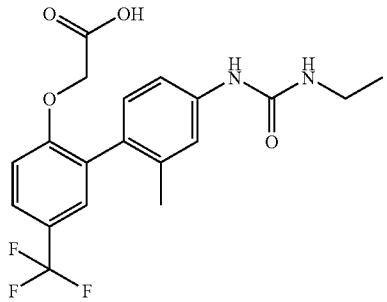

¹H NMR DMSO-d6: δ 8.49 (1H, s), 7.62 (1H, d), 7.31 (1H, s), 7.29 (1H, s), 7.24 (1H, d), 7.04 (1H, d), 7.00 (1H, d), 6.25 (1H, t), 4.60 (2H, s), 3.10 (2H, m), 1.06 (3H, t)
MS: APCI (−ve) 395 (M−1)

EXAMPLE 59

[[2'-Methyl-4'-[[(methylamino)carbonyl]amino]-5-(trifluoromethyl)[1,1'-biphenyl]-2-yl]oxy]-acetic acid

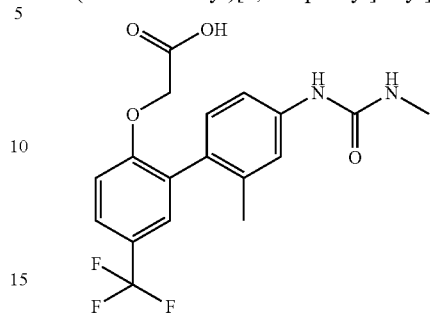

¹H NMR DMSO-d6: δ 8.52 (1H, s), 7.65 (1H, d), 7.39 (1H, s), 7.26 (1H, s), 7.26 (1H, d), 7.07 (1H, d), 7.00 (1H, d), 6.05 (1H, d), 4.72 (2H, s), 2.09 (3H, s)
MS: APCI (+ve) 383 (M+1)

EXAMPLE 60

[[4'-[[(Cyclopropylamino)carbonyl]amino]-2'-methyl-5-(trifluoromethyl)[1,1'-biphenyl]-2-yl]oxy]-acetic acid

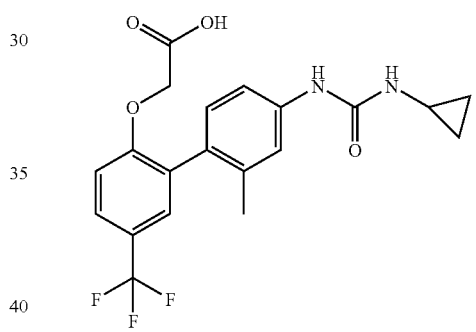

¹H NMR DMSO-d6: δ 8.33 (1H, s), 7.66 (1H, d), 7.37 (1H, s), 7.31 (1H, s), 7.26 (1H, d), 7.08 (1H, d), 7.00 (1H, d), 6.46 (1H, s), 4.75 (2H, s), 2.54 (1H, m), 0.63 (2H, m), 0.42 (2H, m)
MS: APCI (+ve) 409 (M+1)

EXAMPLE 61

[[2'-Methyl-4'-[[(propylamino)carbonyl]amino]-5-(trifluoromethyl)[1,1'-biphenyl]-2-yl]oxy]-acetic acid,

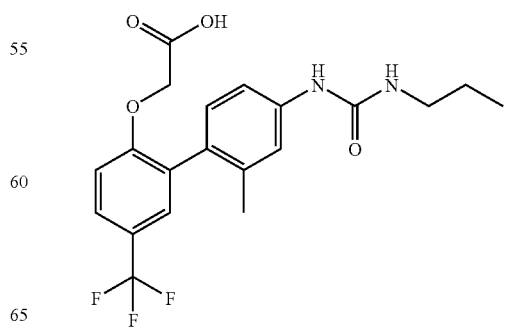

¹H NMR DMSO-d6: δ 8.48 (1H, s), 7.64 (1H, d), 7.36 (1H, s), 7.30 (1H, s), 7.24 (1H, d), 7.07 (1H, d), 7.00 (1H, d), 6.23 (1H, t), 4.68 (2H, s), 3.05 (2H, q), 2.10 (3H, s), 1.44 (2H, m), 0.88 (3H, d)

MS: APCI (+ve) 411 (M+1)

EXAMPLE 62

[[2',4'-Dimethyl-5-(trifluoromethyl)[1,1'-biphenyl]-2-yl]oxy]-acetic acid

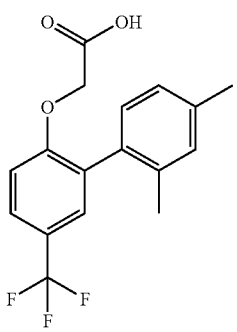

¹H NMR DMSO-d6: δ 7.63 (1H, d), 7.34 (1H, s), 7.03 (4H, m), 4.50 (2H, s), 2.32 (3H, s), 2.11 (3H, s)

MS: APCI (−ve) 323 (M−1)

EXAMPLE 63

[[5'-Fluoro-2'-methyl-5-(trifluoromethyl)[1,1'-biphenyl]-2-yl]oxy]-acetic acid

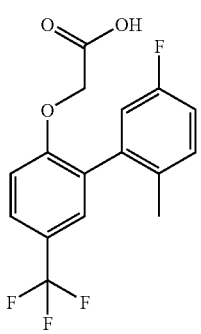

¹H NMR DMSO-d6: δ 7.65 (1H, d), 7.38 (1H, s), 7.29 (1H, d), 7.27 (1H, d), 7.11 (1H, d), 7.06 (1H, m), 4.40 (2H, s), 2.13 (3H, s)

MS: APCI (−ve) 327 (M−1)

EXAMPLE 64

[[4'-(Aminocarbonyl)-2'-methyl-5-(trifluoromethyl)[1,1'-biphenyl]-2-yl]oxy]-acetic acid

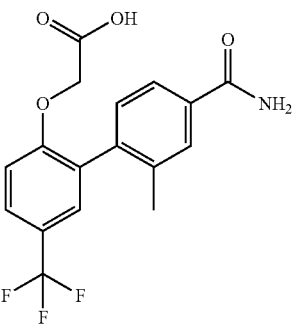

¹H NMR DMSO-d6: δ (1H, s), 7.77 (1H, s), 7.70 (1H, d), 7.63 (1H, d), 7.34 (1H, s), 7.30 (1H, s), 7.25 (1H, d), 6.98 (1H, d), 4.22 (2H, s), 2.21 (3H, s)

MS: APCI (+ve) 354 (M+1)

EXAMPLE 65

[[3'-Fluoro-2'-methyl-5-(trifluoromethyl)[1,1'-biphenyl]-2-yl]oxy]-acetic acid

¹H NMR DMSO-d6: δ 7.66 (1H, d), 7.40 (1H, s), 7.27 (1H, d), 7.24 (1H, d), 7.16 (1H, t), 7.05 (1H, d), 4.45 (2H, s), 2.07 (3H, s)

MS: APCI (1ve) 327 (M−1)

EXAMPLE 66

[[2',5'-Difluoro-5-(trifluoromethyl)[1,1'-biphenyl]-2-yl]oxy]-acetic acid

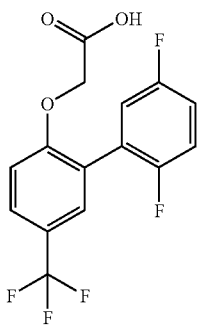

$^1$H NMR DMSO-d6: δ 7.68 (1H, d), 7.58 (1H, s), 7.53 (1H, m), 7.30 (1H, m), 7.28 (1H, m), 7.09 (1H, d), 4.44 (2H, s)

EXAMPLE 67

[[5'-(Aminosulfonyl)-2'-chloro-5-(trifluoromethyl)[1,1'-biphenyl]-2-yl]oxy]acetic acid

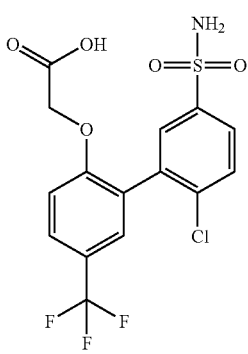

$^1$H NMR DMSO-d6: δ 7.93 (1H, d), 7.82 (1H, d), 7.76 (1H, s), 7.73 (1H, d), 7.53 (1H, s), 7.10 (1H, d), 4.38 (2H, s)
MS: APCI (+ve) 408/410 (M+1)

EXAMPLE 68

[[4'-Cyano-2'-methyl-5-(trifluoromethyl)[1,1'-biphenyl]-2-yl]oxy]-acetic acid

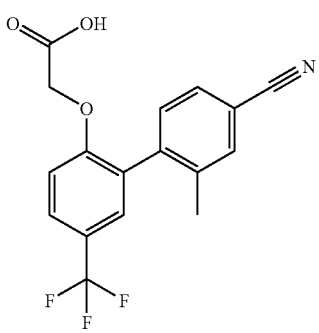

$^1$H NMR DMSO-d6: δ 7.78 (1H, s), 7.71 (1H, t), 7.71 (1H, m), 7.46 (1H, s), 7.40 (1H, d), 7.11 (1H, d), 4.61 (2H, s), 2.18 (3H, s)
MS: APCI (−ve) 334 (M−1)

EXAMPLE 69

[[4'-Chloro-2'-fluoro-5-(trifluoromethyl)[1,1'-biphenyl]-2-yl]oxy]-acetic acid

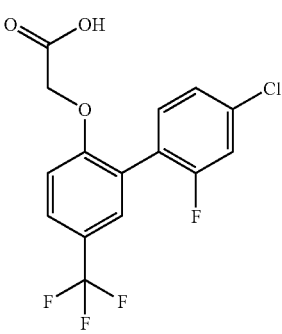

$^1$H NMR DMSO-d6: δ 7.73 (1H, d), 7.60 (1H, s), 7.56 (1H, s), 7.52 (1H, d), 7.36 (1H, d), 7.17 (1H, d), 4.70 (2H, s)

EXAMPLE 70

[[2',5'-Difluoro-4'-methoxy-5-(trifluoromethyl)[1,1'-biphenyl]-2-yl]oxy]-acetic acid

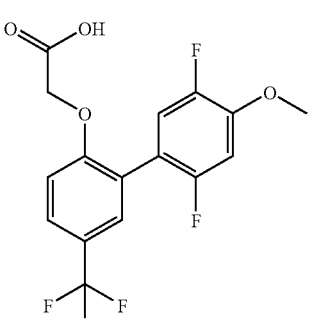

$^1$H NMR DMSO-d6: δ 7.63 (1H, d), 7.60 (1H, m), 7.52 (1H, s), 7.19 (1H, m), 7.06 (1H, d), 4.39 (2H, s), 3.91 (3H, s)

EXAMPLE 71

[[2'-fluoro-5'-methyl-5-(trifluoromethyl)[1,1'-biphenyl]-2-yl]oxy]-acetic acid

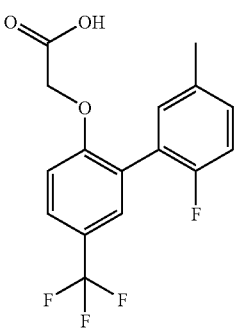

¹H NMR DMSO-d6: δ 7.74 (1H, d), 7.57 (1H, s), 7.25 (1H, d), 7.26 (1H, s), 7.19 (1H, d), 7.14 (1H, d), 4.85 (2H, s), 2.35 (3H, s)

EXAMPLE 72

[[2'-Fluoro-4'-methyl-5-(trifluoromethyl)[1,1'-biphenyl]-2-yl]oxy]-acetic acid

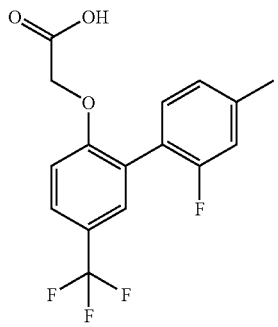

¹H NMR DMSO-d6: δ 7.67 (1H, d), 7.46 (1H, s), 7.40 (1H, t), 7.10 (1H, d), 7.07 (1H, d), 7.07 (1H, s), 4.49 (2H, s), 2.34 (3H, s)

EXAMPLE 73

[[4'-Methoxy-2 methyl-5-(trifluoromethyl)[1,1'-biphenyl]-2-yl]oxy]-acetic acid

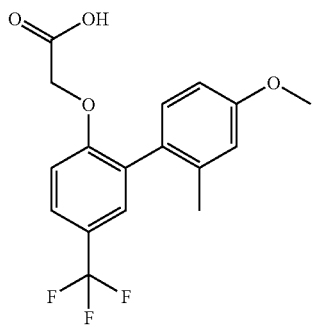

¹H NMR DMSO-d6: δ 7.62 (1H, d), 7.33 (1H, s), 7.08 (1H, d), 7.00 (1H, d), 6.82 (1H, s), is 6.78 (1H, d), 4.45 (2H, s), 3.80 (3H, s), 2.13 (3H, s)

EXAMPLE 74

[[4'-(Aminosulfonyl)-2',5'-difluoro-5-(trifluoromethyl)[1,1'-biphenyl]-2-yl]oxy]-acetic acid

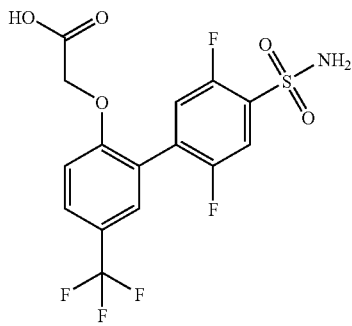

¹H NMR DMSO-d6: δ 7.83 (1H, m), 7.75 (1H, d), 7.69 (1H, s), 7.63 (1H, m), 7.18 (1H, d), 4.53 (2H, s)

MS: APCI (−ve) 410 (M−1)

EXAMPLE 75

[2-Benzo[b]thien-3-yl-4-(trifluoromethyl)phenoxy]-acetic acid

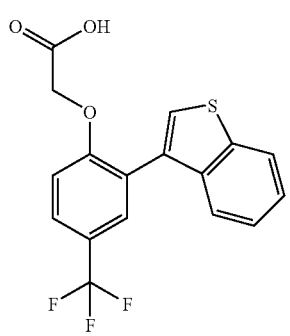

¹H NMR DMSO-d6: δ 8.04 (1H, d), 7.87 (1H, s), 7.78 (1H, d), 7.69 (1H, d), 7.67 (1H, s), 7.38 (2H, m), 7.24 (1H, d), 4.81 (2H, s)

MS: APCI (−ve) 351 (M−1)

EXAMPLE 76

[[5-(Trifluoromethyl)[1,1'-biphenyl]-2-yl]oxy]-acetic acid

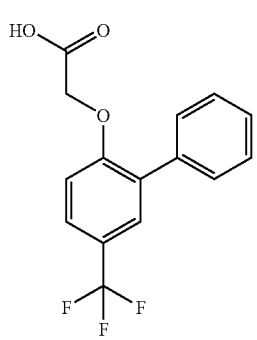

¹H NMR DMSO-d6: δ 7.69 (1H, d), 7.60 (3H, m), 7.41 (3H, m), 7.20 (1H, d), 4.88 (2H, s)

MS: APCI (−ve) 295 (M−1)

EXAMPLE 77

[2-(2-Benzofuranyl)-4-(trifluoromethyl)phenoxy]-acetic acid

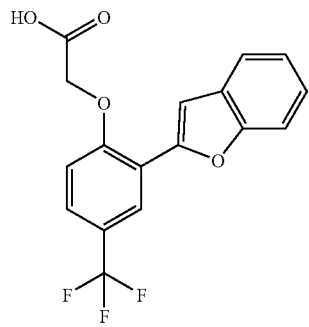

$^1$H NMR DMSO-d6: δ 8.24 (1H, s), 7.85 (1H, s), 7.75 (1H, d), 7.70 (2H, d), 7.33 (3H, m), 5.07 (2H, s)

MS: APCI (−ve) 335 (M−1)

EXAMPLE 78

[[4'-Chloro-5-(trifluoromethyl)[1,1'-biphenyl]-2-yl]oxy]-acetic acid

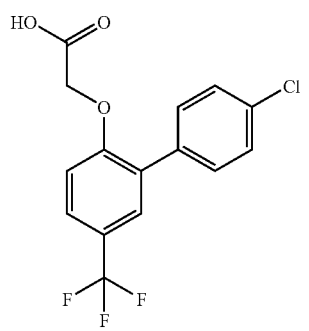

$^1$H NMR DMSO-d6: δ 7.70 (1H, d), 7.64 (1H, d), 7.62 (1H, s), 7.62 (1H, d), 7.50 (1H, d), 7.50 (1H, d), 7.21 (1H, d), 4.81 (2H, s)

MS: APCI (−ve) 329/331 (M−1)

EXAMPLE 79

[[3'-(1-Methylethyl)-5-(trifluoromethyl)[1,1'-biphenyl]-2-yl]oxy]-acetic acid

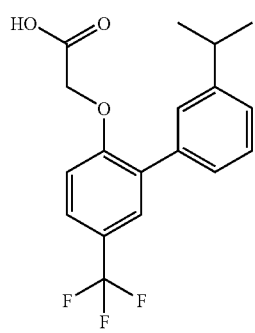

$^1$H NMR DMSO-d6: δ 7.67 (1H, d), 7.57 (1H, s), 7.48 (1H, s), 7.38 (1H, t), 7.36 (1H, d), 7.25 (1H, d), 7.20 (1H, d), 4.85 (2H, s)

MS: APCI (−ve) 337 (M−1)

EXAMPLE 80

[[3',4'-Difluoro-5-(trifluoromethyl)[1,1'-biphenyl]-2-yl]oxy]-acetic acid

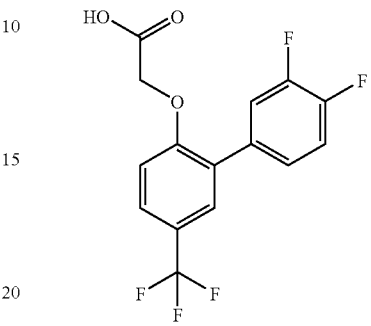

$^1$H NMR DMSO-d6: δ 7.76 (1H, d), 7.71 (1H, d), 7.65 (1H, s), 7.51 (1H, d), 7.48 (1H, s), 7.25 (1H, d), 4.89 (2H, s)

MS: APCI (−ve) 331 (M−1)

EXAMPLE 81

[2-(1,3-Benzodioxol-5-yl)-4-(trifluoromethyl)phenoxy]-acetic acid

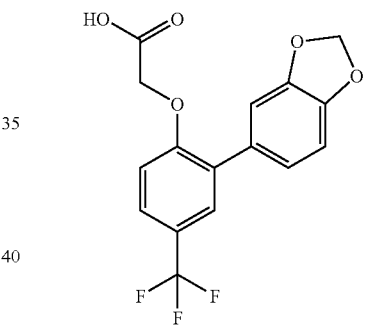

$^1$H NMR DMSO-d6: δ 7.63 (1H, d), 7.57 (1H, s), 7.22 (1H, s), 7.16 (1H, d), 7.05 (1H, d), 6.98 (1H, d), 6.04 (2H, s), 4.83 (2H, s)

MS: APCI (−ve) 339 (M−1)

EXAMPLE 82

[[4'-Ethyl-5-(trifluoromethyl)[1,1'-biphenyl]-2-yl]oxy]-acetic acid

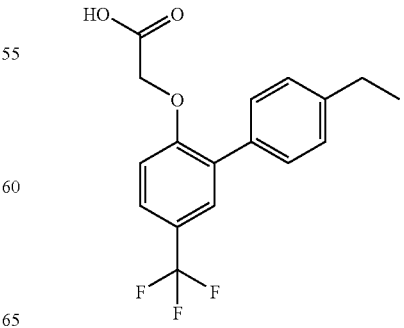

¹H NMR DMSO-d6: δ 7.66 (1H, d), 7.58 (1H, s), 7.51 (2H, d), 7.27 (2H, d), 7.18 (1H, d), 4.86 (2H, s), 2.65 (2H, q), 1.22 (3H, t)
MS: APCI (−ve) 323 (M−1)

EXAMPLE 83

[[3'-Fluoro-5-(trifluoromethyl)[1,1':4',1''-terphenyl]-2-yl]oxy]-acetic acid

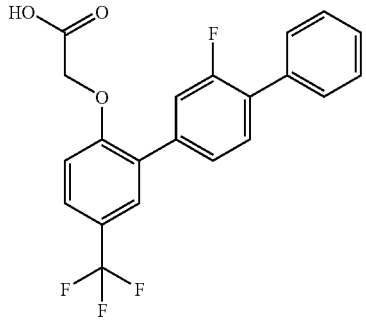

¹H NMR DMSO-d6: δ 7.74 (1H, d), 7.65 (2H, m), 7.60 (1H, m), 7.59 (2H, m), 7.58 (1H, m), 7.52 (2H, m), 7.43 (1H, m), 7.12 (1H, m), 4.51 (2H, s)
MS: APCI (−ve) 389 (M−1)

EXAMPLE 84

[[4'-(Trifluoromethoxy)-5-(trifluoromethyl)[1,1'-biphenyl]-2-yl]oxy]-acetic acid

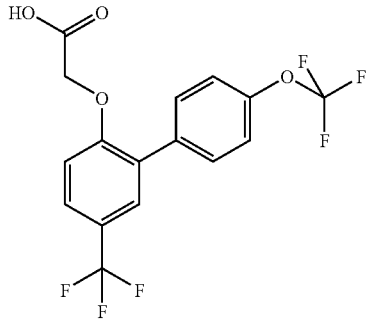

¹H NMR DMSO-d6: δ 7.82 (2H, d), 7.62 (1H, d), 7.58 (1H, s), 7.41 (2H, d), 7.05 (1H, d), 4.39 (2H, s)
MS: APCI (−ve) 379 (M−1)

EXAMPLE 85

[[2',3'-Dichloro-5-(trifluoromethyl)[1,1'-biphenyl]-2-yl]oxy]-acetic acid

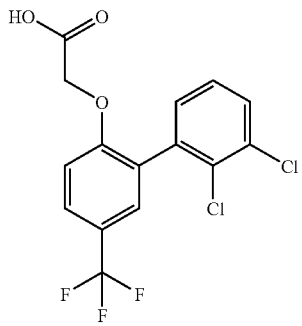

¹H NMR DMSO-d6: δ 7.68 (1H, d), 7.66 (1H, d), 7.47 (1H, d), 7.48 (1H, s), 7.41 (1H, t), 7.05 (1H, d), 4.26 (2H, d)
MS: APCI (−ve) 363 (M−1)

EXAMPLE 86

[[4'-(1,1-Dimethylethyl)-5-(trifluoromethyl)[1,1'-biphenyl]-2-yl]oxy]-acetic acid

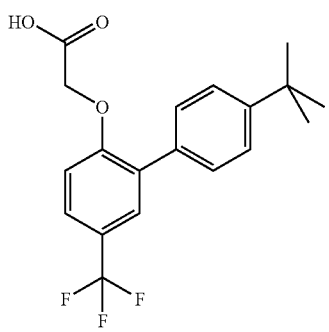

¹H NMR DMSO-d6: δ 7.59 (1H, d), 7.57 (2H, d), 7.51 (1H, s), 7.44 (2H, d), 7.04 (1H, d), 4.47 (2H, s)
MS: APCI (−ve) 351 (M−1)

EXAMPLE 87

[2-(6-Methoxy-2-naphthalenyl)-4-(trifluoromethyl)phenoxy]-acetic acid

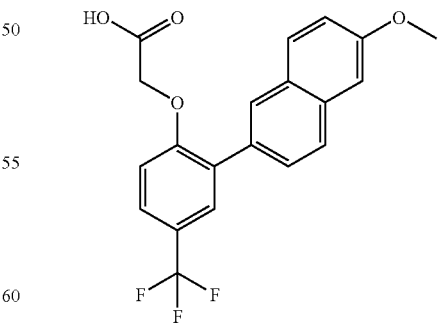

¹H NMR DMSO-d6: δ 8.07 (1H, s), 7.87 (1H, d), 7.85 (2H, s), 7.62 (2H, d), 7.34 (1H, s), 7.17 (1H, d), 7.08 (1H, d), 4.41 (2H, s)
MS: APCI (−ve) 375 (M−1)

EXAMPLE 88

[[4'-(Ethylthio)-5-(trifluoromethyl)[1,1'-biphenyl]-2-yl]oxy]-acetic acid

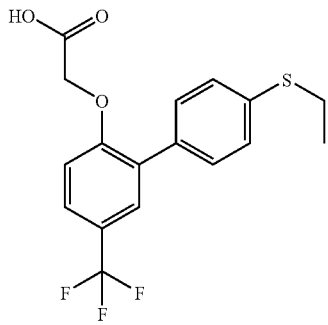

¹H NMR DMSO-d6: δ 7.61 (2H, d), 7.59 (1H, d), 7.52 (1H, s), 7.35 (2H, d), 7.07 (1H, d), 4.50 (2H, s), 3.02 (2H, q), 1.27 (3H, t)

MS: APCI (−ve) 355 (M−1)

EXAMPLE 89

[[4'-Acetyl-5-(trifluoromethyl)[1,1'-biphenyl]-2-yl]oxy]-acetic acid

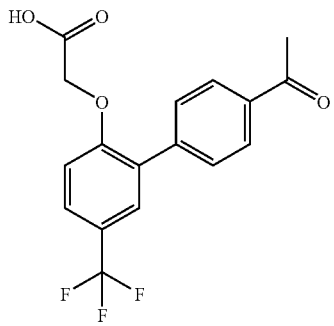

¹H NMR DMSO-d6: δ 8.02 (2H, d), 7.77 (2H, d), 7.64 (1H, s), 7.72 (1H, d), 7.23 (1H, d), 4.83 (2H, s), 2.63 (3H, s)

MS: APCI (−ve) 337 (M−1)

EXAMPLE 90

[2-(2-Chloro-5-methyl-4-pyridinyl)-4-(trifluoromethyl)phenoxy]-acetic acid, ammonium salt

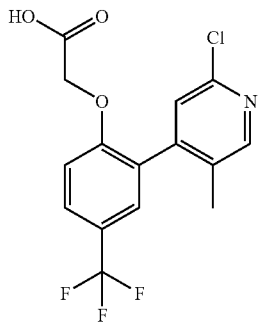

¹H NMR DMSO-d6: δ 8.30 (1H, d), 7.75-7.66 (1H, m), 7.49 (1H, d), 7.04 (2H, d), 4.28 (2H, s), 2.15 (3H, s)

MS: APCI (−ve) 449 (M−1)

EXAMPLE 91

[[5'-(Aminosulfonyl)-2'-methyl-5-(trifluoromethyl)[1,1'-biphenyl]-2-yl]oxy]-acetic acid, ammonium salt

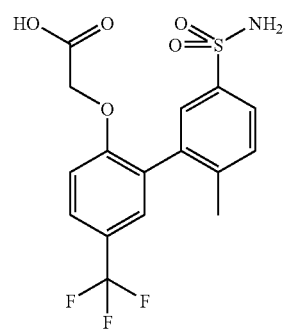

¹H NMR DMSO-d6: δ 7.73-7.65 (3H, m), 7.63 (1H, d), 7.44 (1H, d), 7.37 (1H, d), 7.01 (1H, d), 4.23 (2H, s), 2.24 (3H, s)

MS: APCI (−ve) 388 (M−1)

EXAMPLE 92

[2-(8-Quinolinyl)-4-(trifluoromethyl)phenoxy]-acetic acid, ammonium salt

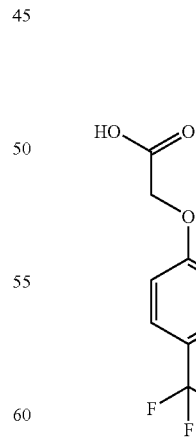

¹H NMR CDCl₃: δ 8.85-8.82 (1H, m), 8.33-8.29 (1H, m), 7.95-7.91 (1H, m), 7.82-7.78 (1H, m), 7.68-7.58 (3H, m), 7.50-7.46 (1H, m), 7.14-7.10 (1H, m), 4.54 (2H, s)

MS: APCI (−ve) 346 (M−1)

EXAMPLE 93

[[3'-Cyano-5-(trifluoromethyl)[1,1'-biphenyl]-2-yl]oxy]-acetic acid, ammonium salt

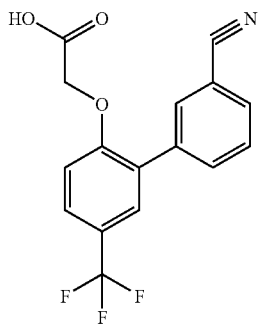

$^1$H NMR CDCl$_3$: δ 8.00 (1H, d), 7.87-7.83 (1H, m), 7.66-7.52 (4H, m), 6.99 (1H, d), 4.68 (2H, s)
MS: APCI (−ve) 320 (M−1)

EXAMPLE 94

[2-[4-Methyl-6-[methyl(methylsulfonyl)amino]-3-pyridinyl]-4-(trifluoromethyl)phenoxy]-acetic acid, ammonium salt

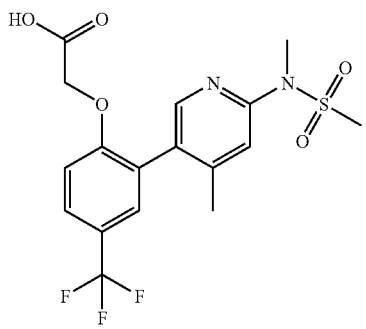

$^1$H NMR DMSO-d6: δ 8.20 (1H, s), 7.71 (1H, m), 7.51-7.47 (1H, m), 7.33 (1H, s), 7.09 (1H, d), 4.52 (2H, s), 3.32 (3H, s), 3.18 (3H, d), 2.21 (3H, s)
MS: APCI (−ve) 419 (M−1)

EXAMPLE 95

[[2'-Methyl-5'-(methylsulfonyl)-5-(trifluoromethyl)[1,1'-biphenyl]-2-yl]oxy]-acetic acid, ammonium salt

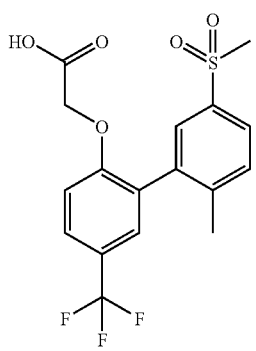

$^1$H NMR DMSO-d6: δ 7.83-7.80 (1H, m), 7.74-7.69 (2H, m), 7.55 (1H, d), 7.49 (1H, d), 7.09 (1H, d), 4.46 (2H, s), 3.23 (3H, s), 2.26 (3H, s)
MS: APCI (+ve) 406 (M+1)

EXAMPLE 96

2'-(Carboxymethoxy)-5'-(trifluoromethyl)-[1,1'-biphenyl]-3-carboxylic acid, 3-methyl ester

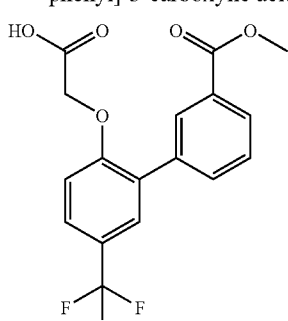

$^1$H NMR DMSO-d6: δ 8.15-8.13 (1H, m), 7.99-7.93 (2H, m), 7.68-7.55 (3H, m), 7.10 (1H, d), 4.46 (2H, s), 3.87 (3H, s)
MS: APCI (−ve) 353 (M−1)

EXAMPLE 97

2'-(Carboxymethoxy)-5'-(trifluoromethyl)-[1,1'-biphenyl]-2-carboxylic acid, 2-methyl ester

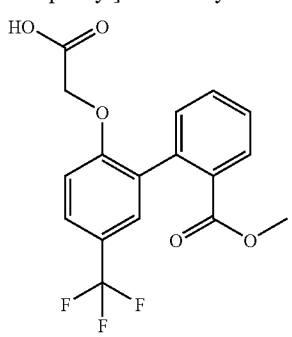

$^1$H NMR DMSO-d6: δ 7.77 (1H, M), 7.66-7.59 (2H, m), 7.51-7.42 (3H, m), 4.23 (2H, s), 3.59 (4H, s)
MS: APCI (−ve) 353 (M−1)

EXAMPLE 98

[[5-(Trifluoromethyl)[1,1':4',1''-terphenyl]-2-yl]oxy]-acetic acid

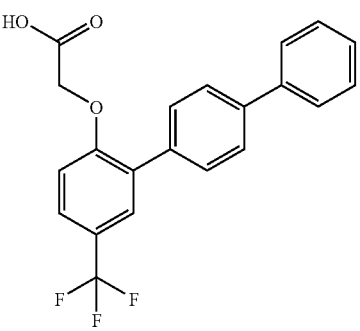

$^1$H NMR DMSO-d6: δ 7.75-7.62 (7H, m), 7.53-7.46 (3H, m), 7.42-7.35 (1H, m), 7.21-7.15 (1H, m), 4.76 (2H, s)
MS: APCI (−ve) 371 (M−1)

EXAMPLE 99

[[3'-Fluoro-2',4'-dimethyl-5-(trifluoromethyl)[1,1'-biphenyl]-2-yl]oxy]-acetic acid

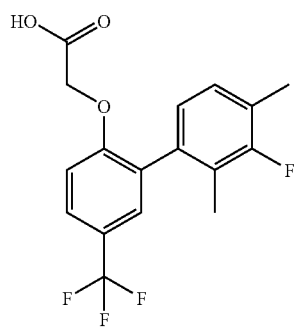

¹H NMR DMSO-d6: δ 7.66-7.62 (1H, m), 7.55 (1H, d), 7.34 (2H, d), 7.16 (1H, d), 4.78 (2H, s), 2.25 (6H, d)
MS: APCI (−ve) 341 (M−1)

EXAMPLE 100

[[2'-Nitro-5-(trifluoromethyl)[1,1'-biphenyl]-2-yl]oxy]-acetic acid, ammonium salt

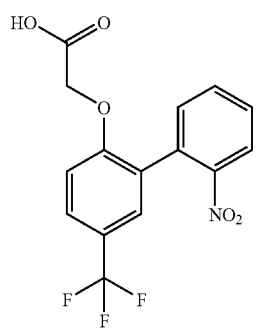

¹H NMR DMSO-d6: δ 8.00 (1H, m), 7.83-7.76 (1H, m), 7.70-7.55 (4H, m), 6.94 (1H, d), 4.08 (2H, s)
MS: APCI (−ve) 340 (M−1)

EXAMPLE 101

[[2'-Methyl-5-(trifluoromethyl)[1,1'-biphenyl]-2-yl]oxy]-acetic acid

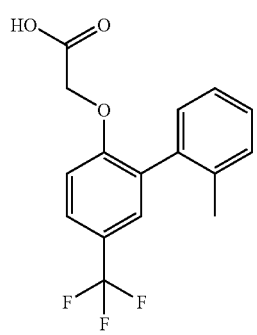

¹H NMR DMSO-d6: δ 7.65-7.61 (1H, m), 7.34-7.32 (1H, m), 7.28-7.14 (4H, m), 7.02-6.98 (1H, m), 4.36 (2H, s), 2.13 (3H, s)
MS: APCI (−ve) 340 (M−1)

EXAMPLE 102

[[3'-Chloro-2'-methyl-5-(trifluoromethyl)[1,1'-biphenyl]-2-yl]oxy]-acetic acid

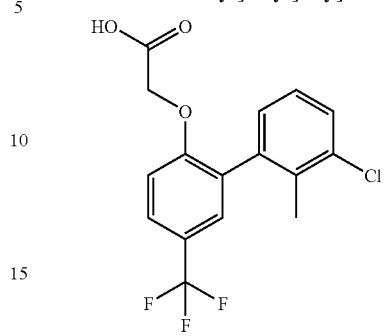

¹H NMR DMSO-d6: δ 7.72-7.66 (1H, m), 7.47-7.40 (2H, m), 7.30-7.22 (1H, m), 7.18-7.14 (1H, m), 7.10-7.06 (1H, m), 4.56 (2H, s), 2.14 (3H, s)
MS: APCI (−ve) 343 (M−1)

EXAMPLE 103

[[5-(Trifluoromethyl)[1,1':3',1''-terphenyl]-2-yl]oxy]-acetic acid

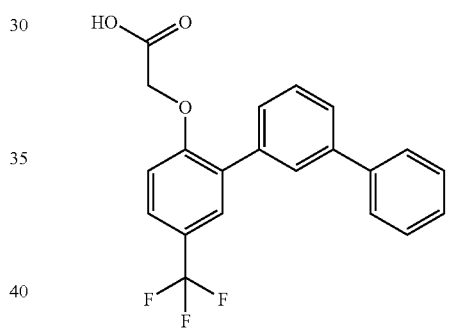

¹H NMR DMSO-d6: δ 7.92 (1H, t), 7.76-7.72 (2H, m), 7.68-7.59 (4H, m), 7.56-7.34 (4H, m), 7.19-7.15 (1H, m), 4.69 (2H, s)
MS: APCI (−ve) 371 (M−1)

EXAMPLE 104

2'-(Carboxymethoxy)-5'-(trifluoromethyl)-[1,1'-biphenyl]-4-carboxylic acid, 4-methyl ester

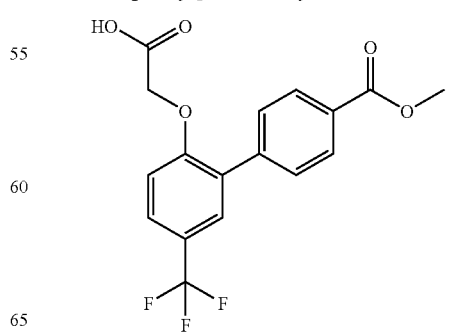

¹H NMR DMSO-d6: δ 8.03-7.99 (2H, m), 7.82-7.79 (2H, m), 7.70-7.66 (1H, m), 7.63-7.61 (1H, m), 7.17-7.14 (1H, m), 4.62 (2H, s), 3.88 (3H, s)
MS: APCI (−ve) 353 (M−1)

EXAMPLE 105

[[4'-Nitro-5-(trifluoromethyl)[1,1'-biphenyl]-2-yl]oxy]-acetic acid

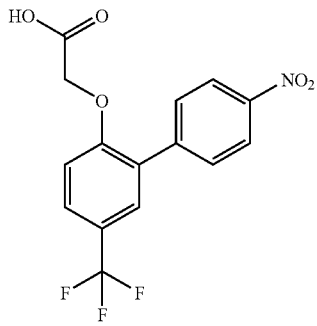

¹H NMR DMSO-d6: δ 8.30-8.26 (2H, m), 7.99-7.94 (2H, m), 7.75-7.67 (2H, m), 7.20 (1H, d), 4.65 (2H, s)
MS: APCI (−ve) 340 (M−1)

EXAMPLE 106

[[5-(Trifluoromethyl)-3'-[(trifluoromethyl)thio][1,1'-biphenyl]-2-yl]oxy]-acetic acid

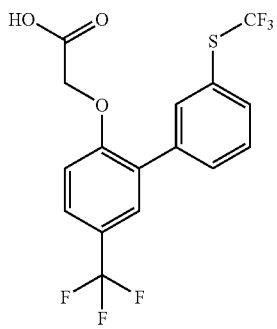

¹H NMR DMSO-d6: δ 8.05 (1H, s), 7.91-7.87 (1H, m), 7.74-7.58 (4H, m), 7.17 (1H, d), 4.64 (2H, s)
MS: APCI (−ve) 395 (M−1)

EXAMPLE 107

[[5-(Trifluoromethyl)-4'-[(trifluoromethyl)thio][1,1'-biphenyl]-2-yl]oxy]-acetic acid

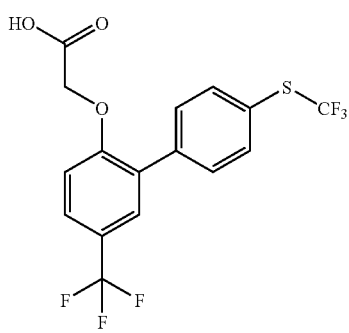

¹H NMR DMSO-d6: δ 7.79 (4H, s), 7.76-7.72 (1H, m), 7.69-7.67 (1H, m), 7.25 (1H, d), 4.89 (2H, s)
MS: APCI (−ve) 395 (M−1)

EXAMPLE 108

[[4'-Methyl-5-(trifluoromethyl)[1,1'-biphenyl]-2-yl]oxy]-acetic acid

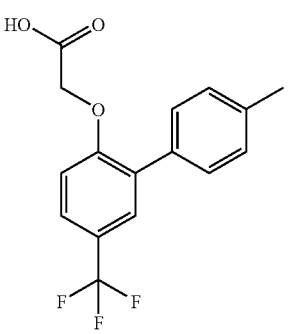

¹H NMR DMSO-d6: δ 7.67-7.63 (1H, m), 7.57-7.54 (1H, m), 7.51-7.47 (2H, m), 7.25 (2H, d), 7.17 (1H, d), 4.82 (2H, s), 2.35 (3H, s)
MS: APCI (−ve) 309 (M−1)

EXAMPLE 109

[[4'-Fluoro-5-(trifluoromethyl)[1,1'-biphenyl]-2-yl]oxy]-acetic acid

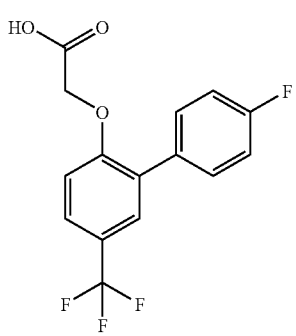

¹H NMR DMSO-d6: δ 7.71-7.58 (4H, m), 7.31-7.18 (3H, m), 4.86 (2H, s)
MS: APCI (−ve) 314 (M−1)

EXAMPLE 110

[[3'-Fluoro-5-(trifluoromethyl)[1,1'-biphenyl]-2-yl]oxy]-acetic acid

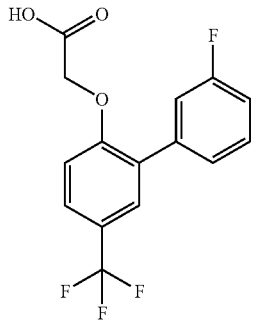

$^1$H NMR DMSO-d6: δ 7.74-7.69 (1H, m), 7.66-7.64 (1H, m), 7.53-7.42 (3H, m), 7.26-7.18 (2H, m), 4.88 (2H, s)
MS: APCI (−ve) 314 (M−1)

EXAMPLE 111

[[3'-Methyl-5-(trifluoromethyl)[1,1'-biphenyl]-2-yl]oxy]-acetic acid

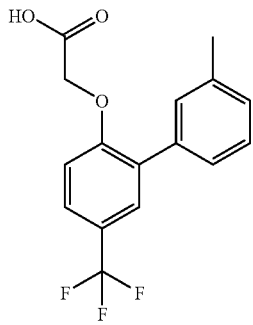

$^1$H NMR DMSO-d6: δ 7.70-7.63 (1H, m), 7.56 (1H, d), 7.42-7.28 (3H, m), 7.21-7.15 (2H, m), 4.82 (2H, s), 2.34 (3H, s)
MS: APCI (−ve) 309 (M−1)

EXAMPLE 112

[2-(3-Pyridinyl)-4-(trifluoromethyl)phenoxy]-acetic acid

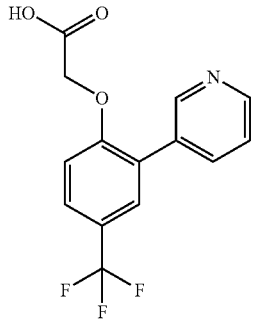

$^1$H NMR DMSO-d6: δ 8.88 (1H, s), 8.56-8.53 (1H, m), 8.15-8.09 (1H, m), 7.68-7.60 (2H, m), 7.48-7.42 (1H, m), 7.10 (1H, d), 4.43 (2H, s)
MS: APCI (+ve) 298 (M+1)

EXAMPLE 113

[[2'-Fluoro-5-(trifluoromethyl)[1,1'-biphenyl]-2-yl]oxy]-acetic acid

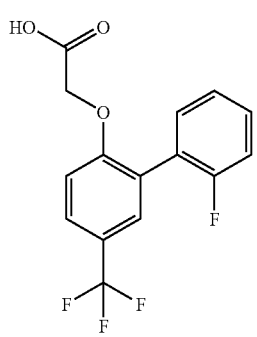

$^1$H NMR DMSO-d6: δ 8.02 (1H, d), 7.92-7.90 (1H, m), 7.79-7.54 (4H, m), 7.28 (1H, d), 4.90 (2H, s)
MS: APCI (−ve) 313 (M−1)

EXAMPLE 114

[[2'-Methoxy-5-(trifluoromethyl)[1,1'-biphenyl]-2-yl]oxy]-acetic acid

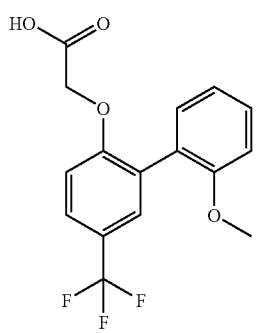

$^1$H NMR DMSO-d6: δ 7.59 (1H, d), 7.42 (1H, s), 7.37-7.30 (2H, m), 7.11-6.95 (3H, m), 4.42 (2H, s), 3.72 (3H, s)
MS: APCI (−ve) 325 (M−1)

EXAMPLE 115

[[3'-Methoxy-5-(trifluoromethyl)[1,1'-biphenyl]-2-yl]oxy]-acetic acid

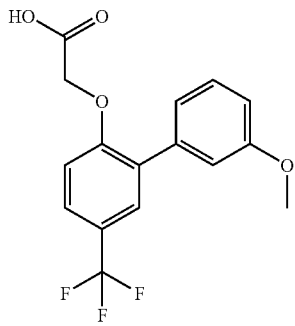

¹H NMR DMSO-d6: δ 7.62 (1H, d), 7.56-7.54 (1H, m), 7.34 (1H, t), 7.27-7.25 (1H, m), 7.16 (1H, d), 7.11 (1H, d), 6.95-6.90 (1H, m), 4.56 (2H, s), 3.79 (3H, s)
MS: APCI (−ve) 325 (M−1)

EXAMPLE 116

[[4'-Methoxy-5-(trifluoromethyl)[1,1'-biphenyl]-2-yl]oxy]-acetic acid

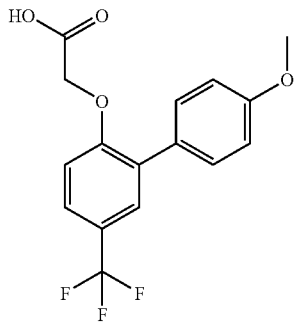

¹H NMR DMSO-d6: δ 7.62-7.54 (4H, m), 7.04 (1H, d), 6.98 (2H, d), 4.45 (2H, s), 3.79 (3H, s)
MS: APCI (−ve) 325 (M−1)

EXAMPLE 117

[[3'-(Ethylsulfonyl)-5-(trifluoromethyl)[1,1'-biphenyl]-2-yl]oxy]-acetic acid

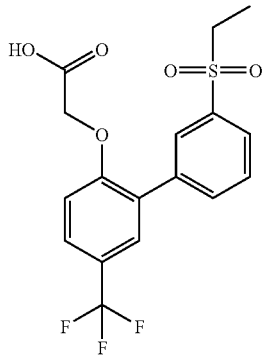

¹H NMR DMSO-d6: δ 8.19-8.17 (1H, m), 8.11-8.07 (1H, m), 7.87-7.83 (1H, m), 7.73-7.64 (3H, m), 7.11 (1H, d), 4.39 (2H, s), 3.38 (2H, q), 1.14 (3H, t)
MS: APCI (−ve) 387 (M−1)

EXAMPLE 118

[[3'-Propoxy-5-(trifluoromethyl)[1,1'-biphenyl]-2-yl]oxy]-acetic acid

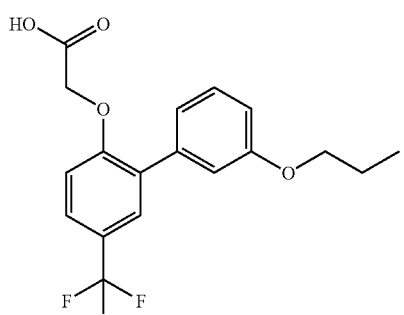

¹H NMR DMSO-d6: δ 7.70-7.65 (1H, m), 7.59 (1H, d), 7.33 (1H, t), 7.22-7.10 (3H, m), 6.95-6.91 (1H, m), 4.86 (2H, s), 3.97 (2H, t), 1.79-1.68 (2H, m), 0.98 (3H, t)
MS: APCI (−ve) 353 (M−1)

EXAMPLE 119

[[4'-Propoxy-5-(trifluoromethyl)[1,1'-biphenyl]-2-yl]oxy]-acetic acid

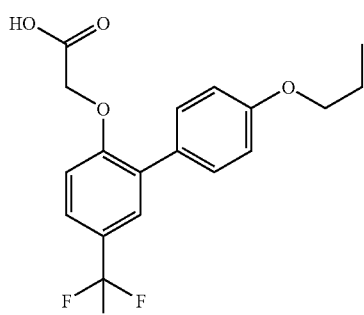

¹H NMR DMSO-d6: δ 7.65-7.61 (1H, m), 7.56-7.50 (3H, m), 7.16 (1H, d), 7.01-6.96 (2H, m), 4.85 (2H, s), 3.97 (2H, t), 1.80-1.70 (2H, m), 0.99 (3H, t)
MS: APCI (−ve) 353 (M−1)

EXAMPLE 120

[2-(2-Amino-4-methyl-5-pyrimidinyl)-4-(trifluoromethyl)phenoxy]-acetic acid

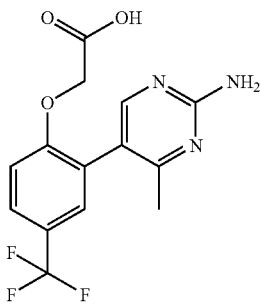

$^1$H NMR DMSO-d6: δ 7.99 (s, 1H), 7.62 (dd, 1H), 7.43 (d, 1H), 7.01 (d, 1H), 6.56 (s, 2H), 4.41 (s, 2H), 2.15 (s, 3H).

MS: APCI (+ve) 328

EXAMPLE 121

[[4'-Cyano-5-(trifluoromethyl)[1,1'-biphenyl]-2-yl]oxy]-acetic acid

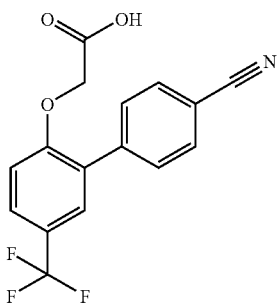

$^1$H NMR CD$_3$OD: δ 7.86-7.73 (m, 4H), 7.65 (dd, 1H), 7.60 (d, 1H), 7.14 (d, 1H), 4.66 (s, 2H)

MS: APCI (+ve) 320

EXAMPLE 122

[[4',5-Bis(trifluoromethyl)[1,1'-biphenyl]-2-yl]oxy]-acetic acid

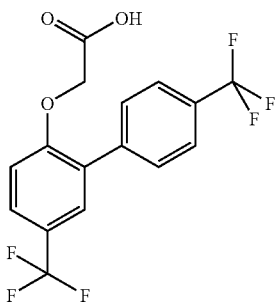

$^1$H NMR DMSO-d6: δ 7.90 (2H, d), 7.78 (2H, d), 7.67 (1H, d), 7.62 (1H, s), 7.10 (1H, d), 4.47 (2H, s)

MS: APCI (−ve) 363 (M−1)

EXAMPLE 123

[2-(2-Naphthalenyl)-4-(trifluoromethyl)phenoxy]-acetic acid

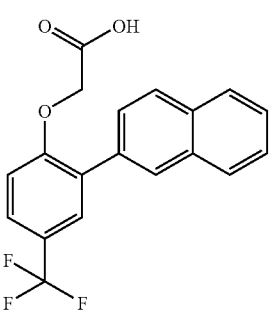

$^1$H NMR DMSO-d6: δ 8.15 (1H, s), 7.93 (4H, m), 7.67 (1H, s), 7.64 (1H, d), 7.53 (2H, m), 7.09 (1H, d), 4.44 (2H, s)

MS: APCI (−ve) 345 (M−1)

EXAMPLE 124

[[4'-(1-Pyrrolidinylsulfonyl)-5-(trifluoromethyl)[1,1'-biphenyl]-2-yl]oxy]-acetic acid

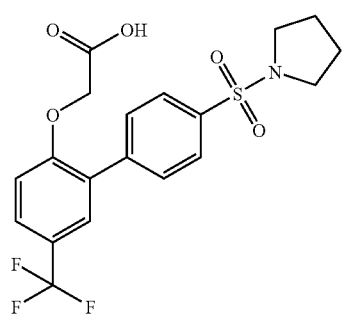

(i) 1-[(4-Bromophenyl)sulfonyl]-pyrrolidine

A solution of 4-bromobenzenesulphonyl chloride (0.5 g) and pyrrolidine (0.284 g) in acetonitrile (5 ml) were stirred at RT for 48 h then partitioned between ethylacetate and water. The organics were separated, washed with water, dried and evaporated under reduced pressure. The residue was triturated with isohexane and filtered, yield 0.5 g.

$^1$H NMR CDCl$_3$: δ 7.72-7.65 (4H, m); 3.28-3.21 (4H, m); 1.84-1.76 (4H, m)

(ii) [[4'-(1-Pyrrolidinylsulfonyl)-5-(trifluoromethyl)[1,1'-biphenyl]-2-yl]oxy]-acetic acid The title compound was prepared by the method of example 44, yield 0.13 g.

$^1$H NMR CD$_3$OD: δ 7.83-7.75 (m, 4H), 7.56-7.52 (m, 1H), 7.50 (d, 1H), 7.01 (d, 1H), 4.46 (s, 2H), 3.20-3.14 (m, 4H), 1.72-1.65 (m, 4H).

MS: APCI (−ve) 428.

EXAMPLE 125-134

The following compounds were synthesised in an analogous method to example 124

EXAMPLE 125

[[4'-[(Dimethylamino)sulfonyl]-5-(trifluoromethyl)[1,1'-biphenyl]-2-yl]oxy]-acetic acid

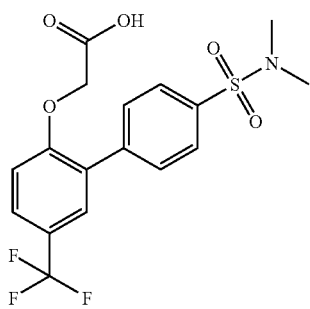

$^1$H NMR CD$_3$OD: δ 7.92-7.81 (m, 4H), 7.67-7.61 (m, 2H), 7.14 (d, 1H), 4.64 (s, 2H), 2.73 (s, 6H).

MS: APCI (+ve) 402

EXAMPLE 126

[[4'-[[(Phenylmethyl)amino]sulfonyl]-5-(trifluoromethyl)[1,1'-biphenyl]-2-yl]oxy]-acetic acid

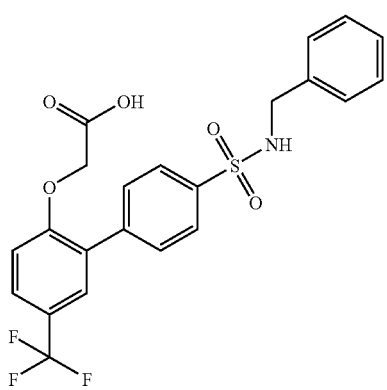

$^1$H NMR CD$_3$OD: δ 7.92-7.77 (m, 4H), 7.68 (d, 1H), 7.62 (s, 1H), 7.29-7.14 (m, 6H), 4.73 (s, 2H), 4.13 (s, 2H).

MS: APCI (−ve) 464.

EXAMPLE 127

[[4'-[[(2,2,2-Trifluoroethyl)amino]sulfonyl]-5-(trifluoromethyl)[1,1'-biphenyl]-2-yl]oxy]-acetic acid

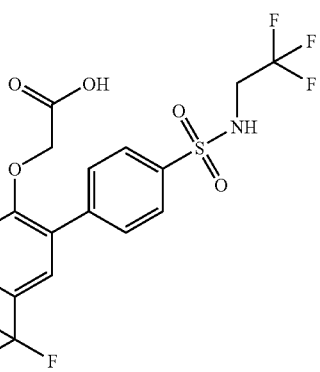

$^1$H NMR CD$_3$OD: δ 7.93-7.79 (m, 4H), 7.64 (d, 1H), 7.59 (d, 1H), 7.12 (d, 1H), 4.64 (s, 2H), 3.63 (t, 2H).

MS: APCI (−ve) 456

EXAMPLE 128

[[4'-[[(5-Methyl-2-thiazolyl)amino]sulfonyl]-5-(trifluoromethyl)[1,1'-biphenyl]-2-yl]oxy]-acetic acid

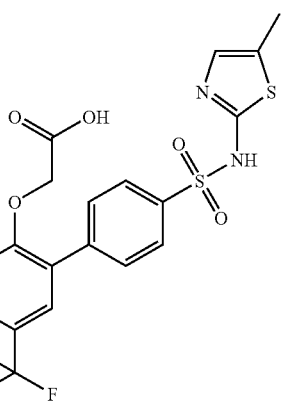

$^1$H NMR CD$_3$OD: δ 7.97-7.92 (m, 2H), 7.82-7.78 (m, 2H), 7.67-7.61 (m, 1H), 7.61-7.58 (m, 1H), 7.12 (d, 2H), 6.82 (d, 1H), 4.61 (s, 2H), 2.27 (d, 3H).

MS: APCI (−ve) 471

EXAMPLE 129

[[4'-[(Phenylamino)sulfonyl]-5-(trifluoromethyl)[1,1'-biphenyl]-2-yl]oxy]-acetic acid

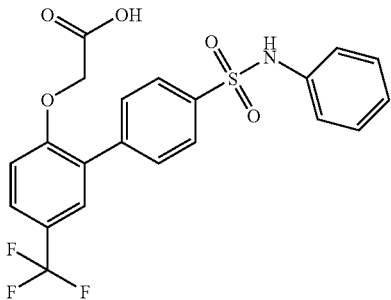

$^1$H NMR CD$_3$OD: δ 7.81-7.73 (m, 4H), 7.60 (dd, 1H), 7.54 (d, 1H), 7.25-7.02 (m, 6H), 4.55 (s, 2H).
MS: APCI (−ve) 450.

EXAMPLE 130

[[4'-[(Diethylamino)sulfonyl]-5-(trifluoromethyl)[1,1'-biphenyl]-2-yl]oxy]-acetic acid

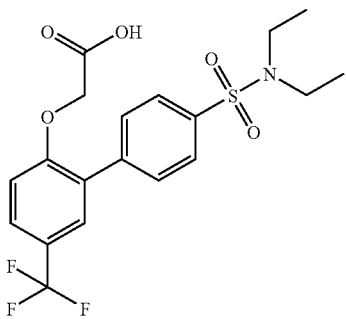

$^1$H NMR CD$_3$OD: δ 7.85 (s, 4H), 7.63 (dd, 1H), 7.59 (d, 1H), 7.11 (d, 1H), 4.58 (s, 2H), 3.27 (q, 4H), 1.16 (t, 6H).
MS: APCI (−ve) 450.

EXAMPLE 131

[[4'-[(Cyclopropylamino)sulfonyl]-5-(trifluoromethyl)[1,1'-biphenyl]-2-yl]oxy]-acetic acid

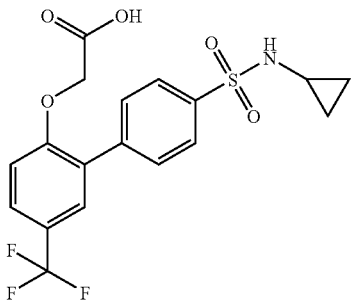

$^1$H NMR CD$_3$OD: δ 7.95-7.84 (m, 4H), 7.64 (dd, 1H), 7.61 (d, 1H), 7.12 (d, 1H), 4.61 (s, 2H), 2.23-2.16 (m, 1H), 0.58-0.53 (m, 4H)
MS: APCI (−ve) 414. .

EXAMPLE 132

[[4'-(Aminosulfonyl)-5-(trifluoromethyl)[1,1'-biphenyl]-2-yl]oxy]-acetic acid

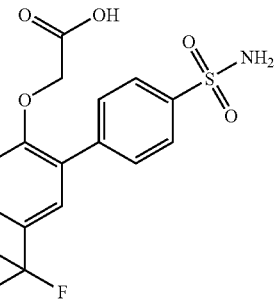

$^1$H NMR CD$_3$OD: δ 7.94 (d, 2H), 7.81 (d, 2H), 7.63 (dd, 1H), 7.58 (d, 1H), 7.12 (d, 1H), 4.60 (s, 2H).
MS: APCI (−ve) 374.

EXAMPLE 133

[[4'-[(Methylamino)sulfonyl]-5-(trifluoromethyl)[1,1'-biphenyl]-2-yl]oxy]-acetic acid

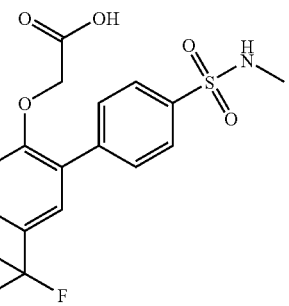

$^1$H NMR CD$_3$OD: δ 7.80-7.74 (m, 4H), 7.53 (dd, 1H), 7.50 (d, 1H), 4.48 (s, 2H), 2.47 (s, 3H).
MS: APCI (−ve) 388

EXAMPLE 134

[[4'-[(4-Methyl-1-piperazinyl)sulfonyl]-5-(trifluoromethyl)[1,1'-biphenyl]-2-yl]oxy]-acetic acid

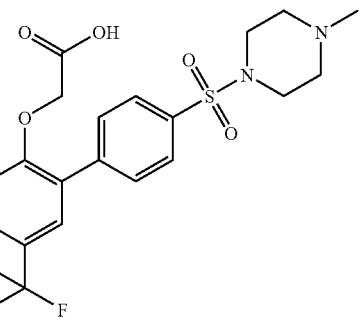

$^1$H NMR CD$_3$OD: δ 7.85-7.70 (m, 4H), 7.55-7.51 (m, 1H), 7.49 (d, 1H), 7.00 (d, 1H), 4.41 (s, 2H), 3.03-2.95 (m, 4H), 2.48 (t, 4H), 2.21 (s, 3H).
MS: APCI (−ve) 457

EXAMPLE 135

[2-[4-Methyl-2-(5-methyl-1,1-dioxido-1,2,5-thiadiazolidin-2-yl)-5-pyrimidinyl]-4-(trifluoromethyl)phenoxy]-acetic acid

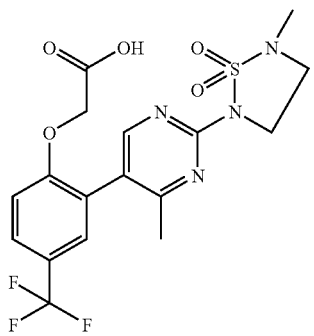

(i) 2,5-Dibromo-4-methyl-pyrimidine

Isoamylnitrite (21 ml) was added to a stirred suspension of 5-bromo-4-methyl-2-pyrimidinamine (1.75 g) in bromoform (30 ml) and the mixture heated at 85° C. for 4 h. After cooling, isohexane (300 ml) was added and the solution passed through a pad of silica-gel. The silica was washed with petrol (1000 ml), dichloromethane (200 ml) then the product eluted with ethylacetate. The ethylacetate layer was evaporated under reduced pressure and the residue purified by chromatography on silica eluting with 5% diethylether/isohexane, yield 0.9 g $^1$H NMR CDCl$_3$: δ 8.52 (s, 1H), 2.64 (s, 3H)
MS: APCI (−ve) 249/51/53

(ii) 5-Bromo-4-methyl-2-(5-methyl-1,1-dioxido-1,2,5-thiadiazolidin-2-yl)-pyrimidine Sodium hydride (0.128 g, 60% disp. in oil) was added to a stirred solution of 2-methyl-1,2,5-thiadiazolidine 1,1-dioxide (0.433 g) in THF (10 ml). DMF (10 ml) was added and the mixture heated at 80° C. for 5 min then a solution of the product from step (i) (0.8 g) in DMF (5 ml) was added. The mixture was heated at 60° C. for 10 min, poured into water (100 ml), acidified with citric acid and extracted with ethylacetate. The organics were evaporated under reduced pressure and the residue purified by chromatography on silica eluting with diethylether, yield 0.58 g.

$^1$H NMR CDCl$_3$: δ 8.50 (s, 1H), 4.05 (t, 2H), 3.45 (t, 2H), 2.87 (s, 31), 2.58 (s, 3H).
MS: APCI (+ve) 307/9

(iii) [2-[4-Methyl-2-(5-methyl-1,1-dioxido-1,2,5-thiadiazolidin-2-yl)-5-pyrimidinyl]-4-(trifluoromethyl)phenoxy]-acetic acid The title compound was prepared by the method of example 44, yield 0.05 g.

$^1$H NMR CDCl$_3$: δ 8.34 (s, 1H), 7.47 (dd, 1H), 7.32 (d, 1H), 6.90 (d, 1H), 4.36 (s, 2H), 4.05 (t, 2H), 3.40 (t, 41), 2.77 (s, 3H), 2.27 (s, 3H).
MS: APCI (+ve) 447

EXAMPLE 136-137

The following compounds were synthesised in an analogous method to example 135

EXAMPLE 136

[2-[4-Methyl-2-[methyl(methylsulfonyl)amino]-5-pyrimidinyl]-4-(trifluoromethyl)phenoxy]-acetic acid

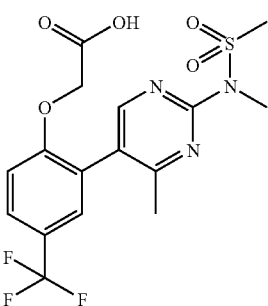

$^1$H NMR CDCl$_3$: δ 8.37 (s, 1H), 7.63 (dd, 1H), 7.40 (d, 1H), 6.96 (d, 1H), 4.60 (s, 2H), 3.57 (s, 3H), 3.53 (s, 3H), 2.40 (s, 3H).
MS: APCI (−ve) 418

EXAMPLE 137

[2-[2-(1,1-Dioxido-2-isothiazolidinyl)-4-methyl-5-pyrimidinyl]-4-(trifluoromethyl)phenoxy]-acetic acid, ammonium salt

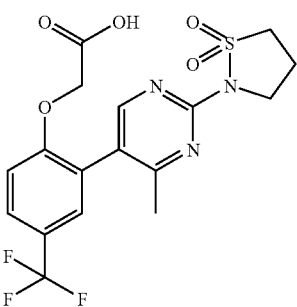

$^1$H NMR CDCl$_3$: δ 8.37 (s, 1H), 7.60 (dd 1H), 7.36 (d, 1H), 7.02 (d, 1H), 4.53 (s, 2H), 4.09 (t, 2H), 3.49 (t, 2H), 2.51 (quintet, 2H), 2.39 (s, 3H).
MS: APCI (+ve) 432.

EXAMPLE 138

[2-[2-(3-Hydroxy-1-azetidinyl)-4-methyl-5-pyrimidinyl]-4-(trifluoromethyl)phenoxy]-acetic acid

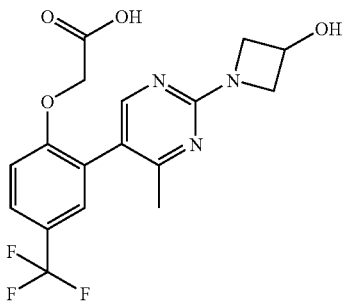

(i) 1-(5-Bromo-4-methyl-2-pyrimidinyl)-3-azetidinol

A mixture of the product from example 135 step (i) (0.75 g), azetidin-3-ol hydrochloride (0.66 g) and triethylamine (0.9 ml) in ethanol (10 ml) was stirred at RT for 2 h. The solvent was removed under reduced pressure and the residue purified by chromatography on silica eluting with 60% diethylether/isohexane as eluant, yield 0.7 g.

$^1$H NMR CDCl$_3$: δ 8.22 (s, 1H), 4.78-4.72 (m, 1H), 4.40-4.33 (m, 2H), 3.99-3.93 (m, 2H), 2.45 (s, 3H)

(ii) [2-[2-(3-Hydroxy-1-azetidinyl)-4-methyl-5-pyrimidinyl]-4-(trifluoromethyl)phenoxy]-acetic acid The title compound was prepared in an analogous method to example 44, yield 0.04 g.

$^1$H NMR CD$_3$OD: δ 8.09 (s, 1H), 7.64 (m, 1H), 7.43 (d, 1H), 7.08 (d, 1H), 4.71-4.64 (m, 1H), 4.61 (s, 2H), 4.41-4.34 (m, 2H), 3.96-3.91 (m, 2H), 2.25 (s, 3H).

MS: APCI (+ve) 384

EXAMPLE 139-141

The following compounds were synthesised in an analogous method to example 138

EXAMPLE 139

[2-[4-Methyl-2-(4-methyl-1-piperazinyl)-5-pyrimidinyl]-4-(trifluoromethyl)phenoxy]-acetic acid

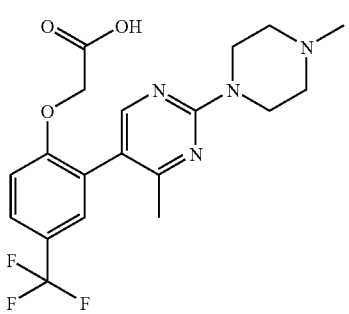

$^1$H NMR CDCl$_3$: δ 8.19 (s, 1H), 7.57 (d, 1H—), 7.38 (d, 1H), 6.99 (d, 1H), 4.51 (s, 2H), 4.3-3.8 (br s, 4H), 3-2.8 (br s, 4H), 2.63 (s, 3H), 2.29 (s, 3H).

MS: APCI (+ve) 411

EXAMPLE 140

[2-[4-Methyl-2-(1-pyrrolidinyl)-5-pyrimidinyl]-4-(trifluoromethyl)phenoxy]-acetic acid

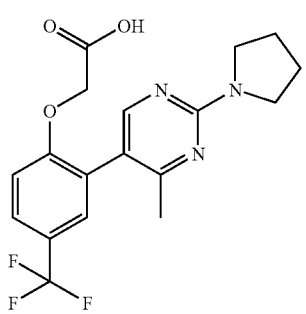

$^1$H NMR CD$_3$OD: δ 7.95 (s, 1H), 7.36 (d, 1H), 7.59-7.54 (m, 1H), 7.01 (d, 1H), 4.65 (s, 2H), 3.50 (t, 4H), 2.15 (s, 3H), 1.96-1.91 (m, 4H).

MS: APCI (+ve) 382

EXAMPLE 141

[2-[2-(Dimethylamino)-4-methyl-5-pyrimidinyl]-4-(trifluoromethyl)phenoxy]-acetic acid

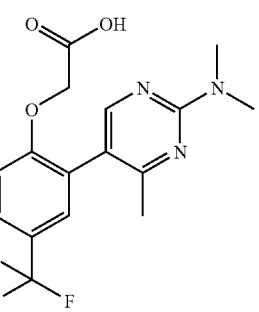

$^1$H NMR CD$_3$OD: δ 8.05 (s, 1H), 7.67-7.63 (m, 1H), 7.44 (d, 1H), 7.10 (d, 1H), 4.75 (s, 2H), 3.20 (s, 6H).

MS: APCI (+ve) 356

EXAMPLE 142

[2-[5-Methyl-2-[methyl(methylsulfonyl)amino]-4-pyrimidinyl]-4-(trifluoromethyl)phenoxy]-acetic acid

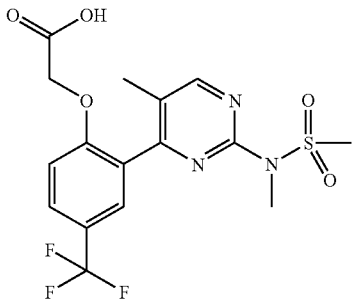

(i) N-(4-Chloro-5-methyl-2-pyrimidinyl)-N-methyl-methanesulfonamide

A mixture of N-methylsulphonamide (3.35 g), 2,4-dichloro-5-methylpyrimidine (5 g) and potassium carbonate (4.3 g) in DMF (50 ml) was heated at 80° C. for 4 h. The reaction was quenched with water (200 ml) and extracted with ethylacetate. The organics were dried, evaporated under reduced pressure and the residue triturated with ether. The solid was filtered off (4-isomer) and the filtrate evaporated under reduced pressure and subjected to RPHPLC to obtain the 2-isomer, yield 0.37 g.
$^1$H NMR CDCl$_3$: δ 8.35 (s, 1H), 3.51 (s, 3H), 3.48 (s, 3H), 2.29 (d, 3H).

(ii) [2-[5-Methyl-2-[methyl(methylsulfonyl)amino]-4-pyrimidinyl]-4-(trifluoromethyl)phenoxy]-acetic acid The title compound was prepared in an analogous method to example 44, yield 0.04 g.
$^1$H NMR CD$_3$OD: δ 8.50 (s, 1H), 7.16 (d, 1H), 7.74 (dd, 1H), 7.62 (d, 1H), 4.68 (s, 2H), 3.50 (s, 3H), 3.45 (s, 3H), 2.19 (s, 3H).
MS: APCI (+ve) 420

EXAMPLE 143

[2-[2-[[(Dimethylamino)sulfonyl]amino]-4-methyl-5-pyrimidinyl]-4-(trifluoromethyl)phenoxy]-acetic acid

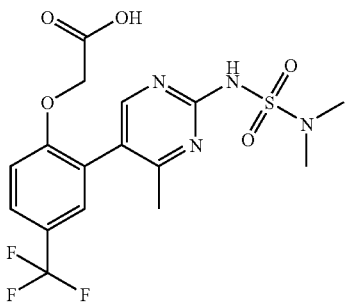

(i) N'-(5-Bromo-4-methyl-2-pyrimidinyl)-N,N-dimethyl-sulfamide

A mixture of 5-bromo-4-methyl-2-pyrimidinamine (0.75 g) and dimethylsulphonyl chloride (0.43 ml) in pyridine (20 ml) was heated at 80° C. for 17 h. The solvent was removed under reduced pressure and the residue purified by chromatography on silica eluting with diethylether then ethylacetate. The residue was then purified by RPHPLC, yield 0.12 g.
MS: APCI (−ve) 295/6

(ii) [2-[2-[[(Dimethylamino)sulfonyl]amino]-4-methyl-5-pyrimidinyl]-4-(trifluoromethyl)phenoxy]-acetic acid The title compound was prepared in an analogous method to example 44, yield 0.01 g.
$^1$H NMR CD$_3$OD: δ 8.27 (s, 1H), 7.68 (d, 1H), 7.49 (s, 1H), 7.11 (d, 1H), 4.70 (s, 2H), 2.98 (s, 6H), 2.32 (s, 3H).
MS: APCI (+ve) 435.

EXAMPLE 144

[[2'-Chloro-4'-[(methoxycarbonyl)amino]-5-(trifluoromethyl)[1,1'-biphenyl]-2-yl]oxy]acetic acid

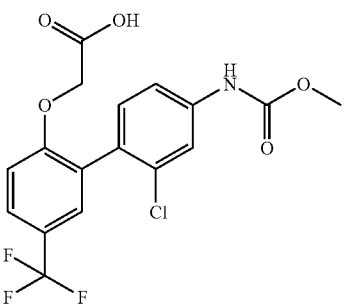

i) 2-Chloro-2'-(phenylmethoxy)-5'-(trifluoromethyl)-[1,1'-biphenyl]-4-amine

The product from example 32 step (ii) (0.5 g) and 4-bromo-3-chloroaniline (0.38 g) were dissolved in toluene (4 ml). Ethanol (1 ml), 2M aqueous sodium carbonate (1 ml) and Pd(PPh$_3$)$_4$ (0.115 g) were added sequentially and the mixture heated at reflux for 4 h. The reaction was cooled, evaporated, dissolved in EtOAc, washed with water and brine, dried (MgSO$_4$) and evaporated. The residue was purified by chromatography on silica eluting with 10% EtOAc/isohexane. Yield 0.23 g.
$^1$H NMR DMSO-d6: δ 7.67 (ddd, 1H), 7.4 (d, 1H), 7.27-7.34 (m, 6H), 7.01 (d, 1H), 6.7 (d, 1H), 6.55 (dd, 1H), 5.47 (s, 2H) 5.18 (s, 2H)

ii) 4'-Amino-2'-chloro-5-(trifluoromethyl)-[1,1'-biphenyl]-2-ol

5% Pt/C (0.088 g) was added to a solution of the product from step (i) in ethanol (20 ml) and hydrogenated at RT and 1 bar for 18 h. Extra Pt/C (0.1 g) was added and hydrogenated for a further 3 h at 2 bar. The catalyst was removed by filtration and the filtrate evaporated to leave a solid residue. The residue was purified by chromatography on silica eluting with 50% EtOAc/isohexane. Yield 0.083 g.
$^1$H NMR DMSO-d6: δ 10.2 (s, 1H), 7.49 (d, 1H), 7.3 (d, 1H), 7.03 (d, 1H), 6.96 (d, 1H), 6.68 (d, 1H), 6.54 (dd, 1H), 5.44 (s, 2H)

iii) [[4'-Amino-2'-chloro-5-(trifluoromethyl)-[1,1'-biphenyl]-2-yl]oxy]acetic acid, 1,1-dimethylethyl ester The subtitle compound was prepared by the method of example 1 step (i) using the product from step (ii). Yield 0.07 g. Used in step (iv) without characterisation.

iv) [[2'-Chloro-4'-[(methoxycarbonyl)amino]-5-(trifluoromethyl)-[1,1'-biphenyl]-2-yl]oxy]acetic acid, 1,1-dimethylethyl ester The product from step (iii) (0.07 g) was dissolved in DCM (5 ml), triethylamine (0.024 ml) added, followed by methyl chloroformate (0.013 ml) and stirred for 20 h. Further triethylamine (0.024 ml) and methyl chloroformate (0.013 ml) were added three times over to achieve complete reaction. The solvent was removed by evaporation to give the crude product which was carried forward to step (v) without characterisation.

v) [[2'-Chloro-4'-[(methoxycarbonyl)amino]-5-(trifluoromethyl)-[1,1'-biphenyl]-2-yl]oxy]acetic acid The title compound was prepared by the method of example 1 step (iii) using the product from step (iv).
$^1$H NMR DMSO-d6: δ 9.94 (s, 1H), 7.69 (dd, 2H), 7.41-7.47 (m, 2H), 7.35 (d, 1H), 7.13 (d, 1H), 4.65 (s, 2H), 3.7 (s, 3H)
MS: APCI (−ve) 402

EXAMPLE 145

2-[[2'-Chloro-4'-(methylsulfonyl)-5-(trifluoromethyl)[1,1'-biphenyl]-2-yl]oxy]-(2S)-propanoic acid

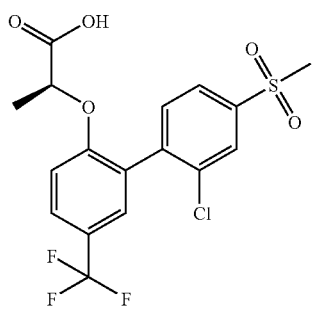

i) 2-Chloro-1-iodo-4-(methylthio)benzene

Sodium methanethiolate (5 g) was added to a solution of 4-fluoro-2-chloro-iodobenzene (18.3 g) and stirred for 20 h. The mixture was poured into water, extracted with ether, washed with brine, dried (MgSO$_4$) and evaporated. Yield 18.5 g.
$^1$H NMR DMSO-d6: δ 7.81 (d, 1H), 7.43 (dd, 1H), 6.98 (dd, 1H), 3.32 (s, 3H)

ii) 2-Chloro-1-iodo-4-(methylsulfonyl)benzene

Mcpba (8.6 g) was added portionwise to a stirred solution of the product from step (i) (5 g) in DCM (100 ml). After 1 h, the reaction was diluted with DCM (200 ml), washed with saturated aqueous sodium bicarbonate, dried (MgSO$_4$) and evaporated under reduced pressure. Yield 3.2 g $^1$H NMR DMSO-d6: δ 8.26 (d, 1H), 8.06 (d, 1H), 7.59 (dd, 1H), 3.32 (s, 3H)

iii) 2'-Chloro-4'-(methylsulfonyl)-5-(trifluoromethyl)-[1,1'-biphenyl]-2-yl]oxy]methyl]benzene The subtitle compound was prepared by the method of example 144 step (i) using the product from step (ii) and the product from example 32 step (ii). Yield 2.2 g
$^1$H NMR DMSO-d6: δ 8.11 (s, 1H), 7.95 (dd, 1H), 7.82 (d, 1H), 7.72 (d, 1H), 7.61 (d, 1H), 7.41 (d, 1H), 7.27-7.36 (m, 5H), 5.25 (s, 2H), 3.35 (s, 3H)

iv) 2'-Chloro-4'-(methylsulfonyl)-5-(trifluoromethyl)-[1,1'-biphenyl]-2-ol

The subtitle compound was prepared by the method of example 144 step (ii) using the product from step (iii). Yield 0.95 g
$^1$H NMR DMSO-d6: δ 10.72 (s, 1H), 8.08 (d, 1H), 7.93 (dd, 1H), 7.63-7.68 (m, 2H), 7.49 (d, 1H), 7.14 (d, 1H), 3.35 (s, 3H)
MS: APCI (−ve) 349 v) 2-[[2'-Chloro-4'-(methylsulfonyl)-5-(trifluoromethyl)[1,1'-biphenyl]-2-yl]oxy]-(2S)-propanoic acid, 1,1-dimethylethyl ester The subtitle compound was prepared by the method of example 32 step (v) using the product from step (iv) and tert-butyl R-lactate. Yield 0.25 g.
$^1$H NMR DMSO-d6: δ 8.11 (d, 1H), 7.97 (d, 1H), 7.82 (dd, 1H), 7.73 (d, 1H), 7.62 (d, 1H), 7.15 (d, 1H), 5.0 (brs, 1H), 3.36 (s, 3H), 1.36-1.39 (m, 12H)

vi) 2-[[2'-Chloro-4'-(methylsulfonyl)-5-(trifluoromethyl)[1,1'-biphenyl]-2-yl]oxy]-(2S)-propanoic acid The title compound was prepared by the method of example 1 step (iii) using the product from step (v). Yield 0.12 g.
$^1$H NMR DMSO-d6: δ 8.09 (d, 1H), 7.95 (dd, 1H), 7.82 (s, 1H), 7.76 (dd, 1H), 7.58 (d, 1H), 7.14 (d, 1H), 4.87 (q, 1H), 3.36 (s, 3H), 1.35 (d, 3H)
MS: APCI (−ve) 421

EXAMPLE 146

2-[[3'-Cyano-5-(trifluoromethyl)[1,1'-biphenyl]-2-yl]oxy]-(2S)-propanoic acid

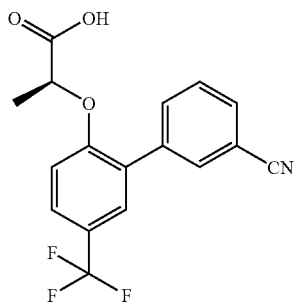

i) 4,4,5,5-Tetramethyl-2-[2-(phenylmethoxy)-5-(trifluoromethyl)phenyl]-1,3,2-dioxaborolane Pinacol (1.82 g) was added to a solution of the product from example 32 step (ii) (4.54 g) in ether (40 ml) and stirred at RT for 20 h. The reaction was diluted with ether (100 ml), washed with brine, dried (MgSO$_4$) and evaporated. Yield 5.7 g.

$^1$H NMR DMSO-d6: δ 7.82 (d, 1H), 7.79 (d, 1H), 7.6 (d, 2H), 7.4 (t, 2H), 7.32 (d, 1H), 7.27 (d, 1H), 5.24 (s, 2H), 1.32 (s, 12H)

ii) 2-(4,4,5,5-Tetramethyl-1,3,2-dioxaborolan-2-yl)-4-(trifluoromethyl)phenol 10% Pd/C (0.5 g) was added to a solution of the product from step (i) in EtOAc (80 ml) and hydrogenated at RT and 1 bar for 1 h, and for a further 3 h at 3 bar. The catalyst was removed by filtration and the filtrate evaporated to leave a solid product. Yield 4.2 g.

$^1$H NMR DMSO-d6: δ 9.99 (d, 1H), 7.72 (s, 1H), 7.63 (d, 1H), 6.99 (d, 1H), 1.3 (d, 12H)

iii) 2-[2-(4,4,5,5-Tetramethyl-1,3,2-dioxaborolan-2-yl)-4-(trifluoromethyl)phenoxy]-(2S)-propanoic acid, 1,1-dimethylethyl ester The subtitle compound was prepared by the method of example 32 step (v) using the product from step (ii) and tert-butyl R-lactate. Yield 4.0 g. The crude material was carried forward to step (iv).

iv) 2-[2-Borono-4-(trifluoromethyl)phenoxy]-(2S)-propanoic acid

TFA (10 ml) was added to a solution of the product from step (iii) (4.0 g) in DCM (100 ml) and stirred for 30 min. The TPA was evaporated and the residue dissolved in a mixture of 1M hydrochloric acid (30 ml) and acetonitrile (30 ml) After 1 h the mixture was evaporated to dryness, dissolved in 1M sodium hydroxide, washed with ether and adjusted to pH 2 with concentrated hydrochloric acid. The aqueous was then extracted with ether, washed with brine, dried (MgSO$_4$) and evaporated. Yield 2.0 g. The crude material was carried forward to step (v).

v) 2-[[3'-Cyano-5-(trifluoromethyl)[1,1'-biphenyl]-2-yl]oxy]-(2S)-propanoic acid The title compound was prepared by the method of example 144 step (i) using the product from step (iv) and 3-bromobenzonitrile.

$^1$H NMR DMSO-d6: δ 8.13 (t, 1H), 8.01 (tdt, 1H), 7.85 (dt, 1H), 7.71-7.76 (m, 2H), 7.65 (dt, 1H), 7.17-7.2 (m, 1H), 5.11 (q, 1H), 1.47 (d, 3H)

MS: APCI (–ve) 334

EXAMPLE 147

2-[[4'-[(Dimethylamino)sulfonyl]-5-(trifluoromethyl)[1,1'-biphenyl]-2-yl]oxy]-(2S)-propanoic acid

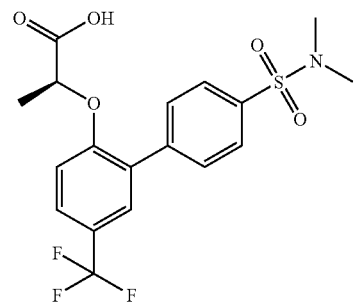

The title compound was prepared by the method of example 144 step (i) using the product from example 146 step (iv) and 4-bromo-N,N-dimethyl-benzenesulfonamide.

$^1$H NMR DMSO-d6: δ 7.95 (d, 2H), 7.83 (d, 2H), 7.77 (d, 1H), 7.73 (s, 1H), 7.21 (d, 1H), 5.14 (q, 1H), 2.69 (s, 6H), 1.51 (d, 3H)

MS: APCI (–ve) 416

EXAMPLE 148

2-[[2'-Chloro-4'-[(dimethylamino)sulfonyl]-5-(trifluoromethyl)[1,1'-biphenyl]-2-yl]oxy]-(2S)-propanoic acid

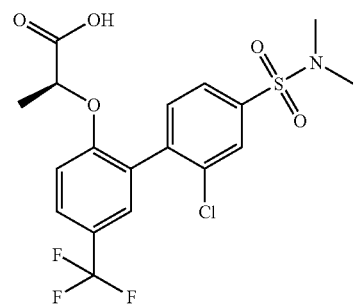

i) 3-Chloro-4-iodobenzenesulfonamide

A solution of sodium nitrite (3.27 g) in water was added dropwise over 1 h to a stirred solution of 3-chloro-4-iodoaniline (10.0 g) in a mixture of THF (120 ml) and concentrated hydrochloric acid (50 ml) at –5 to –1° C. Magnesium chloride (6.39 g) was then added and the resulting mixture poured into a stirred solution of acetic acid (50 ml) saturated with sulfur dioxide and containing cuprous chloride (2.14 g). After heating at 34° C. for 30 min, the mixture was poured into brine, extracted with EtOAc, washed with aqueous sodium bicarbonate and brine, dried (MgSO$_4$) and evaporated. The residue was dissolved in THF (100 ml), 0.880 ammonia (100 ml) added and stirred for 2 h. The mixture was diluted with brine, extracted with EtOAc, washed with brine, dried (MgSO$_4$) and evaporated. The residue was treated with isohexane/ether (4:1) and filtered to give the subtitle compound. Yield 5.67 g.

$^1$H NMR DMSO-d6: δ 8.18 (d, 1H), 7.92 (d, 1H), 7.56 (s, 1H), 7.47 (dd, 1H)

ii) 3-Chloro-4-iodo-N,N-dimethylbenzenesulfonamide

Sodium hydride (0.33 g) was added to a solution of the product from step (i) (1.2 g) in DMF (25 ml) and stirred for 20 min. Methyl iodide (0.5 ml) was added dropwise and then stirred for a further 1 h. The reaction mixture was quenched with water, extracted with EtOAc, dried (MgSO$_4$) and evaporated. The residue was treated with ether to give to give the subtitle compound as a white solid. Yield 0.45 g.

$^1$H NMR DMSO-d6: δ 8.05 (d, 1H), 7.82 (d, 1H), 7.31 (dd, 1H), 2.75 (s, 6H)

iii) 2-[[2'-Chloro-4'-[(dimethylamino)sulfonyl]-5-(trifluoromethyl)[1,1'-biphenyl]-2-yl]oxy]-(2S)-propanoic acid The title compound was prepared by the method of example 144 step (i) using the product from step (ii) and the product from example 146 step (iv).

$^1$H NMR DMSO-d6: δ 7.86 (t, 1H), 7.75-7.79 (m, 3H), 7.61 (d, 1H), 7.14 (d, 1H), 4.88 (q, 1H), 2.7 (s, 6H), 1.35 (d, 3H)

MS: APCI (−ve) 450

EXAMPLE 149

2-[[2'-Fluoro-4'-(methylsulfonyl)-5-(trifluoromethyl)[1,1'-biphenyl]-2-yl]oxy]-(2S)-propanoic acid

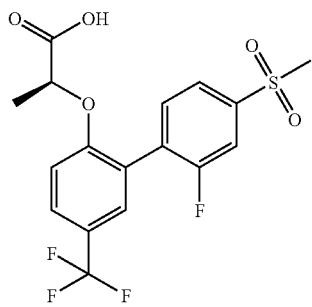

i) Trifluoromethanesulfonic acid, 2-fluoro-4-(methylsulfonyl)phenyl ester

2-Fluoro-4-(methylsulfonyl)phenol (1.44 g) was dissolved in DCM (20 ml), triethylamine (1.17 ml) added, followed by trifluoromethanesulfonic anhydride (1.57 ml) and stirred for 1 h. The solution was washed with brine, dried (MgSO$_4$) and evaporated to give the subtitle compound.

$^1$H NMR CDCl$_3$: δ 7.83-7.92 (m, 2H), 7.55-7.61 (m, 1H), 3.11 (s, 3H)

ii) 2-[[2'-Fluoro-4'-(methylsulfonyl)-5-(trifluoromethyl)[1,1'-biphenyl]-2-yl]oxy]-(2S)-propanoic acid The title compound was prepared by the method of example 144 step (i) using the product from step (i) and the product from example 146 step (iv).

$^1$H NMR DMSO-d6: δ 7.79-7.9 (m, 3H), 7.74 (dd, 1H), 7.64 (s, 1H), 7.12 (d, 1H), 4.87 (q, 1H), 3.31 (s, 3H), 1.35 (d, 3H)

MS: APCI (−ve) 405

EXAMPLE 150

[[2',5-Dichloro-4'-(methylsulfonyl)[1,1'-biphenyl]-2-yl]oxy]-(2S)-propanoic acid

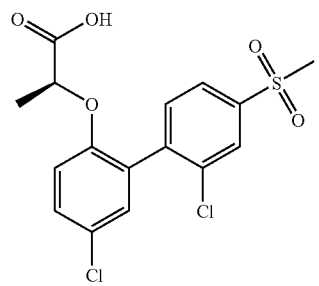

i) [[[2',5-Dichloro-4'-(methylsulfonyl)[1,1'-biphenyl]-2-yl]oxy]methyl]benzene The subtitle compound was prepared by the method of example 144 step (i) using the product from example 16 step (ii) and the product from example 145 step (ii). Yield 1.08 g.

$^1$H NMR DMSO-d6: δ 8.09 (d, 1H), 7.94 (dd, 1H), 7.67 (d, 1H), 7.49 (dd, 1), 7.22-7.34 (m, 7H), 5.14 (s, 2H), 3.35 (s, 3H)

ii) [[[2',5-Dichloro-4'-(methylsulfonyl)[1,1'-biphenyl]-2-ol

The subtitle compound was prepared by the method of example 144 step (ii) using the product from step (i). Yield 0.45 g.

$^1$H NMR DMSO-d6: δ 10.04 (s, 1H), 8.06 (d, 1H), 7.91 (dd, 1H), 7.63 (d, 1H), 7.32 (dd, 1H), 7.2 (d, 1H), 6.97 (d, 1H), 3.34 (s, 3H)

iii) [[2',5-Dichloro-4'-(methylsulfonyl)[1,1'-biphenyl]-2-yl]oxy]-(2S)-propanoic acid, 1,1-dimethylethyl ester The subtitle compound was prepared by the method of example 32 step (v) using the product from step (ii) and tert-butyl R-lactate. Yield 0.24 g.

$^1$H NMR DMSO-d6: δ 8.09 (d, 1H), 7.95 (d, 1H), 7.7 (d, 1H), 7.48 (dd, 1H), 7.33 (d, 1H), 6.98 (d, 1H), 4.85 (brs, 1H), 3.35 (s, 3H), 1.37 (s, 9H), 1.32 (d, 3H)

iv) [[2',5-Dichloro-4'-(methylsulfonyl)[1,1'-biphenyl]-2-yl]oxy]-(2S)-propanoic acid The title compound was prepared by the method of example 1 step (iii) using the product from step (iii). Yield 0.11 g.

$^1$H NMR DMSO-d6: δ 8.07 (d, 1H), 7.92 (dd, 1H), 7.81 (s, 1H), 7.42 (dd, 1H), 7.28 (d, 1H), 6.97 (d, 1H), 4.65 (q, 1H), 3.35 (s, 3H), 1.29 (d, 3H)

MS: APCI (−ve) 387

EXAMPLE 151

[[5-Chloro-4'-[(dimethylamino)sulfonyl][1,1'-biphenyl]-2-yl]oxy]-(2S)-propanoic acid

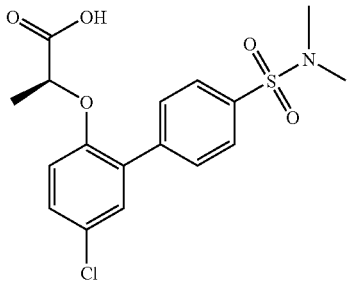

i) 2-[5-Chloro-2-(phenylmethoxy)phenyl]-4,4,5,5-tetramethyl-1,3,2-dioxaboralane The subtitle compound was prepared by the method of example 146 step (i) using the product from example 16 step (ii). Yield 3.3 g.

$^1$H NMR DMSO-d6: δ 7.27-7.64 (m, 7H), 6.85 (d, 1H), 5.09 (s, 2H), 1.36 (s, 12H)

ii) 4-Chloro-2-(4,4,5,5-tetramethyl-1,3,2-dioxaborolan-2-yl)phenol

The subtitle compound was prepared by the method of example 146 step (ii) using the product from step (i). Purified by chromatography on silica eluting with 50% EtOAc/isohexane. Yield 1.89 g.

$^1$H NMR DMSO-d6: δ 7.76-7.79 (s, 1H), 6.79-7.62 (m, 3H), 1.36 (s, 12H)

iii) 2-[4-Chloro-2-(4,4,5,5-tetramethyl-1,3,2 dioxaborolan-2-yl)phenoxy]-(2S)-propanoic acid, 1,1-dimethylethyl ester The subtitle compound was prepared by the method of example 32 step (v) using the product from step (ii) and tert-butyl R-lactate. Yield 3.5 g. The crude material was carried forward to step (iv).

iv) 2-(2-Borono-4-chlorophenoxy)-(2S)-propanoic acid

The subtitle compound was prepared by the method of example 146 step (iv) using the product from step (iii). Yield 2.5 g. The crude material was carried forward to step (v).

v) [[5-Chloro-4'-[(dimethylamino)sulfonyl][1,1'-biphenyl]-2-yl]oxy]-(2S)-propanoic acid The title compound was prepared by the method of example 144 step (i) using the product from step (iv) and 4-bromo-N,N-dimethylbenzenesulfonamide and THF as solvent. Yield (0.068 g).

$^1$H NMR DMSO-d6: δ 8.01 (d, 2H), 7.75 (d, 2H), 7.3-7.41 (m, 2H), 6.93 (d, 1H), 4.56 (bm, 1H), 2.65 (s, 6H), 1.33 (d, 3H)

MS: APCI (−ve) 382

EXAMPLE 152

[[2',5-Dichloro-4'-[(dimethylamino)sulfonyl][1,1'-biphenyl]-2-yl]oxy]-(2S)-propanoic acid

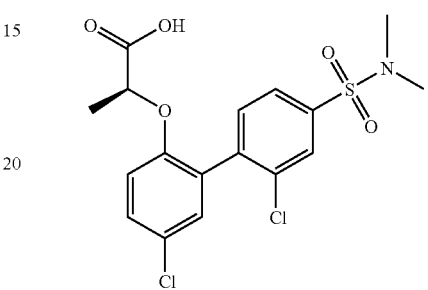

The title compound was prepared by the method of example 144 step (i) using the product from example 151 step (iv), the product from example 148 step (ii) and methanol as solvent. Yield (0.08 g).

$^1$H NMR DMSO-d6: δ 7.9 (bm, 1H), 7.82 (s, 1H), 7.74 (dd, 1H), 7.4 (dd, 1H), 7.26 (d, 1H), 6.92 (d, 1H), 4.34 (bm, 1H), 2.7 (s, 6H), 1.2 (d, 3H)

MS: APCI (−ve) 416

EXAMPLE 153

[(5-Chloro-3'-cyano[1,1'-biphenyl]-2-yl)oxy]-(2S)-propanoic acid

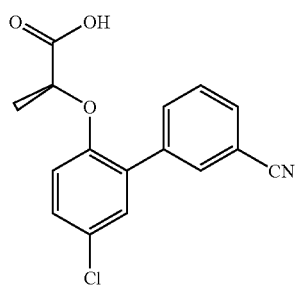

The title compound was prepared by the method of example 144 step (i) using the product from example 151 step (iv), 3-bromobenzenenitrile and THF as solvent.

$^1$H NMR DMSO-d6: δ 8.25 (s, 1H), 8.06 (d, 1H), 7.79 (d, 1H), 7.63 (t, 1H), 7.4 (d, 1H), 7.33 (dd, 1H), 6.95 (d, 1H), 4.64 (q, 1H), 1.32 (d, 3H)

MS: APCI (−ve) 300

EXAMPLE 154

[[5-Chloro-4'-[(dimethylamino)sulfonyl]-2'-fluoro[1,1'-biphenyl]-2-yl]oxy]-(2S)-propanoic acid

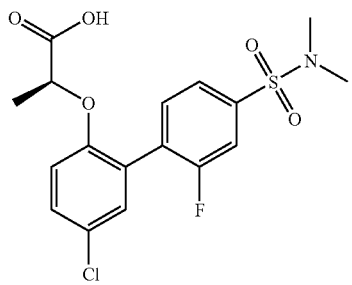

i) 4-Bromo-N,N-dimethyl-3-fluorobenzenesulfonamide

The subtitle compound was prepared by the method of example 148 step (ii) using 4-bromo-3-fluorobenzenesulfonamide 1.14 g.

ii) [[5-Chloro-4'-[(dimethylamino)sulfonyl]-2'-fluoro[1,1'-biphenyl]-2-yl]oxy]-(2S)-propanoic acid The title compound was prepared by the method of example 144 step (i) using the product from step (i), the product from example 151 step (iv) and THF as solvent.

$^1$H NMR DMSO-d6: δ 7.94 (t, 1H), 7.58-7.62 (m, 2H), 7.35-7.4 (m, 2H), 6.93 (d, 1H), 4.48 (q, 1H), 2.7 (s, 6H), 1.26 (d, 3H)

MS: ESI (+ve) 402

EXAMPLE 155

[[5-Chloro-4'-(4-morpholinylsulfonyl)[1,1'-biphenyl]-2-yl]oxy]-(2S)-propanoic acid

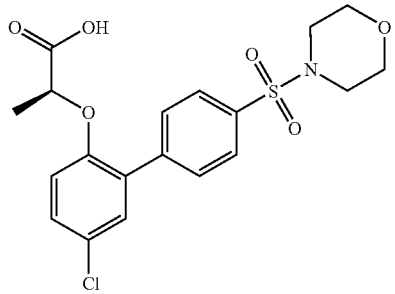

A mixture of the product from example 151 step (iv) (0.126 g), sodium carbonate (0.22 g), 4-[(4-bromophenyl)sulfonyl]morpholine (0.16 g) and Pd(dppf)Cl$_2$ (0.03 g) in dioxane (10 ml) was heated under reflux for 4 h. The mixture was evaporated and purified by RVHPLC (MeCN/aqNH$_4$Cl). Yield 0.09 g.

$^1$H NMR DMSO-d6: δ 8.03 (d, 2H), 7.74 (d, 2H), 7.31-7.39 (m, 2H), 6.93 (d, 1H), 4.55 (m, 1H), 3.65 (m, 2H), 2.92 (m, 2H), 1.34 (d, 3H)

MS: APCI (−ve) 426

EXAMPLE 156

[[5-Chloro-2'-fluoro-4'-(methylsulfonyl)[1,1'-biphenyl]-2-yl]oxy]-(2S)-propanoic acid

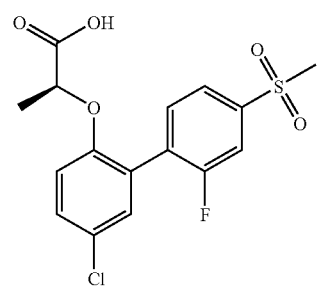

The title compound was prepared by the method of example 155 using the product from example 151 step (iv) and the product from example 149 step (i).

$^1$H NMR DMSO-d6: δ 7.81-7.88 (m, 3H), 7.41-7.49 (m, 2H), 7.0 (d, 1H), 4.9 (q, 1H), 3.3 (s, 3H), 1.37 (d, 3H)

MS: ESI (−ve) 371

EXAMPLE 157

2-[[4'-(1-Azetidinylsulfonyl)-5-chloro[1,1'-biphenyl]-2-yl]oxy]-(2S)-propanoic acid

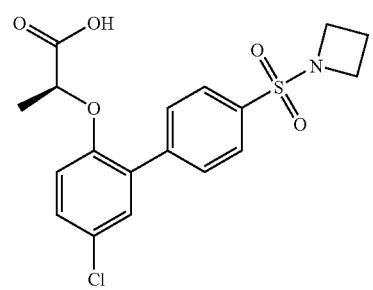

The title compound was prepared by the method of example 144 step (i) using the product from example 151 step (iv), 1-[(4-bromophenyl)sulfonyl]azetidine and THF as solvent. Yield 0.028 g.

$^1$H NMR DMSO-d6: δ 7.97 (d, 2H), 7.82 (d, 2H), 7.39-7.43 (m, 2H), 7.01 (d, 1H), 4.85 (m, 1H), 3.72 (t, 4H), 2.04 (q, 2H), 1.42 (d, 3H)

MS: ESI (−ve) 394

EXAMPLE 158

2-[[5-Chloro-2'-methyl-4'-(1-pyrrolidinylcarbonyl)[1,1'-biphenyl]-2-yl]oxy]-(2S)-propanoic acid, sodium salt

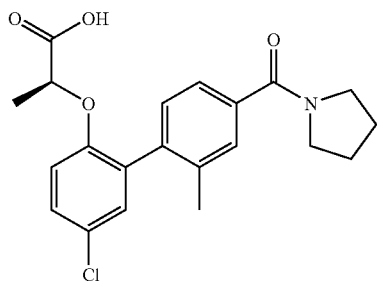

The title compound was prepared by the method of example 155 using the product from example 151 step (iv) and 1-(4-bromo-3-methylbenzoyl)pyrrolidine. Yield 0.152 g.

$^1$H NMR DMSO-d6: δ 7.2-7.41 (m, 4H), 7.25 (s, 1H), 6.85 (d, 1H), 4.22 (m, 1H), 3.56 (m, 4H), 2.2 (s, 3H), 1.85 (m, 4H), 1.17 (d, 3H)

MS: APCI (–ve) 388

EXAMPLE 159

2-[(2',4'-Dichloro-5-cyano[1,1'-biphenyl]-2-yl)oxy]-(2S)-propanoic acid

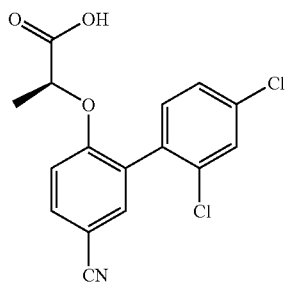

i) 2-(2-Bromo-4-cyanophenoxy)-(2S)-propanoic acid

Diethyl azodicarboxylate (2.12 g) was added to a stirred solution of 2-bromo-4-cyanophenol (2.0 g), methyl-R-lactate (1.47 g) and triphenylphosphine (2.65 g) in THF (80 ml). After 20 h, the mixture was filtered through silica using isohexane/EtOAc as solvent and the filtrate evaporated to dryness. The residue was dissolved in DCM (50 ml), treated with TFA (10 ml) and stirred for 2 h. The solution was evaporated and the residue partitioned between EtOAc and aqueous sodium bicarbonate. The aqueous was acidified with 2M hydrochloric acid, extracted with EtOAc, dried (MgSO$_4$) and evaporated to give the subtitle compound.

$^1$H NMR DMSO-d6: δ 7.87 (s, 1H), 7.56 (d, 1H), 6.83 (d, 1H), 4.91 (q, 1H), 1.7 (d, 3H)

MS: APCI (–ve) 270 ii) 2-[(2',4'-Dichloro-5-cyano[1,1'-biphenyl]-2-yl)oxy]-(2S)-propanoic acid

The title compound was prepared by the method of example 16 step (iii) using the product from step (i) and 2,6-dichlorophenylboronic acid.

$^1$H NM DMSO-d6: δ 7.58-7.78 (m, 4H), 7.46 (d, 1H), 7.02 (d, 1H), 4.51 (q, 1H), 1.26 (d, 3H)

MS: APCI (–ve) 334

EXAMPLE 160

2-[[5-Cyano-2'-fluoro-4'-(trifluoromethyl)[1,1'-biphenyl]-2-yl]oxy]-(2S)-propanoic acid

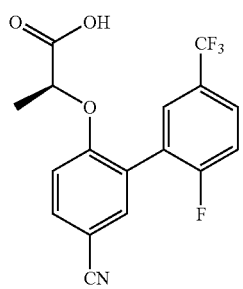

The title compound was prepared by the method of example 16 step (iii) using the product from example 159 step (i) and 3-cyanophenylboronic acid.

$^1$H NMR DMSO-d6: δ 7.81-8.04 (m, 4H), 7.56 (t, 1H), 7.18 (d, 1H), 5.1 (q, 1H), 1.4 (d, 3H)

MS: APCI (–ve) 352

EXAMPLE 161

2-[(3'-Cyano-5-fluoro[1,1'-biphenyl]-2-yl)oxy]-(2S)-propanoic acid, sodium salt

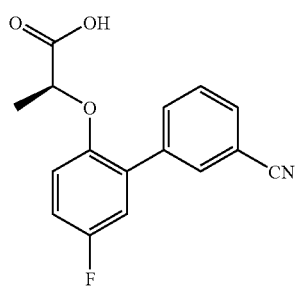

i) 2-(2-Bromo-4-fluorophenoxy)-(2S)-propanoic acid, 1,1-dimethylethyl ester

The subtitle compound was prepared by the method of example 159 step (i) using 2-bromo-4-fluorophenol (2.5 g). Yield 3.0 g.

$^1$H NMR DMSO-d6: δ 7.28-7.32 (m, 1H), 6.89-6.98 (m, 1H), 6.78-6.83 (m, 1H), 4.56 (q, 1H), 1.62 (d, 3H), 1.4 (s, 9H)

ii) 2-(2-Bromo-4-fluorophenoxy)-(2S)-propanoic acid

The subtitle compound was prepared by the method of example 146 step (iv) using the product from step (i). Yield 1.2 g. Carried forward to step (iii) without characterisation.

iii) 2-[(3'-Cyano-5-fluoro[1,1'-biphenyl]-2-yl)oxy]-(2S)-propanoic acid, sodium salt The title compound was prepared by the method of example 155 using the product from step (ii) and 3-cyanophenylboronic acid. The product was dissolved in acetonitrile, treated with 1M sodium hydroxide and evaporated to give the title compound.

¹H NMR DMSO-d6: δ 8.4 (s, 1H), 8.13 (d, 1H), 7.75 (d, 1H), 7.6 (t, 1H), 6.9-7.2 (m, 3H), 4.4 (q, 1H), 1.28 (d, 3H)
MS: APCI (−ve) 284

EXAMPLE 162

2-[(2',4'-Dichloro-5-fluoro[1,1'-biphenyl]-2-yl)oxy]-(2S)-propanoic acid, sodium salt

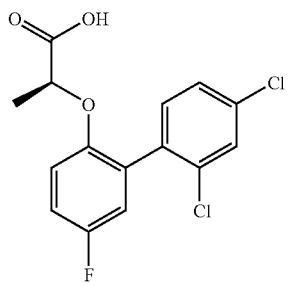

The title compound was prepared by the method of example 155 using the product from example 161 step (ii) and 2,4-dichlorophenylboronic acid. The product was dissolved in acetonitrile, treated with 1M sodium hydroxide and evaporated to give the title compound.

¹H NMR DMSO-d6: δ 7.66-7.72 (m, 2H), 7.43 (d, 1H), 6.86-7.11 (m, 3H), 4.18 (q, 1H), 1.2 (d, 3H)
MS: APCI (−ve) 327

EXAMPLE 163

2-[[2'-Chloro-5-fluoro-4'-(methylsulfonyl)[1,1'-biphenyl]-2-yl]oxy]-(2S)-propanoic acid

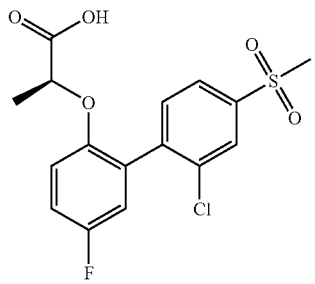

i) Benzyl 2-bromo-fluorophenyl ether

The subtitle compound was prepared by the method of example 16 step (i) using 2-bromo-4-fluorophenol and acetone as solvent. Yield 27.5 g.

¹H NMR DMSO-d6: δ 7.27-7.49 (m, 6H), 6.82-6.99 (m, 2H), 5.12 ii) [2-(Benzyloxy)-5-fluorophenyl]boronic acid

The subtitle compound was prepared by the method of example 16 step (ii) using the product from step (i). Yield 18.77 g.

¹H NMR DMSO-d6: δ 7.9 (s, 21), 7.0-7.5 (m, 8H), 5.14 (s, 2H)

iii) 2-[5-Fluoro-2-(phenylmethoxy)phenyl]-4,4,5,5-tetramethyl-1,3,2-dioxaborolane The subtitle compound was prepared by the method of example 146 step (i) using the product from step (ii). Yield 4.1 g.

¹H NMR DMSO-d6: δ 7.58 (d, 1H), 7.29-7.4 (m, 3H), 7.26 (s, 1H), 7.04 (dt, 1H), 6.84 (d, 2H), 5.07 (s, 2H), 1.36 (s, 12H)

iv) 4-Fluoro-2-(4,4,5,5-tetramethyl-1,3,2-dioxaborolan-2-yl)phenol

The subtitle compound was prepared by the method of example 146 step (ii) using the product from step (iii) and ethanol as solvent.

¹H NMR DMSO-d6: δ 7.63 (s, 1H), 7.2-7.27 (m, 1H), 7.01-7.08 (m, 1H), 6.8-6.83 (m, 1H), 1.37 (s, 12H)

v) 4-Fluoro-2-[2-(4,4,5,5-tetramethyl-1,3,2-dioxaborolan-2-yl)phenoxy]-(2S)-propanoic acid, 1,1-dimethylethyl ester The subtitle compound was prepared by the method of example 32 step (v) using the product from step (iv) and tert-butyl R-lactate. Yield 2.6 g. The crude material was carried forward to step (vi).

vi) 2-[2-Borono-4-(trifluoromethyl)phenoxy]-(2S)-propanoic acid

The subtitle compound was prepared by the method of example 146 step (iv) using the product from step (v). Yield 1.65 g.
MS: APCI (−ve) 227 vii) 2-[[2'-Chloro-5-fluoro-4'-(methylsulfonyl)[1,1'-biphenyl]-2-yl]oxy]-(2S)-propanoic acid The title compound was prepared by the method of example 155 using the product from step (vi) and the product from example 145 step (ii).

¹H NMR DMSO-d6: δ 8.06 (s, 1H), 7.86-7.93 (m, 2H), 7.03-7.23 (m, 2H), 6.9-6.97 (m, 1H), 4.43 (q, 1H), 1.24 (d, 3H)
MS: APCI (−ve) 371

EXAMPLE 164

2-[[2'-Chloro-5-fluoro-5'-(trifluoromethyl)[1,1'-biphenyl]-2-yl]oxy]-(2S)-propanoic acid, sodium salt

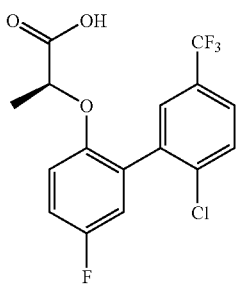

The title compound was prepared by the method of example 155 using the product from example 161 step (ii) and 2-bromo-1-chloro-4-(trifluoromethyl)benzene. The product was dissolved in acetonitrile, treated with 1M sodium hydroxide and evaporated to give the title compound. Yield 0.07 g.
$^1$H NMR DMSO-d6: δ 8.31 (bs, 1H), 7.68-7.77 (m, 2H), 7.09-7.15 (m, 2H), 6.9-6.93 (m, 1H), 4.25 (q, 1H), 1.21 (d, 3H)
MS: APCI (−ve) 361

EXAMPLE 165

[[4'-(Ethylsulfonyl)-6-methyl-5-nitro[1,1'-biphenyl]-2-yl]oxy]acetic acid

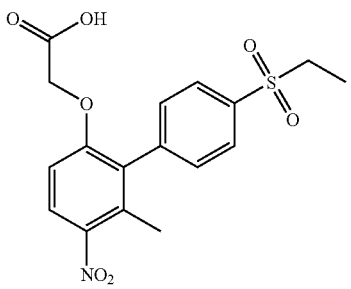

i) (2-Bromo-3-methyl-4-nitrophenoxy)acetic acid, methyl ester

Bromine (5.27 g) in acetic acid (3 ml) was added dropwise to a solution of 3-methyl-4-nitrophenol (5.04 g) in acetic acid (43 ml) over 45 mins, and then stirred for a further 1 h. The solvent was evaporated, water added, extracted with ether, dried (Na$_2$SO$_4$) and evaporated. The crude material was dissolved in DMF (10 ml), potassium carbonate (3.79 g) added, followed by methyl bromoacetate (3.37 ml) and the mixture stirred at RT for 30 mins and 60° C. for 2 h. The mixture was cooled and poured into a mixture of EtOAc and water. The organic phase was separated, washed with water, aqueous potassium carbonate and brine, dried (Na$_2$SO$_4$) and evaporated. The residue was recrystallised from toluene/isohexane. Yield 1.8 g.

$^1$H NMR CDCl$_3$: δ 7.86 (d, 1H), 6.69 (d, 1H), 4.81 (s, 2H), 3.83 (s, 3H), 2.19 (s, 3H).

(ii) [[4'-(Ethylsulfonyl)-6-methyl-5-nitro[1,1'-biphenyl]-2-yl]oxy]acetic acid, methyl ester The subtitle compound was prepared by the method of example 1 step (ii) using the product from step (i) (1.78 g) and 4-(ethylthio)phenylboronic acid (1.6 g). Yield 2.59 g.
$^1$H NMR CDCl$_3$: δ 8.02 (d, 1H), 8.0 (d, 2H), 7.45 (d, 2H), 6.75 (d, 1H), 4.65 (s, 2H), 3.76 (s, 3H), 3.2 (q, 2H), 2.25 (s, 3H) 1.36 (t, 3H)

(iii) [[4'-(Ethylsulfonyl)-6-methyl-5-nitro[1,1'-biphenyl]-2-yl]oxy]acetic acid

The title compound was prepared by the method of example 26 step (vi) using the product from step (ii). Yield 0.22 g.
$^1$H NMR DMSO-d6: δ 13.16 (bs, 1H—), 8.06 (d, 1H), 7.97 (d, 2H), 7.57 (d, 2H), 7.12 (d, 1H), 4.8 (s, 2H), 3.38 (q, 2H), 2.14 (s, 3H) 1.16 (t, 3H).
MS: APCI (+ve): 412 (M+MeOH+H$^+$)

EXAMPLE 166

[[5-Chloro-4'-(ethylsulfonyl)-6-methyl[1,1'-biphenyl]-2-yl]oxy]acetic acid

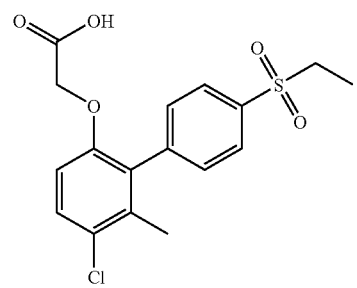

i) [[5-Amino-4'-(ethylsulfonyl)-6-methyl[1,1'-biphenyl]-2-yl]oxy]acetic acid, methyl ester 10% Pd/C (0.15 g) was added to a solution of the product from example 165 step (ii) in EtOAc (20 ml) was hydrogenated at RT and 3 bar for 2 h. The mixture was filtered through celite and the filtrate evaporated to give the sub-title compound. Yield 1.4 g.
$^1$H NMR CDCl$_3$: δ 7.95 (d, 2H), 7.48 (d, 2H), 6.7 (d, 1H), 6.65 (d, 1H), 4.4 (s, 2H), 3.71 (s, 3H), 3.51 (bs, 2H), 3.18 (q, 2H), 1.88 (s, 3H) 1.34 (t, 3H)

ii) [[5-Chloro-4'-(ethylsulfonyl)-6-methyl[1,1'-biphenyl]-2-yl]oxy]acetic acid, methyl ester Cuprous chloride (0.18 g) was dissolved in acetonitrile (6 ml), isopentylamine (0.24 ml) added, followed by the dropwise addition of a solution of the product from step (i) in acetonitrile (6 ml). The mixture was stirred for 12 h, evaporated and purified by chromatography on silica eluting with 30-50% ether/isohexane. Yield 2.59 g.

¹H NMR CDCl₃: δ 7.97 (d, 2H), 7.46 (d, 2H), 7.34 (d, 1H), 6.65 (d, 1H), 4.32 (s, 2H), 3.73 (s, 3H), 3.19 (q, 2H), 2.09 (s, 3H) 1.35 (t, 3H)

iii) [[5-Chloro-4'-(ethylsulfonyl)-6-methyl[1,1'-biphenyl]-2-yl]oxy]acetic acid The title compound was prepared by the method of example 26 step (vi) using the product from step (ii). Purified by RPHPLC (MeCN/aqNH₄Cl). Yield 0.07 g.
¹H NMR DMSO-d6: δ 7.94 (d, 2H), 7.53 (d, 2H), 7.44 (d, 1H), 6.91 (d, 1H), 4.64 (s, 2H), 3.36 (q, 2H), 2.03 (s, 3H) 1.15 (t, 3H)
MS: APCI (+ve) 367 (M+MeOH+H⁺)

EXAMPLE 167

[[4'-(Methylsulfonyl)-2',5-bis(trifluoromethyl)[1,1'-biphenyl]-2-yl]oxy]acetic acid

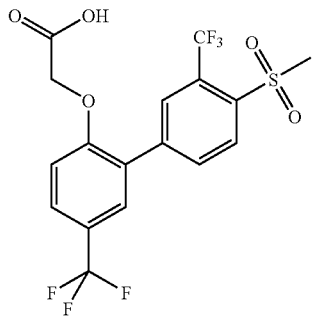

i) 4-Bromo-1-(methylthio)-2-(trifluoromethyl)benzene

Isopentyl nitrite (0.67 ml) was added dropwise to a solution of 4-bromo-2-(trifluoromethyl)aniline (1.2 g) and dimethyl sulfide (0.45 ml) in acetonitrile (12 ml). The reaction was slowly heated to reflux and then refluxed until gas evolution ceased. The volatiles were evaporated, the residue absorbed onto silica and the product eluted off with isohexane. Yield 0.8 g.
¹H NMR DMSO-d6: δ 7.59 (dd, 2H), 7.23 (d, 1H), 2.51 (s, 3H)

ii) 4,4,5,5-Tetramethyl-2-[4-(methylthio)-3-(trifluoromethyl)phenyl]-1,3,2-dioxaborolane Pd₂dba₃ (0.135 g) and tricyclohexylphosphine (0.199 g) were dissolved in dioxane (20 ml) and stirred for 30 min. Potassium acetate (0.867 g), bis(pinacolato)diboron (1.65 g) and the product from step (i) were sequentially added and the mixture heated at 90° C. for 3 h. The reaction was cooled, evaporated, partitioned between ether and brine, separated, dried (Na₂SO₄) and evaporated. The residue was purified by chromatography on silica eluting with 10% ether/isohexane. Yield 0.695 g.
¹H NMR DMSO-d6: δ 7.31 (d, 2H), 2.53 (s, 3H), 1.3 (s, 12H)

iii) 2-Bromo-4-(trifluoromethyl)phenoxyacetic acid, 1,1-dimethylethyl ester

The title compound was prepared by the method of example 1 step (i) using 2-bromo-4-(trifluoromethyl)phenol.

¹H NMR DMSO-d6: δ 6.8-7.83 (m, 3), 4.65 (s, 2H), 1.48 (s, 9H)

iv) [[4'-(Methylthio)-2',5-bis(trifluoromethyl)[1,1'-biphenyl]-2-yl]oxy]acetic acid, 1,1-dimethylethyl ester The title compound was prepared by the method of example 1 step (ii) using the products from steps (ii) and (iii). Yield 0.564 g. Carried forward to step (v) without characterisation.

v) [[4'-(Methylsulfonyl)-2',5-bis(trifluoromethyl)[1,1'-biphenyl]-2-yl]oxy]acetic acid, 1,1-dimethylethyl ester The product from step (iv) (0.564 g) was dissolved in 50% aqueous acetone (10 ml), sodium bicarbonate (0.94 g) added, followed by a solution of oxone (1.5 g) in water (ml) and stirred for 3 h. The reaction was quenched with aqueous sodium metabisulfite, extracted with EtOAc, washed with aqueous potassium carbonate, dried (Na₂SO₄) and evaporated to give the subtitle compound. Yield 0.32 g.
¹H NMR DMSO-d6: δ 8.31 (d, 1H), 8.29 (s, 1H), 8.18 (dd, 1H), 7.83 (s, 1H), 7.81 (d, 1H), 7.32 (d, 1H), 4.9 (s, 2H), 3.36 (s, 2H), 1.41 (s, 9H)

vi) [[4'-(Methylsulfonyl)-2',5-bis(trifluoromethyl)[1,1'-biphenyl]-2-yl]oxy]acetic acid The title compound was prepared by the method of example 26 step (vi) using the product from step (v). Yield 0.2 g.
¹H NMR DMSO-d6: δ 8.33 (s, 1H), 8.3 (d, 1H), 8.19 (d, 1H), 7.83 (s, 1H), 7.81 (d, 1H), 7.34 (d, 1H), 4.92 (s, 21), 3.36 (s, 2H)
MS: APCI (−ve) 441

EXAMPLE 168

2-[4-Chloro-2-[4-methyl-6-[methyl(methylsulfonyl)amino]-3-pyridinyl]phenoxy]-(2S)-propanoic acid

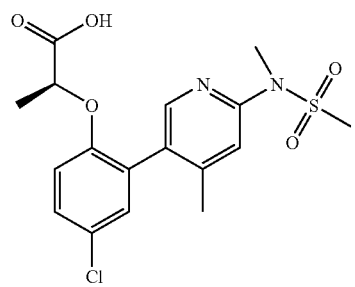

i) N-(5-Bromo-4-methyl-2-pyridinyl)methanesulfonamide

5-Bromo-4-methylpyridin-2-amine (1.56 g) was dissolved in DCM (40 ml), trimethylamine (1.4 ml) added, followed by methanesulfonyl chloride (1.9 g) and the mixture stirred for 20 min. The solution was washed with water, dried (MgSO₄) and evaporated. The residue was dissolved in THF, treated with TBAF, stirred for 16 h and evaporated. The residue was purified by chromatography on silica eluting with 27% EtOAc/isohexane. Yield 1.3 g. Carried forward to step (ii) without characterisation.

ii) N-(5-Bromo-4-methyl-2-pyridinyl)-N-methyl-methanesulfonamide

The product from step (i) (2.23 g), potassium carbonate (2.33 g) and methyl iodide (0.7 ml) were stirred in DMF (20 ml) for 20 h. The reaction was quenched with water, extracted with EtOAc, dried ($MgSO_4$) and evaporated. The residue was purified by chromatography on silica eluting with 30% EtOAc/isohexane. Yield 1.5 g. Carried forward to step (ii) without characterisation.

iii) 2-[4-Chloro-2-[4-methyl-6-[methyl(methylsulfonyl)amino]-3-pyridinyl]phenoxy]-(2S)-propanoic acid The title compound was prepared by the method of example 155 using the product from step (ii) and the product from example 151 step (iv). Yield 0.125 g.
$^1$H NMR DMSO-d6: δ 8.18 (s, 1H), 7.26-7.44 (m, 3H), 6.94 (d, 1H—), 4.8 (m, 1H), 3.32 (s, 3H), 3.2 (s, 3H), 2.2 (s, 3H), 1.32 (d, 3H)
MS: APCI (–ve) 397

EXAMPLE 169

2-[2-[4-Methyl-2-[(methylsulfonyl)amino]-5-pyrimidinyl]-4-(trifluoromethyl)phenoxy]-(2S)-propanoic acid

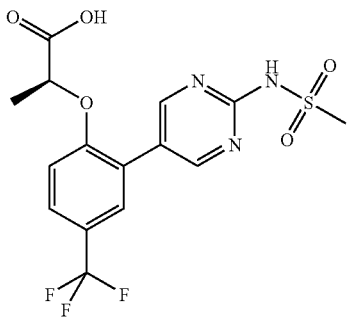

i) Potassium N-(5-bromo-4-methyl-2-pyrimidinyl)methanesulfonamide

Methanesulfonyl chloride (0.75 ml) was added to a solution of 5-bromo-4-methyl-2-pyrimidinamine (1.8 g) in THF (60 ml), followed by the rapid dropwise addition of 1M potassium tert-butoxide/THF (20 ml). After 30 min the resulting precipitate was filtered off and dried. Yield 3.2 g.
$^1$H NMR DMSO-d6: δ 8.13 (s, 1H), 2.81 (s, 3H), 2.26 (s, 3H)

ii) N-(5-Bromo-4-methyl-2-pyrimidinyl)-N-[[2-(trimethylsilyl)ethoxy]methyl]methanesulfonamide

[2-(Chloromethoxy)ethyl]trimethylsilane (0.4 ml) was added to a solution of the product from step (i) in DMF (10 ml) and stirred for 20 min. The mixture was poured into water, extracted with ether, washed with brine, dried ($MgSO_4$) and evaporated. The residue was purified by chromatography on silica eluting with 20% EtOAc/isohexane. Yield 0.53 g.
$^1$H NMR DMSO-d6: δ 8.88 (s, 1H), 5.49 (s, 2H), 3.59-3.64 (m, 5H), 2.63 (s, 3H), 0.9 (t, 2H), 0.0 (t, 9H)

iii) 2-[2-[4-Methyl-2-[(methylsulfonyl)[[2-(trimethylsilyl)ethoxy]methyl]amino]-5-pyrimidinyl]-4-(trifluoromethyl)phenoxy]-(2S)-propanoic acid The title compound was prepared by the method of example 144 step (i) using the product from step (ii) and the product from example 146 step (iv). Carried forward to step (iv) without characterisation.

iv) 2-[2-[4-Methyl-2-[(methylsulfonyl)amino]-5-pyrimidinyl]-4-(trifluoromethyl)phenoxy]-(2S)-propanoic acid The product from step (iii) was treated with TFA (20 ml) and stirred for 20 min. The TFA was evaporated and the residue purified by RVHPLC ($CH_3CN$/aqTFA).
$^1$H NMR DMSO-d6: δ 8.84 (s, 1H), 7.77 (dd, 2H), 7.65 (d, 1H), 7.14 (d, 5H), 5.04 (q, 1H), 3.4 (s, 31-1), 2.3 (s, 3H), 1.41 (d, 3H)
MS: APCI (–ve) 418

EXAMPLE 170

[(5-Chloro-3'-cyano[1,1'-biphenyl]-2-yl)oxy]-acetic acid

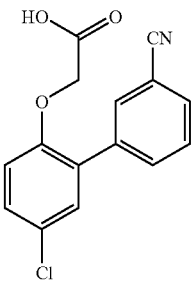

(i) 5'-Chloro-2'-methoxy-[1,1'-biphenyl]-3-carbonitrile

The subtitle compound was prepared by the method of example 1 step (ii) using 3-iodobenzonitrile and 5-chloro-2-methoxyphenyl boronic acid. Yield 0.465 g
$^1$H NMR $CDCl_3$: δ 7.82 (1H, t), 7.71 (1H, dt), 7.62 (1H, dt), 7.51 (1H, t), 7.32 (2H, dd), 7.26 (1H, m), 6.93 (1H, d), 3.81 (3H, s)

(ii) 5'-Chloro-2'-hydroxy-[1,1'-biphenyl]-3-carbonitrile

A solution of boron tribromide (1M in dichloromethane, 6 ml) was added to a stirred solution of the product from step (i) in dichloromethane (10 ml) at 0° C. After 15 min the mixture was warmed to room temperature, stirred for 16 h then poured onto ice. The mixture was extracted with dichloromethane then ethylacetate, the organics combined, dried and evaporated under reduced pressure. The residue was purified by chromatography on silica eluting with 30-70% diethylether/isohexane. Yield 0.415 g $^1$H NMR CDCl$_3$: δ 7.83 (1H, s), 7.75 (1H, d), 7.68 (1H, d), 7.58 (1H, t), 7.25 (2H, m), 6.89 (1H, d), 5.00 (1H, s)

(iii) [(5-chloro-3'-cyano[1,1'-biphenyl]-2-yl)oxy]-acetic acid, 1,1-dimethylethyl ester The subtitle compound was prepared by the method of example 1 step (i) using the product from step (ii). Yield 0.60 g $^1$H NMR CDCl$_3$: δ 7.90 (1H, s), 7.82 (1H, d), 7.63 (1H, d), 7.53 (1H, td), 7.28 (2H, m), 6.78 (1H, d), 4.52 (2H, s), 1.47 (10H, s)

(iv) [(5-Chloro-3'-cyano[1,1'-biphenyl]-2-yl)oxy]-acetic acid

The title compound was prepared by the method of example 1 step (iii) using the product from step (iii). Yield 0.265 g $^1$H NMR DMSO-d6: δ 13.12 (1H, s), 8.08 (1H, s), 7.94 (1H, d), 7.82 (1H, d), 7.64 (1H, t), 7.43 (2H, m), 7.10 (1H, d), 4.78 (2H, s).

MS: APCI (−ve): 286

Pharmacological Data

Ligand Binding Assay

[$^3$H]PGD$_2$ was purchased from Perkin Elmer Life Sciences with a specific activity of 100-210 Ci/mmol. All other chemicals were of analytical grade.

HEK cells expressing rhCRTh2/Gα16 were routinely maintained in DMEM containing 10% Foetal Bovine Serum (HyClone), 1 mg/ml geneticin, 2 mM L-glutamine and 1% non-essential amino acids. For the preparation of membranes, the adherent transfected HEK cells were grown to confluence in two layer tissue culture factories (Fisher, catalogue number TKT-170-070E). Maximal levels of receptor expression were induced by addition of 500 mM sodium butyrate for the last 18 hours of culture. The adherent cells were washed once with phosphate buffered saline (PBS, 50 ml per cell factory) and detached by the addition of 50 ml per cell factory of ice-cold membrane homogenisation buffer [20 mM HEPES (pH 7.4), 0.1 mM dithiothreitol, 1 mM EDTA, 0.1 mM phenyl methyl sulphonyl fluoride and 100 μg/ml bacitracin]. Cells were pelleted by centrifugation at 220×g for 10 minutes at 4° C., re-suspended in half the original volume of fresh membrane homogenisation buffer and disrupted using a Polytron homogeniser for 2×20 second bursts keeping the tube in ice at all times. Unbroken cells were removed by centrifugation at 220×g for 10 minutes at 4° C. and the membrane fraction pelleted by centrifugation at 90000×g for 30 minutes at 4° C. The final pellet was re-suspended in 4 ml of membrane homogenisation buffer per cell factory used and the protein content determined. Membranes were stored at −80° C. in suitable aliquots.

All assays were performed in Corning clear bottomed, white 96-well NBS plates (Fisher). Prior to assay, the HEK cells membranes containing CRTh2 were coated onto SPA PVT WGA beads (Amersham). For coating membranes were incubated with beads at typically 25 μg membrane protein per mg beads at 4° C. with constant agitation overnight. (The optimum coating concentrations were determined for each batch of membranes) The beads were pelleted by centrifugation (800×g for 7 minutes at 4° C.), washed once with assay buffer (50 mM HEPES pH 7.4 containing 5 mM magnesium chloride) and finally re-suspended in assay buffer at a bead concentration of 10 mg/ml.

Each assay contained 20 μl of 6.25 nM [$^3$H]PGD$_2$, 20 μl membrane saturated SPA beads both in assay buffer and 10 μl of compound solution or 13,14-dihydro-15-keto prostaglandin D$_2$ (DK-PGD$_2$, for determination of non-specific binding, Cayman chemical company). Compounds and DK-PGD$_2$ were dissolved in DMSO and diluted in the same solvent to 100× the required final concentration. Assay buffer was added to give a final concentration of 10% DMSO (compounds were now at 10× the required final concentration) and this was the solution added to the assay plate. The assay plate was incubated at room temperature for 2 hours and counted on a Wallac Microbeta liquid scintillation counter (1 minute per well).

Compounds of formula (I) have an IC$_{50}$ value of less than (<) 10 μM.

Specifically, example 9 has a pIC$_{50}$=7.4, example 25 has a pIC$_{50}$=8.0, and example 133 has a pIC$_{50}$=8.2.

The invention claimed is:

1. A compound of formula (I) or a pharmaceutically acceptable salt thereof:

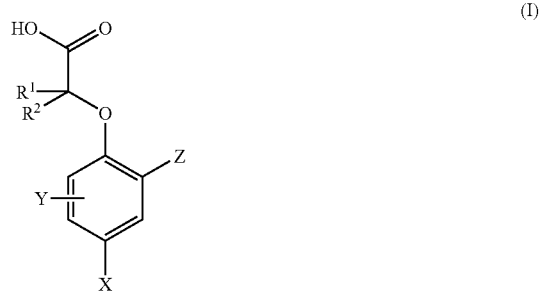

(I)

in which:

X is halogen, cyano, nitro, S(O)$_n$R$^6$ (wherein n is 0, 1 or 2) or C$_{1-4}$-alkyl which is substituted by one or more halogen atoms;

Y is hydrogen;

Z is phenyl or naphthyl each of which is substituted by one or more substituents independently selected from halogen, CN, OH, SH, nitro, COR$^9$, CO$_2$R$^6$, SO$_2$R$^9$, OR$^9$, SR$^9$, SOR$^9$, SO$_2$NR$^{10}$R$^{11}$, CONR$^{10}$R$^{11}$, NR$^{10}$R$^{11}$, NHSO$_2$R$^9$, NR$^5$SO$_2$R$^9$, NR$^6$CO$_2$R$^6$, NHCOR$^9$, NR$^9$COR$^9$, NR$^6$CONR$^4$R$^5$, NR$^6$SO$_2$NR$^4$R$^5$, aryl, heteroaryl, C$_2$-C$_6$ alkenyl, C$_2$-C$_6$ alkynyl, C$_3$-C$_7$ cycloalkyl or C$_{1-6}$alkyl, the latter four groups being optionally substituted by one or more substituents independently selected from halogen, C$_3$-C$_7$ cycloalkyl, OR$^6$, NR$^6$R$^7$, S(O)$_n$R$^6$ (wherein n is 0, 1 or 2), CONR$^6$R$^7$, NR$^6$COR$^7$, SO$_2$NR$^6$R$^7$ and NR$^6$SO$_2$R$^7$;

R$^1$ and R$^2$ independently represent a hydrogen atom, halogen, C$_2$-C$_6$ alkenyl, C$_2$-C$_6$ alkynyl, C$_3$-C$_7$ cycloalkyl or a C$_{1-6}$alkyl group, the latter four groups being optionally substituted by one or more substituents independently selected from halogen, C$_3$-C$_7$ cycloalkyl, NR$^6$R$^7$, OR$^6$, S(O)$_n$R$^6$ (wherein n is 0, 1 or 2);

or

R$^1$ and R$^2$ together can form a 3-8 membered ring optionally containing one or more atoms selected from O, S, NR$^6$ and itself optionally substituted by one or more C$_1$-C$_3$ alkyl or halogen;

R$^3$ represents C$_3$-C$_7$ cycloalkyl or C$_{1-6}$alkyl which may be optionally substituted by one or more substituents independently selected from halogen, C$_3$-C$_7$ cycloalkyl, OR$^6$ and NR$^6$R$^7$, S(O)$_n$R$^6$ (wherein n is 0, 1 or 2), CONR$^6$R$^7$, NR$^6$COR$^7$, SO$_2$NR$^6$R$^7$ and NR$^6$SO$_2$R$^7$;

R⁴ and R⁵ independently represent hydrogen, $C_3$-$C_7$ cycloalkyl or $C_{1-6}$alkyl, the latter two groups being optionally substituted by one or more substituents independently selected from halogen, $C_3$-$C_7$ cycloalkyl, $OR^6$ and $NR^6R^7$, $S(O)_nR^6$ (wherein n is 0, 1 or 2), $CONR^6R^7$, $NR^6COR^7$, $SO_2NR^6R^7$ and $NR^6SO_2R^7$;

or

R⁴ and R⁵ together with the nitrogen atom to which they are attached can form a 3-8 membered saturated heterocylic ring optionally containing one or more atoms selected from 0, $S(O)_n$ (wherein n is 0, 1 or 2), $NR^8$, and itself optionally substituted by halogen or $C_{1-3}$ alkyl;

R⁶ and R⁷ independently represents a hydrogen atom or $C_1$-$C_6$ alkyl;

R⁸ is hydrogen, $C_{1-4}$ alkyl, —$COC_1$-$C_4$ alkyl, $CO_2C_1$-$C_4$alkyl or $CONR^6C_1$-$C_4$alkyl;

R⁹ represents aryl, heteroaryl, $C_3$-$C_7$ cycloalkyl or $C_{1-6}$alkyl, the latter two groups may be optionally substituted by one or more substituents independently selected from halogen, $C_3$-$C_7$ cycloalkyl, aryl, heteroaryl $OR^6$ and $NR^6R^7$, $S(O)_nR^6$ (wherein n is 0, 1 or 2), $CONR^6R^7$, $NR^6COR^7$, $SO_2NR^6R^7$ and $NR^6SO_2R^7$;

R¹⁰ and R¹¹ independently represent aryl or heteroaryl, hydrogen, $C_3$-$C_7$ cycloalkyl or $C_{1-6}$alkyl, the latter two groups being optionally substituted by one or more substituents independently selected from halogen, $C_3$-$C_7$ cycloalkyl, aryl, heteroaryl, $OR^6$ and $NR^6R^7$, $S(O)_nR^6$ (wherein n is 0, 1 or 2), $CONR^6R^7$, $NR^6COR^7$, $SO_2NR^6R^7$ and $NR^6SO_2R^7$;

or

R¹⁰ and R¹¹ together with the nitrogen atom to which they are attached can form a 3-8 membered saturated heterocylic ring optionally containing one or more atoms selected from O, $S(O)_n$ (wherein n is 0, 1 or 2), $NR^8$, and itself optionally substituted by halogen or $C_1$-$C_3$ alkyl.

2. A compound according to claim 1 in which X is halogen, cyano, nitro, $S(O)_nR^6$ or $C_{1-4}$alkyl which is substituted by one or more halogen atoms.

3. A compound according to claim 1 in which X is trifluoromethyl, nitro, cyano or halogen.

4. A compound according to claim 1 in which Z is phenyl, which is substituted with one or more substituents as defined in claim 1.

5. A compound according to claim 1 in which both R¹ and R² are hydrogen or one is hydrogen and the other is methyl or ethyl or both are methyl.

6. A compound according to claim 1 selected from:
{[5-Chloro-4'-(ethylthio)biphenyl-2-yl]oxy}acetic acid,
{[5-Chloro-4'-(ethylsulfonyl)biphenyl-2-yl]oxy}acetic acid,
[(4',5-Dichlorobiphenyl-2-yl)oxy]acetic acid,
[(5-Chloro-4'-cyanobiphenyl-2-yl)oxy]acetic acid,
[(5-Chloro-4'-methoxybiphenyl-2-yl)oxy]acetic acid,
[(5-Chloro-3',4'-dimethoxybiphenyl-2-yl)oxy]acetic acid,
2'-(Carboxymethoxy)-5'-chlorobiphenyl-4-carboxylic acid,
{[5-Chloro-4'-(methylsulfonyl)biphenyl-2-yl]oxy}acetic acid,
{[5-Chloro-4'-(ethylsulfonyl)-2'-methylbiphenyl-2-yl]oxy}acetic acid,
{[4'-(Methylthio)-5-(trifluoromethyl)biphenyl-2-yl]oxy}acetic acid,
{[4'-(Methylsulfonyl)-5-(trifluoromethyl)biphenyl-2-yl]oxy}acetic acid,
{[4'-(Ethylsulfonyl)-2'-methyl-5-(trifluoromethyl)biphenyl-2-yl]oxy}acetic acid,
[[2',5-Dichloro-4'-(ethylsulfonyl)[1,1'-biphenyl]-2-yl]oxy]-acetic acid,
[[2'-Chloro-4'-(ethylsulfonyl)-5-(trifluoromethyl)[1,1'-biphenyl]-2-yl]oxy]-acetic acid,
[[5-Chloro-4'-(ethylsulfonyl)-2'-fluoro[1,1'-biphenyl]-2-yl]oxy]-acetic acid,
[[4'-(Ethylsulfonyl)-2'-fluoro-5-(trifluoromethyl)[1,1'-biphenyl]-2-yl]oxy]-acetic acid,
[[5-Chloro-4'-(ethylsulfonyl)-2'-(trifluoromethyl)[1,1'-biphenyl]-2-yl]oxy]-acetic acid,
2-[[5-Chloro-4'-(ethylsulfonyl)[1,1'-biphenyl]-2-yl]oxy]-propanoic acid,
2-[[4'-(Ethylsulfonyl)-2'-methyl-5-(trifluoromethyl)[1,1'-biphenyl]-2-yl]oxy]-(2S)-propanoic acid,
2-[[4'-(Ethylsulfonyl)-2'-methyl-5-(trifluoromethyl)[1,1'-biphenyl]-2-yl]oxy]-(2R)-propanoic acid,
2-[[2',5-Dichloro-4'-(ethylsulfonyl)[1,1'-biphenyl]-2-yl]oxy]-(25)-propanoic acid,
2-[[2'-Chloro-4'-(ethylsulfonyl)-5-(trifluoromethyl)[1,1'-biphenyl]-2-yl]oxy]-(25)-propanoic acid,
2-[[4'-(Ethylsulfonyl)-2'-methyl-5-(trifluoromethyl)[1,1'-biphenyl]-2-yl]oxy]-2-methyl-propanoic acid,
2-[[4'-(Ethylsulfonyl)-2'-methyl-5-(trifluoromethyl)[1,1'-biphenyl]-2-yl]oxy]-butanoic acid,
[[4'-(Ethylsulfonyl)-5-fluoro-2'-methyl[1,1'-biphenyl]-2-yl]oxy]-acetic acid,
[[4'-(Ethylsulfonyl)-4,5-difluoro-2'-methyl[1,1'-biphenyl]-2-yl]oxy]-acetic acid,
[[4'-(Ethylsulfonyl)-3,5-difluoro-2'-methyl[1,1'-biphenyl]-2-yl]oxy]-acetic acid,
[[4'-Amino-2'-methyl-5-(trifluoromethyl)[1,1'-biphenyl]-2-yl]oxy]-acetic acid,
[[4'-Amino-2'-chloro-5-(trifluoromethyl)[1,1'-biphenyl]-2-yl]oxy]-acetic acid,
[[2'-Chloro-4'-hydroxy-5-(trifluoromethyl)[1,1'-biphenyl]-2-yl]oxy]-acetic acid,
[[2'-Chloro-5-(trifluoromethyl)[1,1'-biphenyl]-2-yl]oxy]-acetic acid,
[[2',5-Bis(trifluoromethyl)[1,1'-biphenyl]-2-yl]oxy]-acetic acid,
[[5'-Fluoro-2'-methoxy-5-(trifluoromethyl)[1,1'-biphenyl]-2-yl]oxy]-acetic acid,
[[5'-Cyano-2'-methoxy-5-(trifluoromethyl)[1,1'-biphenyl]-2-yl]oxy]-acetic acid,
[[4'-Chloro-2'-methyl-5-(trifluoromethyl)[1,1'-biphenyl]-2-yl]oxy]-acetic acid,
[[2',5'-Dimethyl-5-(trifluoromethyl)[1,1'-biphenyl]-2-yl]oxy]-acetic acid,
[[5'-Chloro-2'-methyl-5-(trifluoromethyl)[1,1'-biphenyl]-2-yl]oxy]-acetic acid,
[[2'-Fluoro-6'-methyl-5-(trifluoromethyl)[1,1'-biphenyl]-2-yl]oxy]-acetic acid,
[[4'-Fluoro-2'-methyl-5-(trifluoromethyl)[1,1'-biphenyl]-2-yl]oxy]-acetic acid,
[[4'-[[(Ethylamino)carbonyl]amino]-2'-methyl-5-(trifluoromethyl)[1,1'-biphenyl]-2-yl]oxy]-acetic acid,
[[2'-Methyl-4'-[[(methylamino)carbonyl]amino]-5-(trifluoromethyl)[1,1'-biphenyl]-2-yl]oxy]-acetic acid,
[[4'-[[(Cyclopropylamino)carbonyl]amino]-2'-methyl-5-(trifluoromethyl)[1,1'-biphenyl]-2-yl]oxy]-acetic acid,
[[2'-Methyl-4'-[[(propylamino)carbonyl]amino]-5-(trifluoromethyl)[1,1'-biphenyl]-2-yl]oxy]-acetic acid,
[[2',4'-Dimethyl-5-(trifluoromethyl)[1,1'-biphenyl]-2-yl]oxy]-acetic acid,
[[5'-Fluoro-2'-methyl-5-(trifluoromethyl)[1,1'-biphenyl]-2-yl]oxy]-acetic acid,

[[4'-(Aminocarbonyl)-2'-methyl-5-(trifluoromethyl)[1,1'-biphenyl]-2-yl]oxy]-acetic acid,
[[3'-Fluoro-2'-methyl-5-(trifluoromethyl)[1,1'-biphenyl]-2-yl]oxy]-acetic acid,
[[2',5'-Difluoro-5-(trifluoromethyl)[1,1'-biphenyl]-2-yl]oxy]-acetic acid,
[[5'-(Aminosulfonyl)-2'-chloro-5-(trifluoromethyl)[1,1'-biphenyl]-2-yl]oxy]-acetic acid,
[[4'-Cyano-2'-methyl-5-(trifluoromethyl)[1,1'-biphenyl]-2-yl]oxy]-acetic acid,
[[4'-Chloro-2'-fluoro-5-(trifluoromethyl)[1,1'-biphenyl]-2-yl]oxy]-acetic acid,
[[2',5'-Difluoro-4'-methoxy-5-(trifluoromethyl)[1,1'-biphenyl]-2-yl]oxy]-acetic acid,
[[2'-fluoro-5'-methyl-5-(trifluoromethyl)[1,1'-biphenyl]-2-yl]oxy]-acetic acid,
[[2'-Fluoro-4'-methyl-5-(trifluoromethyl)[1,1'-biphenyl]-2-yl]oxy]-acetic acid,
[[4'-Methoxy-2'-methyl-5-(trifluoromethyl)[1,1'-biphenyl]-2-yl]oxy]-acetic acid,
[[4'-(Aminosulfonyl)-2',5'-difluoro-5-(trifluoromethyl)[1,1'-biphenyl]-2-yl]oxy]-acetic acid,
[[4'-Chloro-5-(trifluoromethyl)[1,1'-biphenyl]-2-yl]oxy]-acetic acid,
[[3'-(1-Methylethyl)-5-(trifluoromethyl)[1,1'-biphenyl]-2-yl]oxy]-acetic acid,
[[3',4'-Difluoro-5-(trifluoromethyl)[1,1'-biphenyl]-2-yl]oxy]-acetic acid,
[[4'-Ethyl-5-(trifluoromethyl)[1,1'-biphenyl]-2-yl]oxy]-acetic acid,
[[3'-Fluoro-5-(trifluoromethyl)[1,1':4',1''-terphenyl]-2-yl]oxy]acetic acid,
[[4'-(Trifluoromethoxy)-5-(trifluoromethyl)[1,1'-biphenyl]-2-yl]oxy]-acetic acid,
[[2',3'-Dichloro-5-(trifluoromethyl)[1,1'-biphenyl]-2-yl]oxy]-acetic acid,
[[4'-(1,1-Dimethylethyl)-5-(trifluoromethyl)[1,1'-biphenyl]-2-yl]oxy]-acetic acid,
2-(6-Methoxy-2-naphthalenyl)-4-(trifluoromethyl)phenoxy]-acetic acid,
[[4'-(Ethylthio)-5-(trifluoromethyl)[1,1'-biphenyl]-2-yl]oxy]-acetic acid,
[[4'-Acetyl-5-(trifluoromethyl)[1,1'-biphenyl]-2-yl]oxy]-acetic acid,
[[5'-(Aminosulfonyl)-2'-methyl-5-(trifluoromethyl)[1,1'-biphenyl]-2-yl]oxy]-acetic acid,
[[3'-Cyano-5-(trifluoromethyl)[1,1'-biphenyl]-2-yl]oxy]-acetic acid,
[[2'-Methyl-5'-(methylsulfonyl)-5-(trifluoromethyl)[1,1'-biphenyl]-2-yl]oxy]-acetic acid,
2'-(Carboxymethoxy)-5'-(trifluoromethyl)-[1,1'-biphenyl]-3-carboxylic acid, 3-methyl ester,
2'-(Carboxymethoxy)-5'-(trifluoromethyl)-[1,1'-biphenyl]-2-carboxylic acid, 2-methyl ester,
[[5-(Trifluoromethyl)[1,1':4',1''-terphenyl]-2-yl]oxy]-acetic acid,
[[3'-Fluoro-2',4'-dimethyl-5-(trifluoromethyl)[1,1'-biphenyl]-2-yl]oxy]-acetic acid,
[[2'-Nitro-5-(trifluoromethyl)[1,1'-biphenyl]-2-yl]oxy]-acetic acid,
[[2'-Methyl-5-(trifluoromethyl)[1,1'-biphenyl]-2-yl]oxy]-acetic acid,
[[3'-Chloro-2'-methyl-5-(trifluoromethyl)[1,1'-biphenyl]-2-yl]oxy]-acetic acid,
[[5-(Trifluoromethyl)[1,1':3',1''-terphenyl]-2-yl]oxy]-acetic acid,
2'-(Carboxymethoxy)-5'-(trifluoromethyl)-[1,1'-biphenyl]-4-carboxylic acid, 4-methyl ester,
[[4'-Nitro-5-(trifluoromethyl)[1,1'-biphenyl]-2-yl]oxy]-acetic acid,
[[5-(Trifluoromethyl)-3'-[(trifluoromethyl)thio][1,1'-biphenyl]-2-yl]oxy]-acetic acid,
[[5-(Trifluoromethyl)-4'-[(trifluoromethyl)thio][1,1'-biphenyl]-2-yl]oxy]-acetic acid,
[[4'-Methyl-5-(trifluoromethyl)[1,1'-biphenyl]-2-yl]oxy]-acetic acid,
[[4'-Fluoro-5-(trifluoromethyl)[1,1'-biphenyl]-2-yl]oxy]-acetic acid,
[[3'-Fluoro-5-(trifluoromethyl)[1,1'-biphenyl]-2-yl]oxy]-acetic acid,
[[3'-Methyl-5-(trifluoromethyl)[1,1'-biphenyl]-2-yl]oxy]-acetic acid,
[[2'-Fluoro-5-(trifluoromethyl)[1,1'-biphenyl]-2-yl]oxy]-acetic acid,
[[2'-Methoxy-5-(trifluoromethyl)[1,1'-biphenyl]-2-yl]oxy]-acetic acid,
[[3'-Methoxy-5-(trifluoromethyl)[1,1'-biphenyl]-2-yl]oxy]-acetic acid,
[[4'-Methoxy-5-(trifluoromethyl)[1,1'-biphenyl]-2-yl]oxy]-acetic acid,
[[3'-(Ethylsulfonyl)-5-(trifluoromethyl)[1,1'-biphenyl]-2-yl]oxy]-acetic acid,
[[3'-Propoxy-5-(trifluoromethyl)[1,1'-biphenyl]-2-yl]oxy]-acetic acid,
[[4'-Propoxy-5-(trifluoromethyl)[1,1'-biphenyl]-2-yl]oxy]-acetic acid,
[2-(2-Amino-4-methyl-5-pyrimidinyl)-4-(trifluoromethyl)phenoxy]-acetic acid,
[[4'-Cyano-5-(trifluoromethyl)[1,1'-biphenyl]-2-yl]oxy]-acetic acid,
[[4',5-Bis(trifluoromethyl)[1,1'-biphenyl]-2-yl]oxy]-acetic acid,
[2-(2-Naphthalenyl)-4-(trifluoromethyl)phenoxy]-acetic acid,
[[4'-(1-Pyrrolidinylsulfonyl)-5-(trifluoromethyl)[1,1'-biphenyl]-2-yl]oxy]-acetic acid,
[[4'-[(Dimethylamino)sulfonyl]-5-(trifluoromethyl)[1,1'-biphenyl]-2-yl]oxy]-acetic acid,
[[4'-[[(Phenylmethyl)amino]sulfonyl]-5-(trifluoromethyl)[1,1'-biphenyl]-2-yl]oxy]-acetic acid,
[[4'-[[(2,2,2-Trifluoroethyl)amino]sulfonyl]-5-(trifluoromethyl)[1,1'-biphenyl]-2-yl]oxy]-acetic acid,
[[4'-[[(5-Methyl-2-thiazolyl)amino]sulfonyl]-5-(trifluoromethyl)[1,1'-biphenyl]-2-yl]oxy]-acetic acid,
[[4'-[(Phenylamino)sulfonyl]-5-(trifluoromethyl)[1,1'-biphenyl]-2-yl]oxy]-acetic acid,
[[4'-[(Diethylamino)sulfonyl]-5-(trifluoromethyl)[1,1'-biphenyl]-2-yl]oxy]-acetic acid,
[[4'-[(Cyclopropylamino)sulfonyl]-5-(trifluoromethyl)[1,1'-biphenyl]-2-yl]oxy]-acetic acid,
[[4'-(Aminosulfonyl)-5-(trifluoromethyl)[1,1'-biphenyl]-2-yl]oxy]-acetic acid,
[[4'-[(Methylamino)sulfonyl]-5-(trifluoromethyl)[1,1'-biphenyl]-2-yl]oxy]-acetic acid,
[[4'-[(4-Methyl-1-piperazinyl)sulfonyl]-5-(trifluoromethyl)[1,1'-biphenyl]-2-yl]oxy]-acetic acid,
2-[4-Methyl-2-(5-methyl-1,1-dioxido-1,2,5-thiadiazolidin-2-yl)-5-pyrimidinyl]-4-(trifluoromethyl)phenoxy]-acetic acid,
[[2'-Chloro-4'-[(methoxycarbonyl)amino]-5-(trifluoromethyl)[1,1'-biphenyl]-2-yl]oxy]acetic acid
2-[[2'-Chloro-4'-(methylsulfonyl)-5-(trifluoromethyl)[1,1'-biphenyl]-2-yl]oxy]-(2S)-propanoic acid, 2-[[3'-Cyano-5-(trifluoromethyl)[1,1'-biphenyl]-2-yl]
  oxy]-(2S)-propanoic acid,
2-[[4'-[(Dimethylamino)sulfonyl]-5-(trifluoromethyl)[1,
  1'-biphenyl]-2-yl]oxy]-(2S)-propanoic acid,
2-[[2'-Chloro-4'-[(dimethylamino)sulfonyl]-5-(trifluoromethyl)[1,1'-biphenyl]-2-yl]oxy]-(2S)-propanoic
  acid,
2-[[2'-Fluoro-4'-(methylsulfonyl)-5-(trifluoromethyl)[1,
  1'-biphenyl]-2-yl]oxy]-(2S)-propanoic acid,
[[2',5-Dichloro-4'-(methylsulfonyl)[1,1'-biphenyl]-2-yl]
  oxy]-(2S)-propanoic acid,
[[5-Chloro-4'-[(dimethylamino)sulfonyl][1,1'-biphenyl]-
  2-yl]oxy]-(2S)-propanoic acid,
[[2',5-Dichloro-4'-[(dimethylamino)sulfonyl][1,1'-biphenyl]-2-yl]oxy]-(2S)-propanoic acid,
[(5-Chloro-3'-cyano[1,1'-biphenyl]-2-yl)oxy]-(2S)-propanoic acid,
[[5-Chloro-4'-[(dimethylamino)sulfonyl]-2'-fluoro[1,1'-biphenyl]-2-yl]oxy]-(2S)-propanoic acid,
[[5-Chloro-4'-(4-morpholinylsulfonyl)[1,1'-biphenyl]-2-yl]oxy]-(2S)-propanoic acid,
[[5-Chloro-2'-fluoro-4'-(methylsulfonyl)[1,1'-biphenyl]-2-yl]oxy]-(2S)-propanoic acid,
2-[[4'-(1-Azetidinylsulfonyl)-5-chloro[1,1'-biphenyl]-2-yl]oxy]-(2S)-propanoic acid,
2-[[5-Chloro-2'-methyl-4'-(1-pyrrolidinylcarbonyl)[1,1'-biphenyl]-2-yl]oxy]-(2S)-propanoic acid,
2-[(2',4'-Dichloro-5-cyano[1,1'-biphenyl]-2-yl)oxy]-(2S)-propanoic acid,
2-[[5-Cyano-2'-fluoro-4'-(trifluoromethyl)[1,1'-biphenyl]-2-yl]oxy]-(2S)-propanoic acid,
2-[(3'-Cyano-5-fluoro[1,1'-biphenyl]-2-yl)oxy]-(2S)-propanoic acid, sodium salt,
2-[(2',4'-Dichloro-5-fluoro[1,1'-biphenyl]-2-yl)oxy]-(2S)-propanoic acid, sodium salt,
2-[[2'-Chloro-5-fluoro-4'-(methylsulfonyl)[1,1'-biphenyl]-2-yl]oxy]-(2S)-propanoic acid
2-[[2'-Chloro-5-fluoro-5'-(trifluoromethyl)[1,1'-biphenyl]-2-yl]oxy]-(2S)-propanoic acid,
[[4'-(Methylsulfonyl)-2',5-bis(trifluoromethyl)[1,1'-biphenyl]-2-yl]oxy]acetic acid, and
[(5-Chloro-3'-cyano[1,1'-biphenyl]-2-yl)oxy]-acetic acid,
and pharmaceutically acceptable salts thereof.

7. A method of treating asthma or rhinitis in a patient suffering from, or at risk of, asthma or rhinitis, which comprises administering to the patient a therapeutically effective amount of a compound of formula (I), or a pharmaceutically acceptable salt thereof, as defined in claim 1.

8. A compound according to claim 2, in which Z is phenyl, which is substituted with one or more substituents as defined in claim 1.

9. A compound according to claim 2, in which both $R^1$ and $R^2$ are hydrogen or one is hydrogen and the other is methyl or ethyl or both are methyl.

10. A compound according to claim 3, in which Z is phenyl, which is substituted with one or more substituents as defined in claim 1.

11. A compound according to claim 3, in which both $R^1$ and $R^2$ are hydrogen or one is hydrogen and the other is methyl or ethyl or both are methyl.

* * * * *